(12) United States Patent
Xu et al.

(10) Patent No.: US 12,240,841 B2
(45) Date of Patent: Mar. 4, 2025

(54) FXR SMALL MOLECULE AGONIST AND PREPARATION METHOD THEREFOR AND USE THEREOF

(71) Applicants: Shanghai Institute of Materia Medica, Chinese Academy of Sciences, Shanghai (CN); Van Andel Research Institute, Grand Rapids, MI (US)

(72) Inventors: Huaqiang Xu, Pudong Shanghai (CN); Jia Li, Pudong Shanghai (CN); Jingjing Shi, Pudong Shanghai (CN); Yi Zang, Pudong Shanghai (CN); Dandan Sun, Pudong Shanghai (CN); Mingliang Liu, Pudong Shanghai (CN); Rongrong Xie, Pudong Shanghai (CN); Erli You, Pudong Shanghai (CN); Lixin Gao, Pudong Shanghai (CN); Qian Tan, Pudong Shanghai (CN)

(73) Assignees: SHANGHAI INSTITUTE OF MATERIA MEDICA, CHINESE ACADEMY OF SCIENCES, Shanghai (CN); VAN ANDEL RESEARCH INSTITUTE, Grand Rapids, MI (US)

( * ) Notice: Subject to any disclaimer, the term of this patent is extended or adjusted under 35 U.S.C. 154(b) by 738 days.

(21) Appl. No.: 17/603,823

(22) PCT Filed: Apr. 20, 2020

(86) PCT No.: PCT/CN2020/085713
§ 371 (c)(1),
(2) Date: Oct. 14, 2021

(87) PCT Pub. No.: WO2020/211872
PCT Pub. Date: Oct. 22, 2020

(65) Prior Publication Data
US 2022/0213083 A1 Jul. 7, 2022

(30) Foreign Application Priority Data

Apr. 19, 2019 (CN) .......................... 201910319757.X
Oct. 12, 2019 (CN) .......................... 201910969552.6

(51) Int. Cl.
*C07D 413/14* (2006.01)
*A61P 1/16* (2006.01)
*C07D 487/08* (2006.01)

(52) U.S. Cl.
CPC .............. *C07D 413/14* (2013.01); *A61P 1/16* (2018.01); *C07D 487/08* (2013.01)

(58) Field of Classification Search
CPC .... A61K 45/06; A61K 31/439; A61K 31/454; A61K 31/55; A61P 1/16; A61P 29/00; A61P 3/00; A61P 3/06; A61P 3/10; C07D 413/14; C07D 451/06; C07D 487/08; C07D 471/08

See application file for complete search history.

(56) References Cited

U.S. PATENT DOCUMENTS

| 9,150,568 B2 | 10/2015 | Tully et al. |
| 9,751,874 B2 | 9/2017 | Gege et al. |
| 11,667,629 B2 * | 6/2023 | Liu ...................... C07D 417/14 514/315 |
| 2015/0366856 A1 | 12/2015 | Tully et al. |
| 2022/0213083 A1 | 7/2022 | Xu et al. |

FOREIGN PATENT DOCUMENTS

| CN | 107973790 A | 5/2018 |
| CN | 108017636 A | 5/2018 |
| CN | 108064223 A | 5/2018 |
| CN | 108602811 A | 9/2018 |
| CN | 109265471 A | 1/2019 |
| CN | 109906223 A | 6/2019 |
| CN | 111825667 A | 10/2020 |
| CN | 112812114 A | 5/2021 |
| JP | 2014-500317 A | 1/2014 |
| JP | 2018-500304 A | 1/2018 |

(Continued)

OTHER PUBLICATIONS

STNext Accession No. 1997:727377 to Kaminsky (Year: 1997).*
Int'l Search Report and Written Opinion mailed Jul. 8, 2020 in Int'l Application No. PCT/CN2020/085713.
International Search Report and Written Opinion issued Mar. 31, 2023 in SG Application No. 11202111502X.
Ballatore et al., "Carboxylic Acid (Bio)Isosteres in Drug Design," ChemMedChem, vol. 8(3), pp. 385-395 (2013).

(Continued)

*Primary Examiner* — Jean P Cornet
(74) *Attorney, Agent, or Firm* — Panitch Schwarze Belisario & Nadel LLP

(57) ABSTRACT

An FXR small molecule agonist and a preparation method therefor and a use thereof, having a structure as shown in formula (I). The compound represented by formula (I) has FXR agonistic activity and is capable of preparing drugs for treatment of FXR-related diseases.

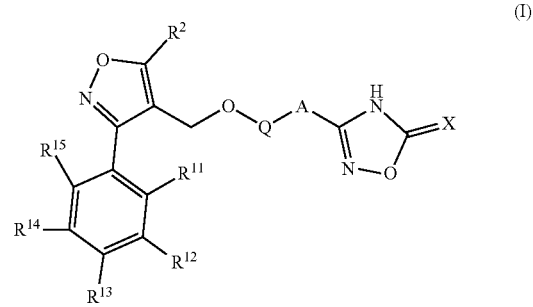

15 Claims, 4 Drawing Sheets

(56) References Cited

FOREIGN PATENT DOCUMENTS

| JP | 7398605 B2 | 12/2023 |
|---|---|---|
| WO | 2009012125 A1 | 1/2009 |
| WO | 2012087519 A1 | 6/2012 |
| WO | 2017133521 A1 | 8/2017 |
| WO | 2018039386 A1 | 3/2018 |
| WO | 2018085148 A1 | 5/2018 |
| WO | 2019007418 A1 | 1/2019 |
| WO | 2020011146 A1 | 1/2020 |
| WO | 2020114307 A1 | 6/2020 |
| WO | 2020156241 A1 | 8/2020 |
| WO | 2020211872 A1 | 10/2020 |

OTHER PUBLICATIONS

International Search Report issued Jan. 7, 2020 in PCT/CN2021/121313.
Meanwell, N., "Synopsis of Some Recent Tactical Application of Bioisosteres in Drug Design," Journal of Medicinal Chemistry, vol. 54, pp. 2529-2591 (2011).
Office Action issued Mar. 11, 2024 in JP Application No. 2023-519904.
Office Action issued Apr. 19, 2022 in Indian Application No. 202137052539.
European Extended Search Report issued on Nov. 15, 2022, in corresponding EP Application 20791301.3.

* cited by examiner

FXR SMALL MOLECULE AGONIST AND PREPARATION METHOD THEREFOR AND USE THEREOF

CROSS-REFERENCE TO RELATED APPLICATIONS

This application is a Section 371 of International Application No. PCT/CN2020/085713, filed Apr. 20, 2020, which was published in the Chinese language on Oct. 22, 2020 under International Publication No. WO 2020/211872 A1, which claims priority under 35 U.S.C. § 119(b) to Chinese Application No. 201910319757.X, filed on Apr. 19, 2019 and Chinese Application No. 201910969552.6, filed on Oct. 12, 2019, the disclosures of which are incorporated herein by reference in their entireties.

TECHNICAL FIELD

The present invention relates to the field of medicine, and relates to a class of compounds as FXR agonist and preparation therefor and use thereof. Specifically, it relates to a class of non-steroidal compounds that can be used as FXR agonist and the enantiomer, diastereomer, tautomer, solvate, prodrug, or pharmaceutically acceptable salt thereof, the preparation method therefor and use thereof in the manufacture of a medicament for the treatment of FXR-related disease.

BACKGROUND TECHNIQUE

Nuclear receptors are widely present in organisms and are a type of nuclear transcription regulators that rely on specific ligand activation. Metabolic nuclear receptors are a type of nuclear receptors that regulate substance metabolism, cell proliferation, and apoptosis in the body. Farnesoid X receptor (FXR) is a member of the nuclear receptor superfamily, which was first discovered by Foman et al. in 1995 and named because its transcriptional activity can be enhanced by farnesoid.

The FXR structure contains ligand-independent transcription activation function domain (AF1) at amino-terminal, DNA binding domain (DBD), hinge region, ligand binding domain (LBD) and ligand-dependent transcription activation function domain (AF2) at carbon-terminal, which is a typical nuclear receptor structure. FXR is activated by bile acids in the body and participates in the processes of bile acid metabolism, lipid metabolism, and sugar metabolism in the living body. The mechanism by which FXR regulates bile acid metabolism and transport is mainly accomplished by regulating the transcription of cholesterol 7α-hydroxylase (CYP7A1) which is a rate-limiting enzyme of bile acid synthesis. Although FXR cannot directly act on the CYP7A1 promoter, it can induce the expression of small heterodimer partner (SHP) and combine HNF-4α (hepatocyte nuclear factor 4a) and LRH-1 (liver receptor homolog) to down-regulate the transcription of CYP7A1. In the process of lipid metabolism, FXR in the liver regulates lipid metabolism and transport to reduce plasma free fatty acids and triglycerides by directly or indirectly regulating PPARα, VLDL receptor (very low density lipoprotein receptor, VLDLR), proprotein convertase subtilisin kexin type 9 (PCSK9), scavenger receptor group B type 1 (SRB1), phosphor lipid transfer protein (PLTP), liver X receptor (LXR), sterol regulatory element-binding protein-1C (SREBP-1C) and fatty acid synthetase (FAS), and activating lipoprotein lipase (LPL) and the like. In the process of glucose metabolism, the activation of FXR can promote liver glycogen synthesis and increase insulin sensitivity and insulin secretion to control blood glucose levels in the body. Since FXR plays an important role in the processes of bile acid metabolism, lipid metabolism and glucose metabolism, FXR ligand small molecule compounds are expected to be used as new medicament for the treatment of hypertriglyceridemia, type 2 diabetes, metabolic syndrome, NAFLD and other metabolic-related diseases.

SUMMARY OF THE INVENTION

The object of the present invention is to provide a FXR small molecule agonist and preparation method therefor and use thereof.

In the first aspect of the present invention, it provides a compound represented by general formula I, or enantiomer, diastereomer, tautomer, racemate, solvate, prodrug or pharmaceutically acceptable salt thereof,

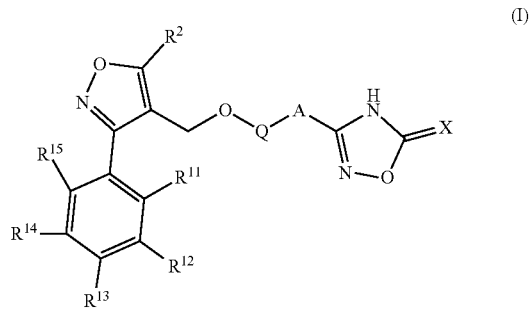

(I)

wherein, $R^{11}$, $R^{12}$, $R^{13}$, $R^{14}$ and $R^{15}$ are each independently hydrogen, halogen, halogenated $C_{1-6}$ alkyl, halogenated $C_1$-$C_6$ alkoxy, $C_1$-$C_6$ alkyl, $C_{1-6}$ alkoxy, $C_3$-$C_6$ cycloalkyl, $C_3$-$C_6$ cycloalkoxy, cyano or nitro;

$R^2$ is $C_6$-$C_6$ aryl, $C_1$-$C_6$ alkyl or $C_3$-$C_6$ cycloalkyl;

Q is a 4-8 membered heterocyclyl;

A is the following substituted or unsubstituted group: phenyl, pyridyl, thienyl, furyl, indazolyl, indolyl, benzothienyl, benzofuranyl, and the "substituted" means that there is one, two or three substituents selected from the group consisting of halogen, $C_1$-$C_6$ alkyl, halogenated $C_{1-6}$ alkyl, halogenated $C_1$-$C_6$ alkoxy, $C_3$-$C_6$ cycloalkyl, $C_1$-$C_6$ alkoxy, and $C_3$-$C_6$ cycloalkoxy;

X is O or S.

In another preferred example, $R^{11}$, $R^{12}$, $R^{13}$, $R^{14}$ and $R^{15}$ are each independently hydrogen, fluorine, chlorine, bromine, methyl, ethyl, n-propyl, isopropyl, n-butyl, isobutyl, trifluoromethyl, or trifluoromethoxy.

In another preferred example, $R^{12}$, $R^{13}$ and $R^{14}$ are hydrogen.

In another preferred example, $R^{11}$ and $R^{15}$ are each independently hydrogen, chlorine, bromine, trifluoromethyl, or trifluoromethoxy.

In another preferred example, $R^2$ is phenyl, methyl, ethyl, n-propyl, isopropyl, n-butyl, isobutyl, cyclopropyl, cyclobutyl or cyclopentyl.

In another preferred example, Q is a 4-8 membered nitrogen-containing heterocyclyl or a 4-7 membered nitrogen-containing heterocyclyl.

In another preferred example, Q is

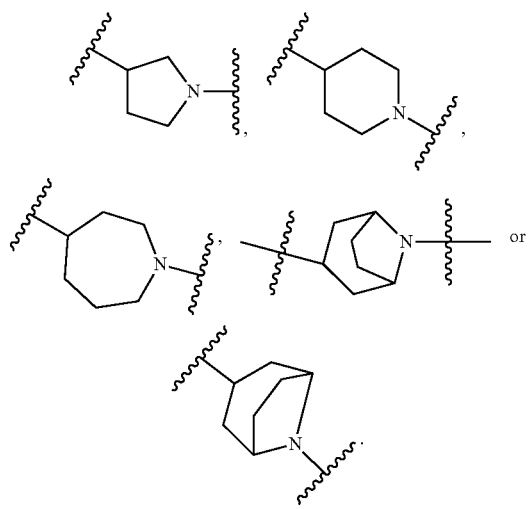

In another preferred example, A is the following substituted or unsubstituted group: phenyl, pyridyl, thienyl, furyl, indazolyl, indolyl, benzothienyl, benzofuranyl, and the "substituted" means that there is one or two substituents selected from the group consisting of fluorine, chlorine, bromine, $C_1$-$C_4$ alkyl, $C_3$-$C_6$ cycloalkyl, $C_1$-$C_4$ alkoxy, and $C_3$-$C_6$ cycloalkoxy.

In another preferred example, A is the following substituted or unsubstituted group: phenyl, pyridyl, thienyl, furyl, indazolyl, indolyl, benzothienyl, benzofuranyl, and preferably, A is the following substituted or unsubstituted group: phenyl, pyridyl, indolyl, and the "substituted" means that there is one or two substituents selected from the group consisting of fluorine, chlorine, bromine, trifluoromethyl, trifluoromethoxy, methyl, ethyl and propyl.

In the present invention, when there are two or more substituents, each substituent is the same or different.

In another preferred example, A is

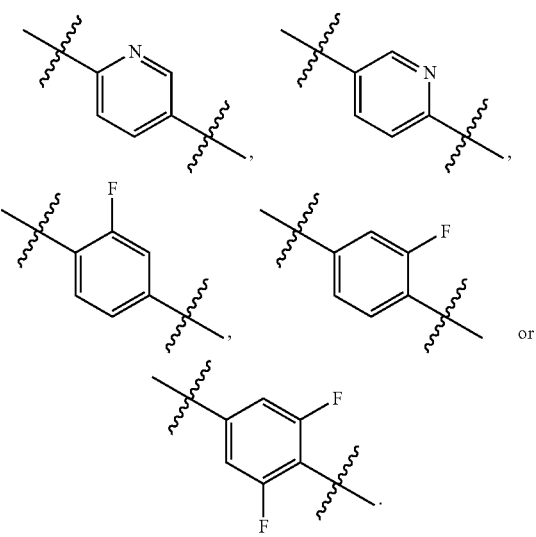

In another preferred example, the pharmaceutically acceptable salt in the present invention refers to a salt formed from inorganic acid such as phosphoric acid, sulfuric acid, hydrochloric acid, etc., or from organic acid such as acetic acid, tartaric acid, citric acid, malic acid, etc., or from acidic amino acid such as aspartic acid, glutamic acid, etc.; or a salt formed from inorganic base, such as sodium, potassium, calcium, aluminum and ammonium salts.

In another preferred example, the compound is:

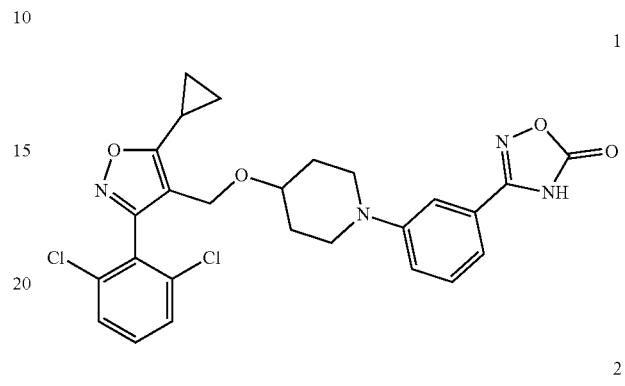

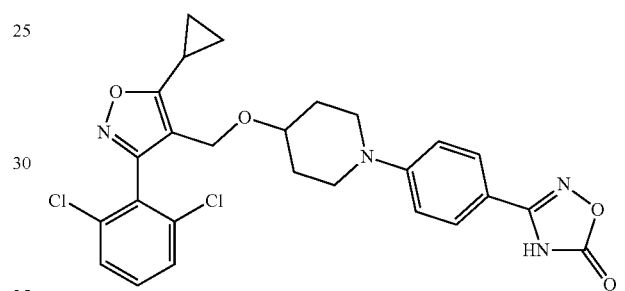

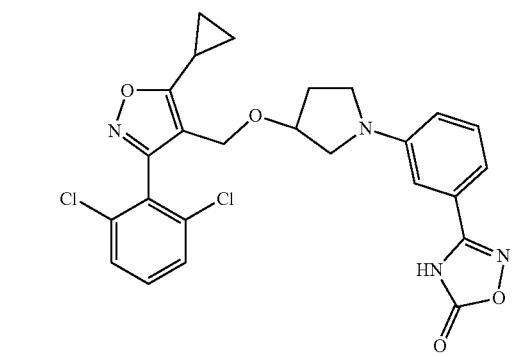
5
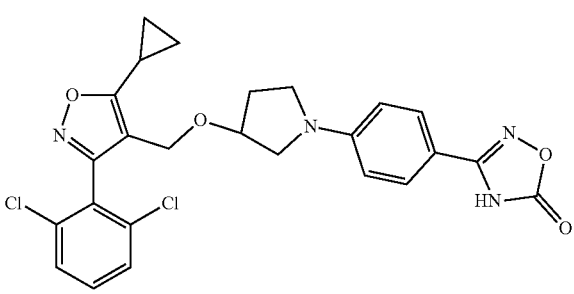
6
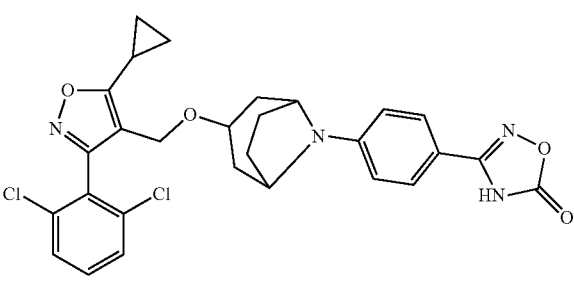
7
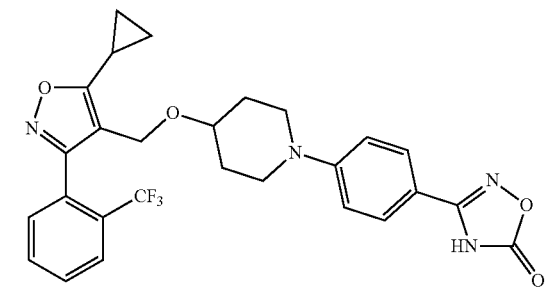
8
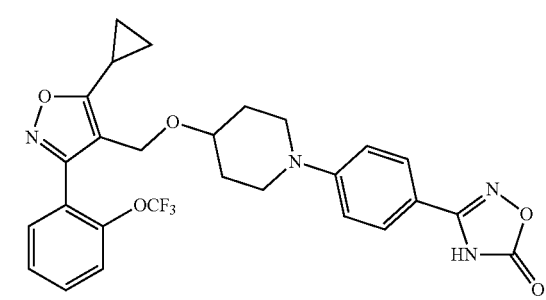
9
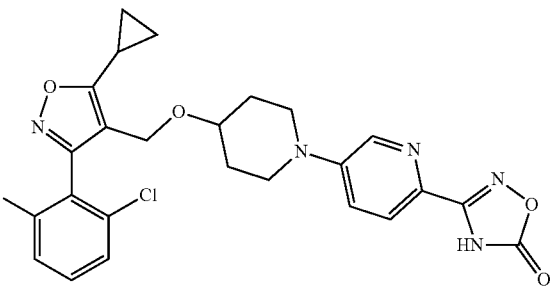
10
11
12
13
14

15
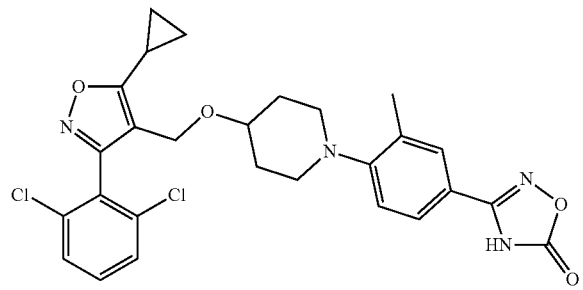
16
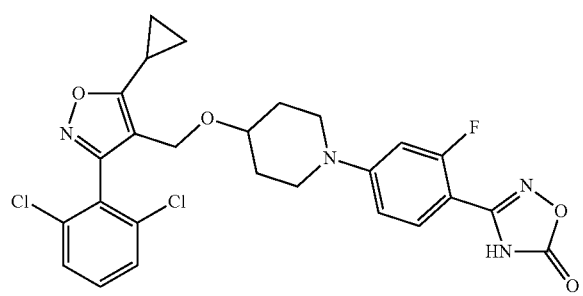
17
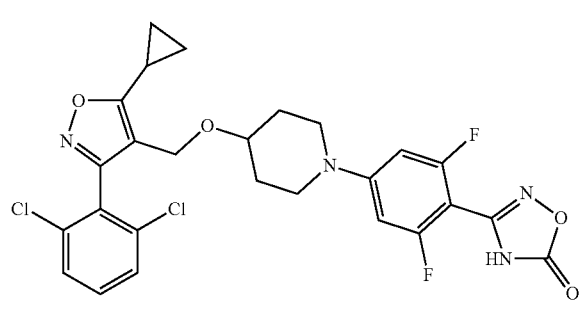
18
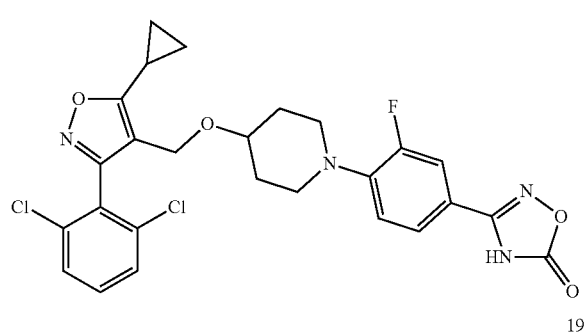
19
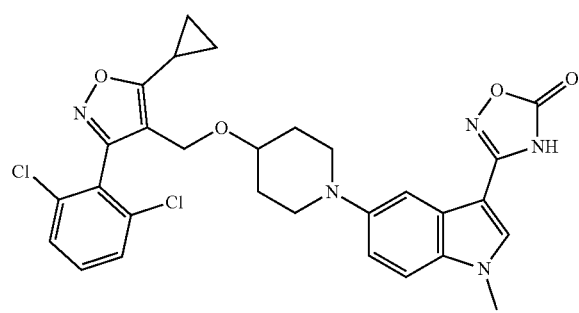
20
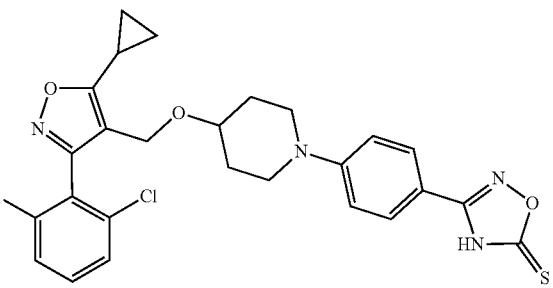
21
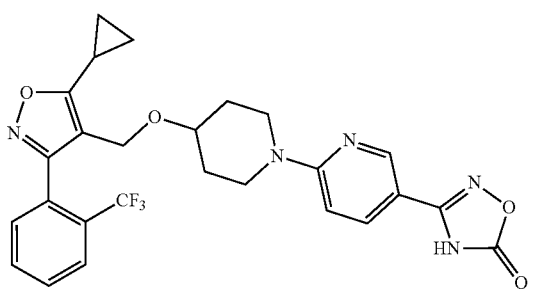
22
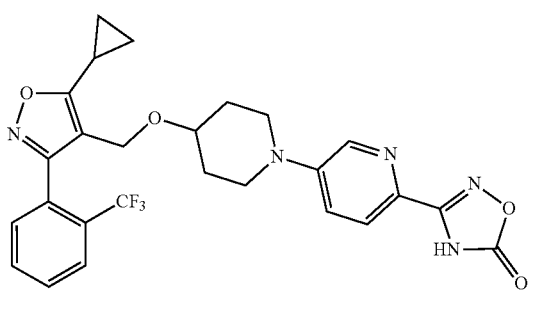
23
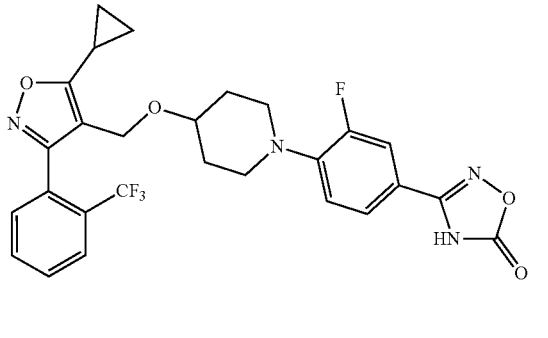
24
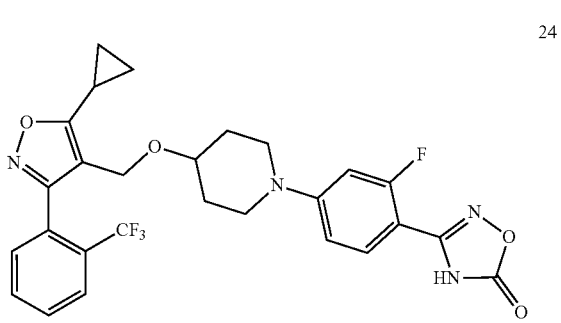

25
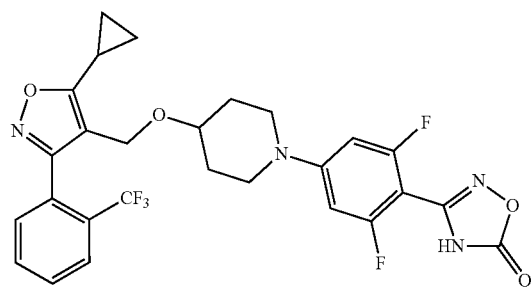
26
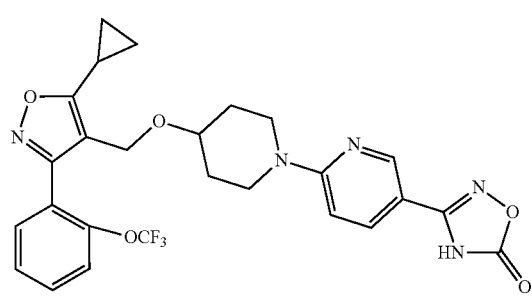
27
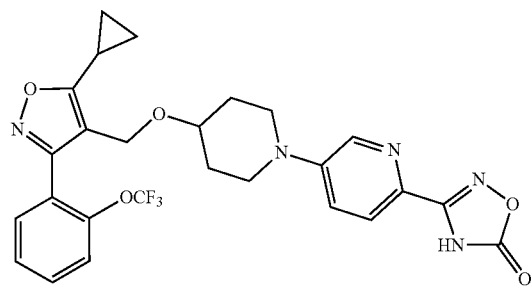
28
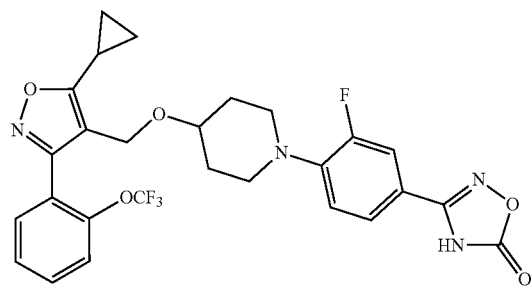
29
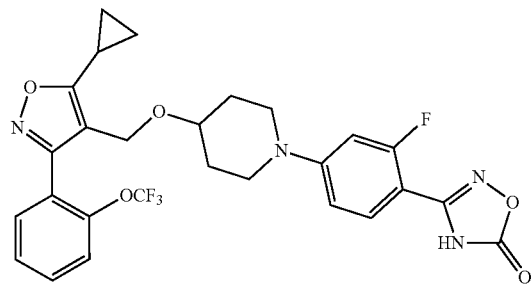
30
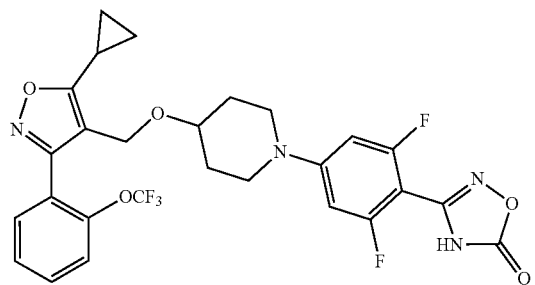
31
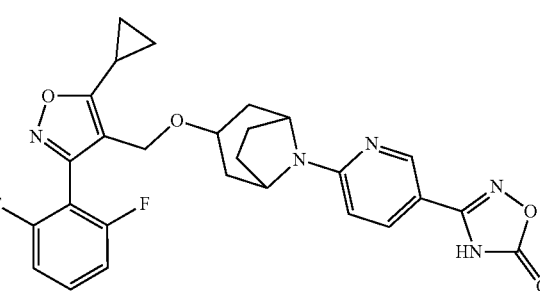
32
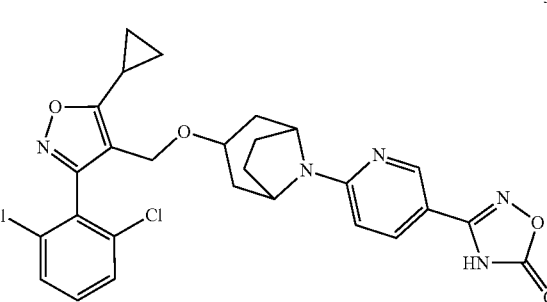
33
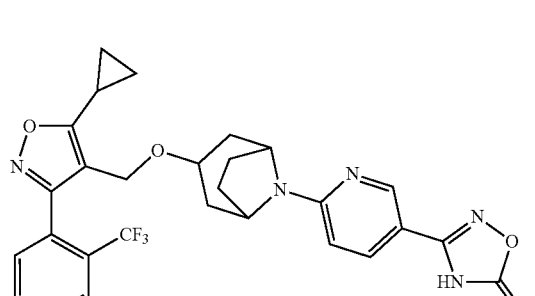
34
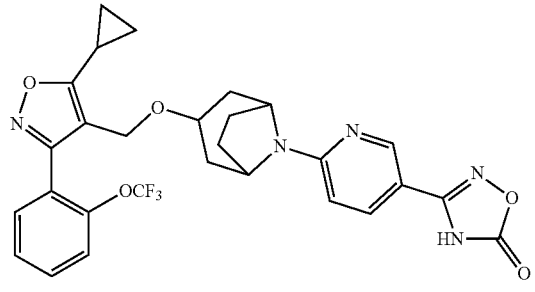

35

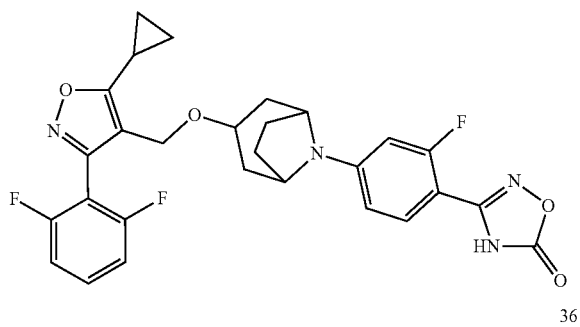

36

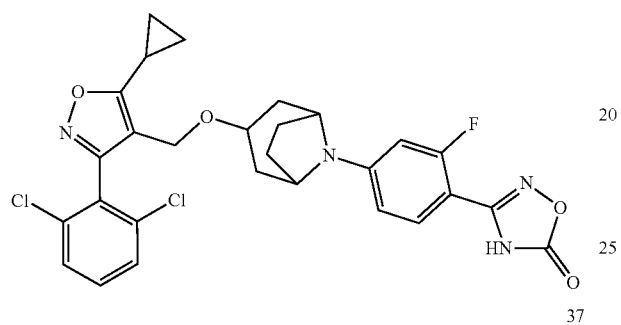

37

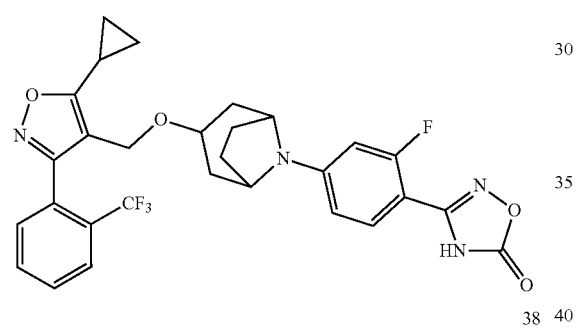

38

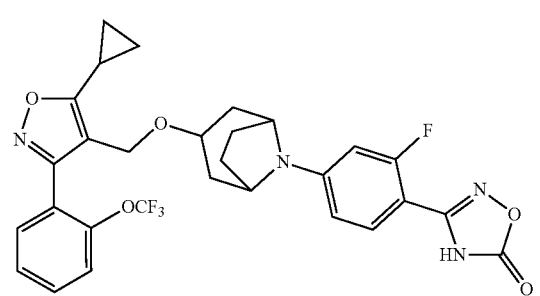

39

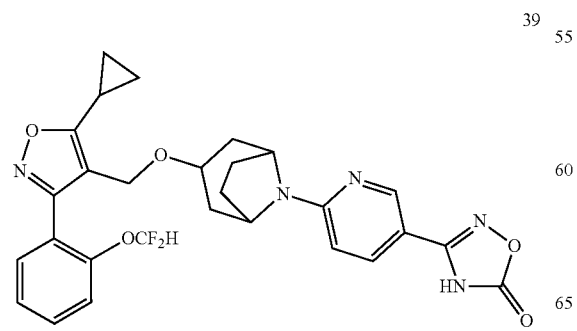

40

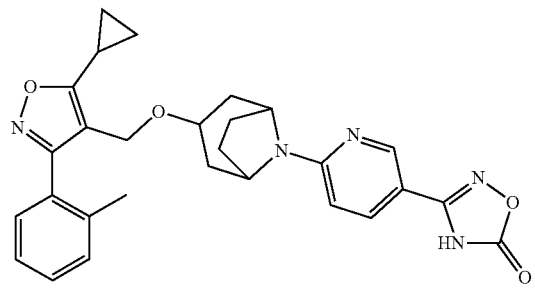

41

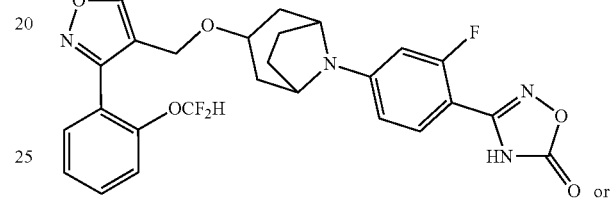

or

42

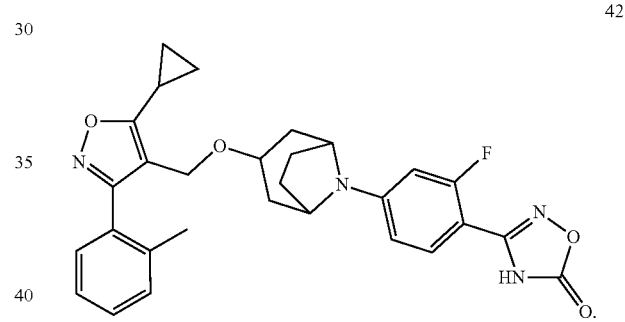

The compound of the present invention has an asymmetric center, a chiral axis, and a chiral plane, and can exist in the form of racemate, R-isomer, or S-isomer. Those skilled in the art can use conventional technical means to obtain R-isomer and/or S-isomer from racemate resolution.

In the second aspect of the present invention, it provides a method for preparing the compound according to the first aspect, which includes the following steps:

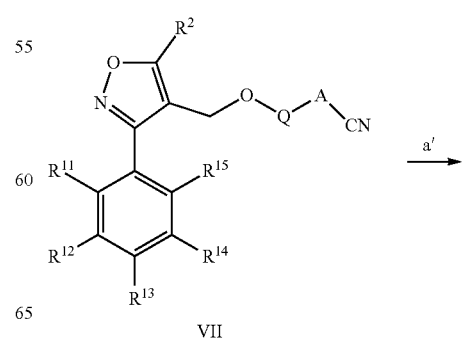

VII

-continued

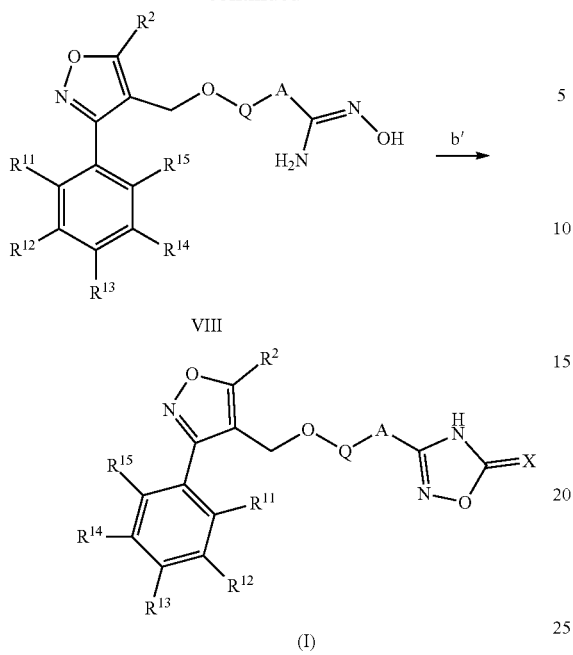

(a') reacting a compound represented by general formula VII with hydroxylamine hydrochloride to produce a compound represented by general formula VIII;

(b') reacting the compound represented by the general formula VIII under the action of phosgene, triphosgene, carbonyldiimidazole or thiocarbonyldiimidazole to produce the compound represented by the general formula I, wherein, the definitions of X, $R^2$, Q, A, $R^{11}$, $R^{12}$, $R^{13}$, $R^{14}$ and $R^{15}$ are described as above.

In another preferred example, the compound represented by general formula VII is prepared by the following steps:

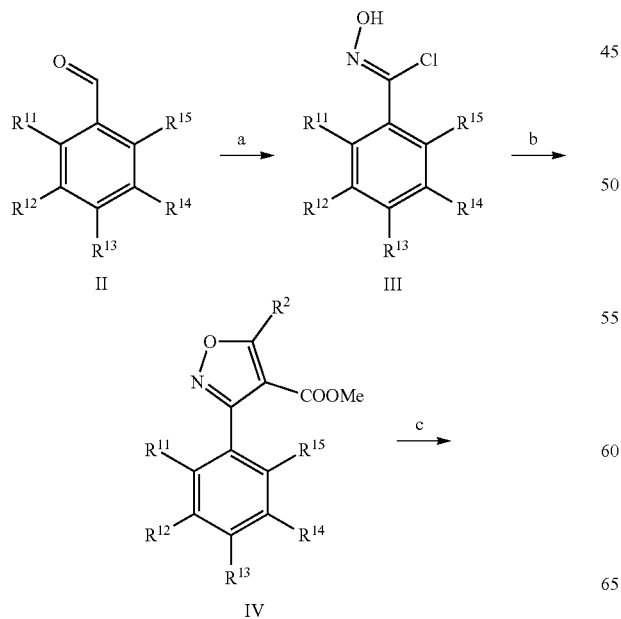

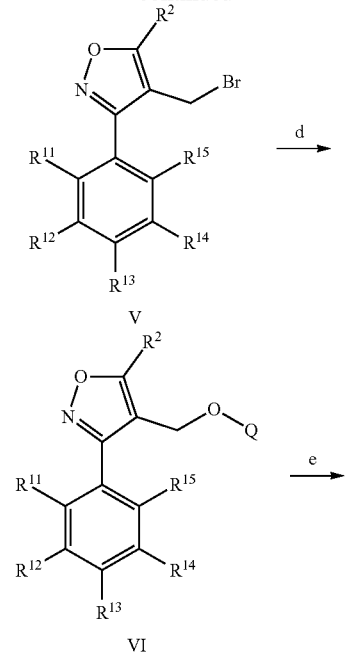

a) reacting substituted benzaldehyde compound represented by general formula II as starting materials with hydroxylamine hydrochloride to obtain an intermediate and then chlorinating the intermediate with N-chlorosuccinimide (NCS) to produce a compound represented by general formula III;

b) reacting the compound represented by the general formula III with 3-oxopropionate to obtain a compound represented by the general formula IV;

c) reducing the ester in the compound represented by formula IV to produce alcohol, and then brominating to produce a compound represented by V;

d) reacting the compound represented by general formula V with Q-OH to produce a compound represented by general formula VI;

e) coupling the compound represented by general formula VI with Br-A-CN under the catalysis of copper or palladium to obtain the compound represented by general formula VII, in each formula, the definitions of $R^2$, Q, A, $R^{11}$, $R^{12}$, $R^{13}$, $R^{14}$ and $R^{15}$ are described as above.

In another preferred example, the compound represented by general formula VII is prepared by the following steps:

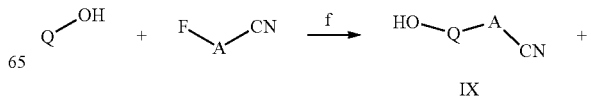

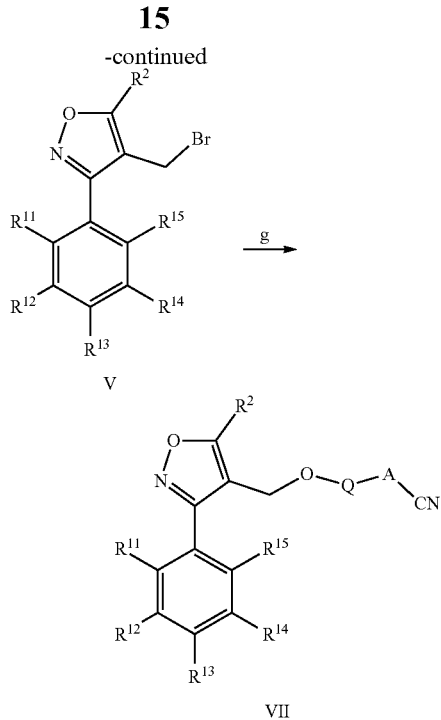

f) reacting Q-OH with F-A-CN to generate a compound represented by general formula IX;
g) reacting a compound represented by the general formula V with the compound represented by the general formula IX to produce the compound represented by the general formula VII,
in each formula, $R^2$, Q, A, $R^{11}$, $R^{12}$, $R^{13}$, $R^{14}$ and $R^{15}$ are defined as above.

In the third aspect of the present invention, it provides a pharmaceutical composition, comprising:
the compound represented by the general formula I according to the first aspect, or the enantiomer, diastereomer, tautomer, racemate, solvate, prodrug, or pharmaceutically acceptable salt thereof; and
a pharmaceutically acceptable carrier.

The compound provided by the present invention can be used alone or mixed with pharmaceutically acceptable auxiliary material (such as excipient, diluent, etc.) to prepare tablet, capsule, granule or syrup for oral administration. The pharmaceutical composition can be prepared according to conventional methods in pharmacy.

In the fourth aspect of the present invention, it provides use of the compound represented by the general formula I according to the first aspect, or the enantiomer, diastereomer, tautomer, racemate, solvate, prodrug, or pharmaceutically acceptable salt thereof.
(a) as an FXR agonist;
(b) for the manufacture of a medicament for the treatment of FXR-related diseases;
(c) to reduce the levels of ALP, ALT, AST and TBA in serum;
(d) to reduce the amount of hydroxyproline in liver tissue;
(e) to down-regulate the expression of α-SMA and Col1α1 mRNA in liver tissue; or
(f) to reduce the content of collagen in the liver.

In another preferred example, the FXR-related disease is a disease related to bile acid metabolism, carbohydrate metabolism, lipid metabolism, inflammation, and/or liver fibrosis.

In another preferred example, the FXR-related disease is non-alcoholic fatty liver (NASH), primary biliary cirrhosis (PBC), primary sclerosing cholangitis (PSC), gallstone, non-alcoholic liver cirrhosis, liver fibrosis, cholestatic liver disease, hyperlipidemia, hypercholesterolemia, or diabetes.

It should be understood that, within the scope of the present invention, each of the above technical features of the present invention and each of the technical features specifically described below (e.g., examples) can be combined with each other, thereby forming a new or preferred technical solution. Each feature disclosed in the specification can be replaced by any alternative feature that provides the same, equal or similar purpose. Due to space limitations, they will not be redundantly described herein.

DETAILED DESCRIPTION

Figure 1:
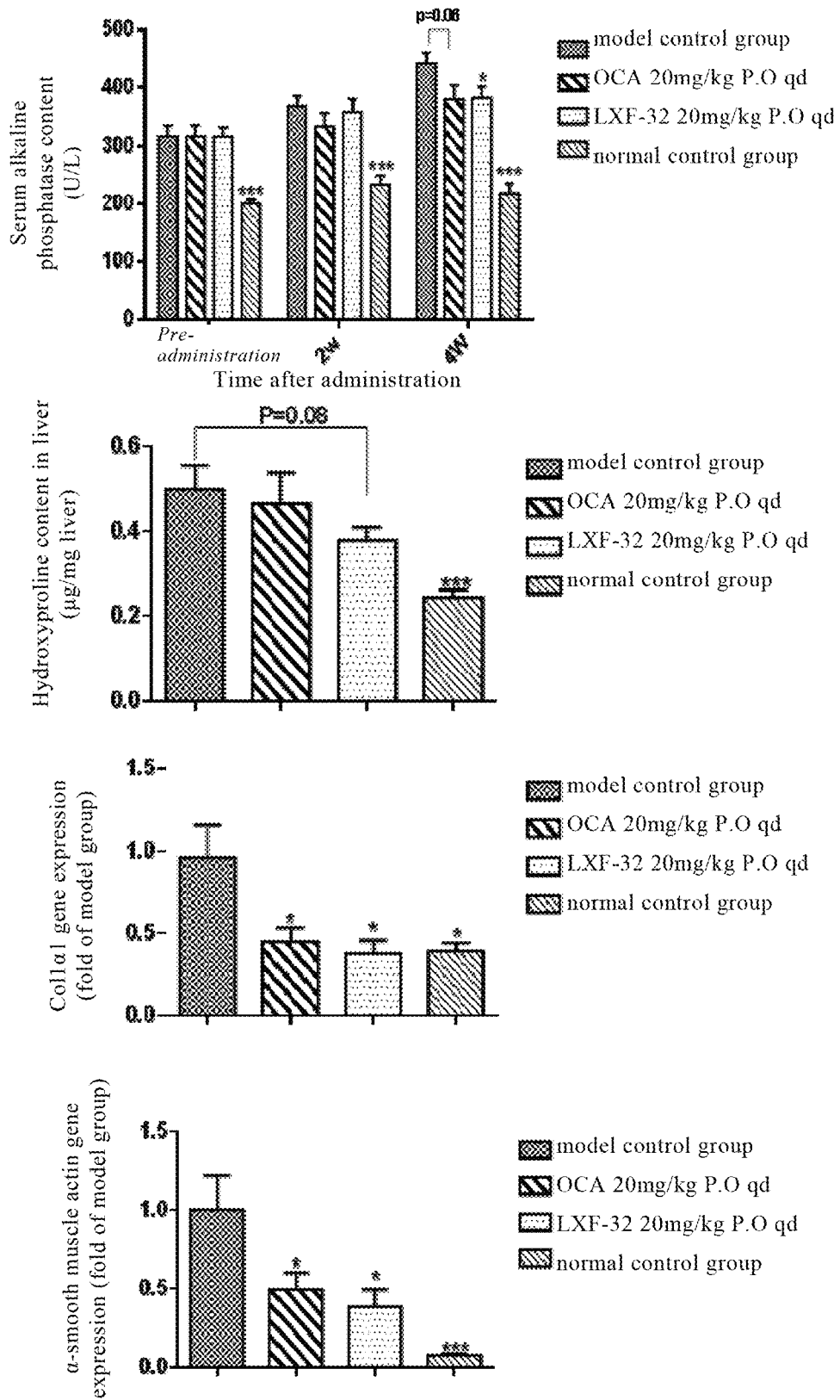
FIG. 1 shows the effect of compound 1 administered for 4 weeks on ALP in serum, hydroxyproline in liver, α-SMA and Col1α1 mRNA in liver, *P<0.05, P<0.01, *P<0.001, compared with the model control group (vehicle group).

After extensive and intensive researches, the inventors of the present application developed a class of non-steroidal compounds that can be used as FXR agonist, which have the ability to agonize FXR at the molecular and cellular levels. Studies have shown that the compounds of the present application can reduce ALP. ALT, AST, and TBA levels in serum, reduce the amount of hydroxyproline in the liver tissue, down-regulate the expression of α-SMA and Col1α1 mRNA in the liver tissue, and reduce the content of collagen in the liver. The compound of the present invention has the advantages of high FXR agonistic activity, simple synthesis, easy availability of raw materials, etc., and can be used for the manufacture of a medicament for treating FXR-related diseases. On this basis, the present invention has been completed.

Terms

In the present invention, the halogen is F, Cl, Br or I.

In the present invention, unless otherwise specified, the terms used have the general meanings known to those skilled in the art.

In the present invention, the term "$C_1$-$C_6$" refers to 1, 2, 3, 4, 5 or 6 carbon atoms, and "$C_1$-$C_8$" refers to 1, 2, 3, 4, 5, 6, 7 or 8 carbon atoms, and so on. "3-10 membered" refers to 3-10 ring atoms, and so on.

In the present invention, the term "alkyl" refers to a saturated linear or branched hydrocarbon moiety. For example, the term "$C_1$-$C_6$ alkyl" refers to a straight or branched chain alkyl having 1 to 6 carbon atoms, including but not limited to methyl, ethyl, n-propyl, isopropyl, n-butyl, isobutyl, sec-butyl, tert-butyl, pentyl and hexyl, etc.; preferably ethyl, n-propyl, isopropyl, n-butyl, isobutyl, sec-butyl and tert-butyl.

In the present invention, the term "alkoxy" means —O—($C_1$-$C_6$ alkyl) group. For example, the term "$C_1$-$C_6$ alkoxy" refers to a straight or branched chain alkoxy having 1 to 6 carbon atoms, including but not limited to methoxy, ethoxy, n-propoxy, isopropoxy, butoxy and so on.

In the present invention, the term "cycloalkyl" refers to a saturated cyclic hydrocarbon moiety, for example, the term "$C_3$-$C_{10}$ cycloalkyl" refers to a cyclic alkyl group having 3 to 10 carbon atoms in the ring, including but not limited to cyclopropyl, cyclobutyl, cyclopentyl, cyclohexyl, cycloheptyl, cyclooctyl, cyclodecyl and the like. The terms "$C_3$-$C_8$ cycloalkyl", "$C_3$-$C_7$ cycloalkyl" and "$C_3$-$C_6$ cycloalkyl" have similar meanings.

In the present invention, the term "cycloalkoxy" means cycloalkyl-O—, and cycloalkyl is described as above.

In the present invention, the term "4-7 membered nitrogen-containing heterocyclyl" refers to a cycloalkyl ring having 3-7 ring atoms and containing 1, 2 or 3 N atoms, and includes, but not limited to, azacyclopentane ring, azacyclohexane ring, azacycloheptane ring and the like.

In the present invention, the term "aryl" means a hydrocarbyl moiety containing one or more aromatic rings. For example, the term "$C_6$-$C_{12}$ aryl" refers to an aromatic ring group with 6 to 12 carbon atoms that does not contain heteroatoms in the ring, such as phenyl, naphthyl and the like. The term "$C_6$-$C_{10}$ aryl" has a similar meaning. Examples of aryl include, but are not limited to, phenyl (Ph), naphthyl, pyrenyl, anthracenyl, and phenanthryl.

In the present invention, the term "heteroaryl" means a moiety containing one or more aromatic rings with at least one heteroatom (such as N. O or S), for example, the term "3-12 membered heterocyclyl" means a saturated or unsaturated 3-12 membered ring group containing 1 to 3 heteroatoms selected from oxygen, sulfur and nitrogen on the ring, such as dioxolyl and the like. The term "3-7 membered heterocyclyl" has a similar meaning. Examples of heteroaryl groups include furyl, fluorenyl, pyrrolyl, thienyl, oxazolyl, imidazolyl, thiazolyl, pyridyl, pyrimidinyl, quinazolinyl, quinolinyl, isoquinolinyl, and indolyl.

In the present invention, the term "heterocyclyl" means a cyclic group containing at least one ring heteroatom (such as N, O or S), such as furyl, pyrrolyl, thienyl, oxazolyl, imidazolyl, thiazolyl, pyridyl, quinolinyl, isoquinolinyl, indolyl, pyrimidinyl, tetrahydropyridyl, pyrrolinyl, dihydropyridyl, dihydrofuranyl, dihydrothienyl, pyranyl.

Unless otherwise specified, the alkyl, alkoxy, cycloalkyl, heterocyclyl, and aryl described herein are substituted and unsubstituted groups. Possible substituents on alkyl, alkoxy, cycloalkyl, heterocyclyl and aryl include, but are not limited to: hydroxyl, amino, nitro, cyano, halogen, $C_1$-$C_6$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_6$ alkoxy, aryl, heteroaryl, heteroaryloxy, $C_1$-$C_{10}$ alkylamino, $C_1$-$C_{20}$ dialkylamino, arylamino, diarylamino, $C_1$-$C_{10}$ alkylsulfamoyl, arylsulfamoyl, $C_1$-$C_{10}$ alkylimino, $C_1$-$C_{10}$ alkylsulfoimino, arylsulfoimino, mercapto, $C_1$-$C_{10}$ alkylthio, $C_1$-$C_{10}$ alkylsulfonyl, arylsulfonyl, acylamino, aminoacyl, aminothioacyl, guanidinyl, ureido, cyano, acyl, thioacyl, acyloxy, carboxyl and carboxylate group. On the other hand, cycloalkyl, heterocycloalkyl, heterocycloalkenyl, aryl, and heteroaryl may also be fused to each other.

In the present invention, the substitution is mono-substitution or poly-substitution, and the poly-substitution is di-substitution, tri-substitution, tetra-substitution, or penta-substitution. The di-substitution means that there are two substituents, and so on.

The pharmaceutically acceptable salt of the present invention may be a salt formed by an anion and a positively charged group on the compound of formula I. Suitable anion is chloride, bromide, iodide, sulfate, nitrate, phosphate, citrate, methanesulfonate, trifluoroacetate, acetate, malate, tosylate, tartrate, fumarate, glutamate, glucuronate, lactate, glutarate or maleate ion. Similarly, a salt can be formed from a cation and a negatively charged group on the compound of formula I. Suitable cation includes sodium ion, potassium ion, magnesium ion, calcium ion and ammonium ion, such as tetramethylammonium ion.

In another preferred example, "pharmaceutically acceptable salt" refers to a salt formed by a compound of formula I and an acid selected from the group consisting of hydrofluoric acid, hydrochloric acid, hydrobromic acid, phosphoric acid, acetic acid, oxalic acid, sulfuric acid, nitric acid, methanesulfonic acid, aminosulfonic acid, salicylic acid, trifluoromethanesulfonic acid, naphthalenesulfonic acid, maleic acid, citric acid, acetic acid, lactic acid, tartaric acid, succinic acid, oxalic acid, pyruvic acid, malic acid, glutamic acid, p-toluenesulfonic acid, naphthalenesulfonic acid, ethanesulfonic acid, naphthalenedisulfonic acid, malonic acid, fumaric acid, propionic acid, oxalic acid, trifluoroacetic acid, stearic acid, pamoic acid, hydroxymaleic acid, phenylacetic acid, benzoic acid, glutamic acid, ascorbic acid, p-aminobenzenesulfonic acid, 2-acetoxybenzoic acid and isethionic acid, etc.; or sodium salt, potassium salt, calcium salt, aluminum salt or ammonium salt formed by a compound of formula I and inorganic base; or methylamine salt, ethylamine salt or ethanolamine salt formed by a compound of general formula I and organic base.

Preparation Method

The preparation method of the compound represented by the general formula I of the present invention, the synthetic route is as follows:

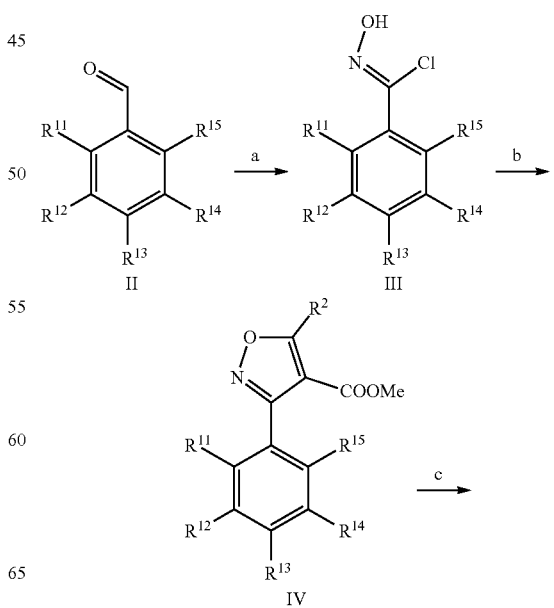

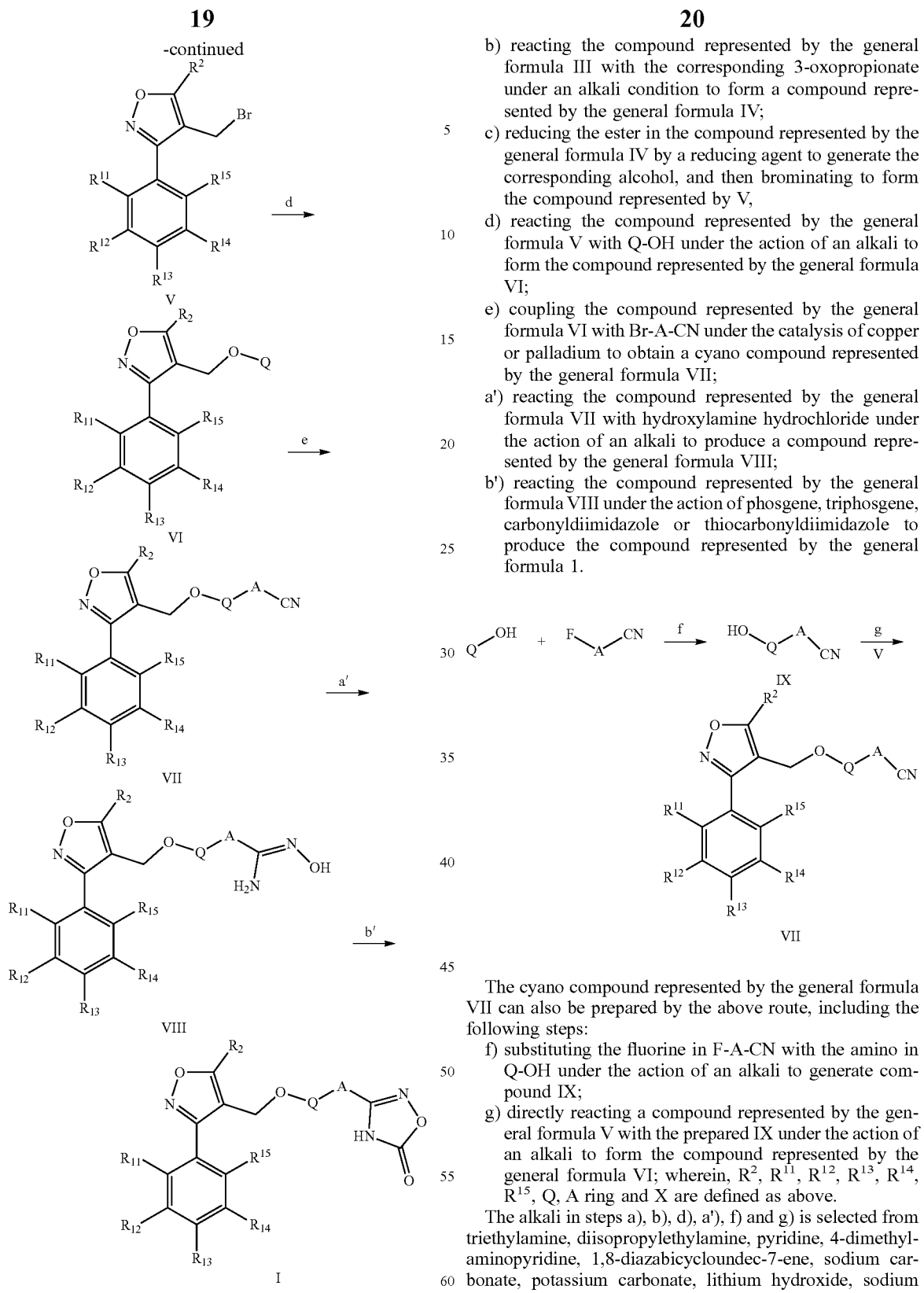

The preparation method includes the following steps:
a) reacting substituted benzaldehyde as a starting material with hydroxylamine hydrochloride under the action of an alkali to obtain an intermediate and then chlorinating with N-chlorosuccinimide (NCS) to form a compound represented by the general formula III;

b) reacting the compound represented by the general formula III with the corresponding 3-oxopropionate under an alkali condition to form a compound represented by the general formula IV;
c) reducing the ester in the compound represented by the general formula IV by a reducing agent to generate the corresponding alcohol, and then brominating to form the compound represented by V;
d) reacting the compound represented by the general formula V with Q-OH under the action of an alkali to form the compound represented by the general formula VI;
e) coupling the compound represented by the general formula VI with Br-A-CN under the catalysis of copper or palladium to obtain a cyano compound represented by the general formula VII;
a') reacting the compound represented by the general formula VII with hydroxylamine hydrochloride under the action of an alkali to produce a compound represented by the general formula VIII;
b') reacting the compound represented by the general formula VIII under the action of phosgene, triphosgene, carbonyldiimidazole or thiocarbonyldiimidazole to produce the compound represented by the general formula 1.

The cyano compound represented by the general formula VII can also be prepared by the above route, including the following steps:
f) substituting the fluorine in F-A-CN with the amino in Q-OH under the action of an alkali to generate compound IX;
g) directly reacting a compound represented by the general formula V with the prepared IX under the action of an alkali to form the compound represented by the general formula VI; wherein, $R^2$, $R^{11}$, $R^{12}$, $R^{13}$, $R^{14}$, $R^{15}$, Q, A ring and X are defined as above.

The alkali in steps a), b), d), a'), f) and g) is selected from triethylamine, diisopropylethylamine, pyridine, 4-dimethylaminopyridine, 1,8-diazabicycloundec-7-ene, sodium carbonate, potassium carbonate, lithium hydroxide, sodium hydroxide, potassium hydroxide, sodium methoxide, sodium ethoxide, potassium ethoxide, potassium tert-butoxide, sodium tert-butoxide, butyl lithium, lithium diisopropylamide.

The alkali in step b) is selected from the group consisting of triethylamine, diisopropylethylamine, pyridine, DBU, sodium carbonate, potassium carbonate, lithium hydroxide, sodium hydroxide, potassium hydroxide, sodium methoxide, sodium ethoxide, and potassium ethoxide.

The reducing agent in step c) is selected from the group consisting of sodium borohydride, sodium triacetoxyborohydride, sodium cyanoborohydride, lithium aluminum hydride, diisopropyl aluminum hydride, and borane.

The copper catalyst in step e) is cuprous iodide, cuprous oxide, and cuprous sulfate; the palladium catalyst is palladium acetate, tetrakis(triphenylphosphine) palladium, bis(acetonitrile) palladium (II) chloride, dichloride palladium, tris(dibenzylideneacetone)dipalladium, bistriphenylphosphorus palladium dichloride, tris(dibenzylideneacetone)dipalladium-chloroform adduct, 1,1'-bis(diphenylphosphino)ferrocene palladium(II) dichloride.

Pharmaceutical Composition

The present invention also provides a pharmaceutical composition, which contains active ingredient in a safe and effective amount, and a pharmaceutically acceptable carrier.

The "active ingredient" in the present invention refers to the compound of formula I in the present invention.

The "active ingredient" and pharmaceutical composition of the present invention are used in the manufacture of a medicament for treating FXR-related diseases. The "active ingredient" and pharmaceutical composition of the present invention can be used as FXR agonist. In another preferred example, it is used in the manufacture of a medicament for preventing and/treating a disease regulated by FXR agonist.

"Safe and effective amount" means that the amount of the active ingredient is sufficient to significantly improve the condition without causing serious side effects. Generally, the pharmaceutical composition contains 1-2000 mg of active ingredient/dose, more preferably, 10-200 mg of active ingredient/dose. Preferably, the "one dose" is a tablet.

"Pharmaceutically acceptable carrier" refers to one or more compatible solid or liquid fillers or gel substances, which are suitable for human use, and must have sufficient purity and sufficiently low toxicity. "Compatibility" herein means that each component in the composition can be blended with each other and can be blended with the active ingredient of the present invention without significantly reducing the efficacy of the active ingredient.

Examples of pharmaceutically acceptable carriers include cellulose and derivatives thereof (such as sodium carboxymethyl cellulose, sodium ethyl cellulose, cellulose acetate, etc.), gelatin, talc, solid lubricant (such as stearic acid, magnesium stearate), calcium sulfate, vegetable oil (such as soybean oil, sesame oil, peanut oil, olive oil, etc.), polyol (such as propylene glycol, glycerin, mannitol, sorbitol, etc.), emulsifier (such as Tween®), Wetting agent (such as sodium lauryl sulfate), coloring agent, flavoring agent, stabilizer, antioxidant, preservative, pyrogen-free water and the like.

The administration method of the active ingredient or the pharmaceutical composition of the present invention is not particularly limited, and representative administration methods include (but are not limited to): oral administration, intratumoral administration, rectal administration, parenteral (intravenous, intramuscular, or subcutaneous) administration and the like.

Solid dosage forms for oral administration include capsules, tablets, pills, powders and granules.

Liquid dosage forms for oral administration include pharmaceutically acceptable emulsions, solutions, suspensions, syrups or tinctures. In addition to the active ingredient, the liquid dosage form may contain inert diluents conventionally used in the art, such as water or other solvents, solubilizers and emulsifiers, for example, ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures of these substances. In addition to these inert diluents, the composition may also contain adjuvants such as wetting agents, emulsifying agents and suspending agents, sweetening agents, flavoring agents and perfumes.

In addition to the active ingredient, the suspension may contain suspending agent, for example, ethoxylated isostearyl alcohol, polyoxyethylene sorbitol and dehydrated sorbitan ester, microcrystalline cellulose, aluminum methoxide and agar, or mixtures of these substances, and the like.

The composition for parenteral injection may contain physiologically acceptable sterile aqueous or non-aqueous solutions, dispersions, suspensions or emulsions, and sterile powders for reconstitution into sterile injectable solutions or dispersions. Suitable aqueous and non-aqueous carriers, diluents, solvents or excipients include water, ethanol, polyol and suitable mixtures thereof.

The compound of the present invention can be administered alone or in combination with other therapeutic drugs (such as hypolipidemic drugs).

When the pharmaceutical composition is used, a safe and effective amount of the compound of the present invention is administered to the mammal (such as a human) in need of treatment, wherein the dosage at which the drug is administered is the pharmaceutically effective administration dosage. For a person of 60 kg body weight, the daily dose is usually 1-2000 mg, and 20-500 mg is preferred. Certainly, the specific dosage should be determined by considering factors such as the route of administration, the patient's health status, etc., which are within the skill range of a skilled physician.

The present invention will be further described below in conjunction with specific examples. It should be understood that these examples are only used to illustrate the present invention and not to limit the scope of the present invention. The experimental methods without specific conditions in the following examples generally follow the conventional conditions (eg. the conditions described in Sambrook et al., Molecular Cloning: Laboratory Manual (New York: Cold Spring Harbor Laboratory Press, 1989)) or the conditions recommended by the manufacturer. Unless stated otherwise, percentages and parts are percentages by weight and parts by weight.

Unless otherwise defined, all professional and scientific terms used herein have the same meaning as those familiar to the skilled in the art. In addition, any methods and materials similar to or equivalent to those described can be applied to the method of the present invention. The preferred implementation methods and materials described herein are for demonstration purposes only.

The instruments and main experimental materials used are as follows.

The reagents and anhydrous solvents used were purchased from Chinese commercial companies. Unless otherwise specified, they were used directly. $^1H$ and $^{13}C$ NMR were measured by BrukerAM-400 and Varian Mercury plus-400 nuclear magnetic resonance instruments, and mass spectrometry was measured by Agilent 6230 mass spectrometer and 200-300 mesh of column chromatography silica gel (Qingdao Ocean Chemical Factory), HSGF254 TLC plate (Yantai Chemical Industry Research Institute).

23
Route 1
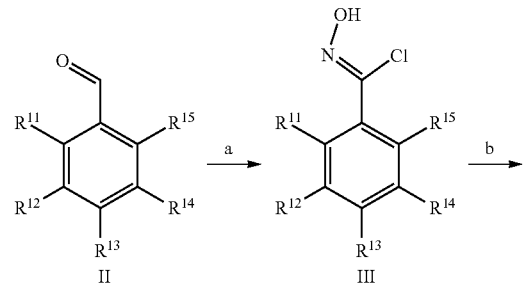
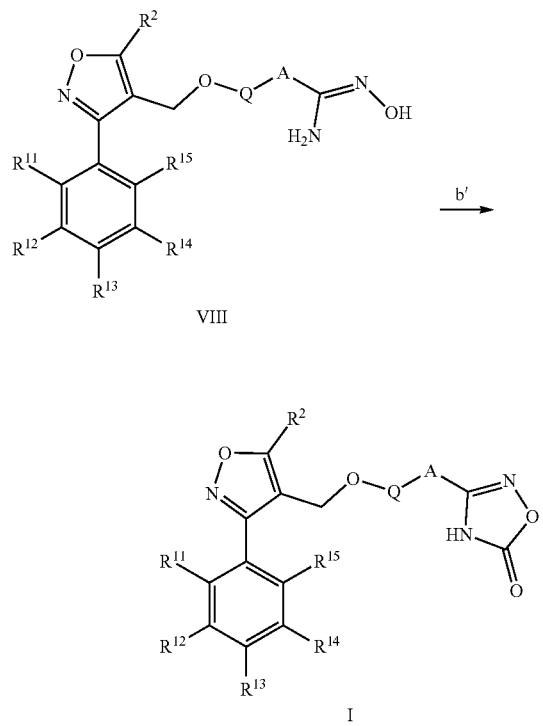
24
-continued
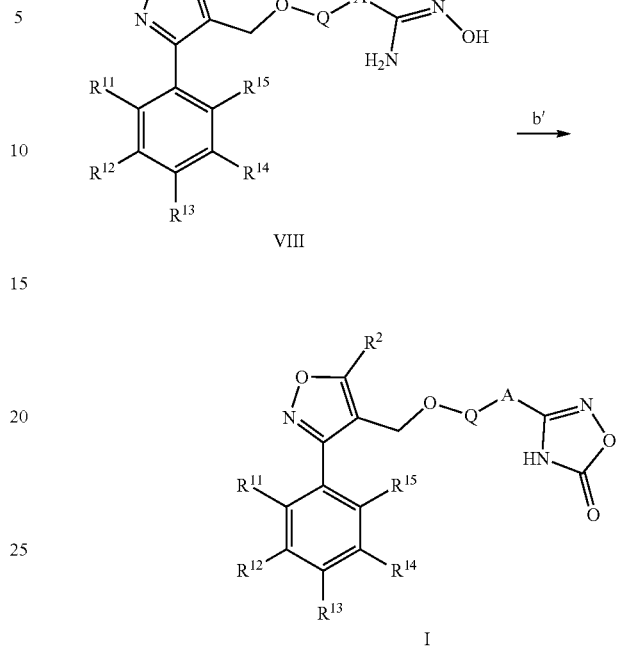
Route 2
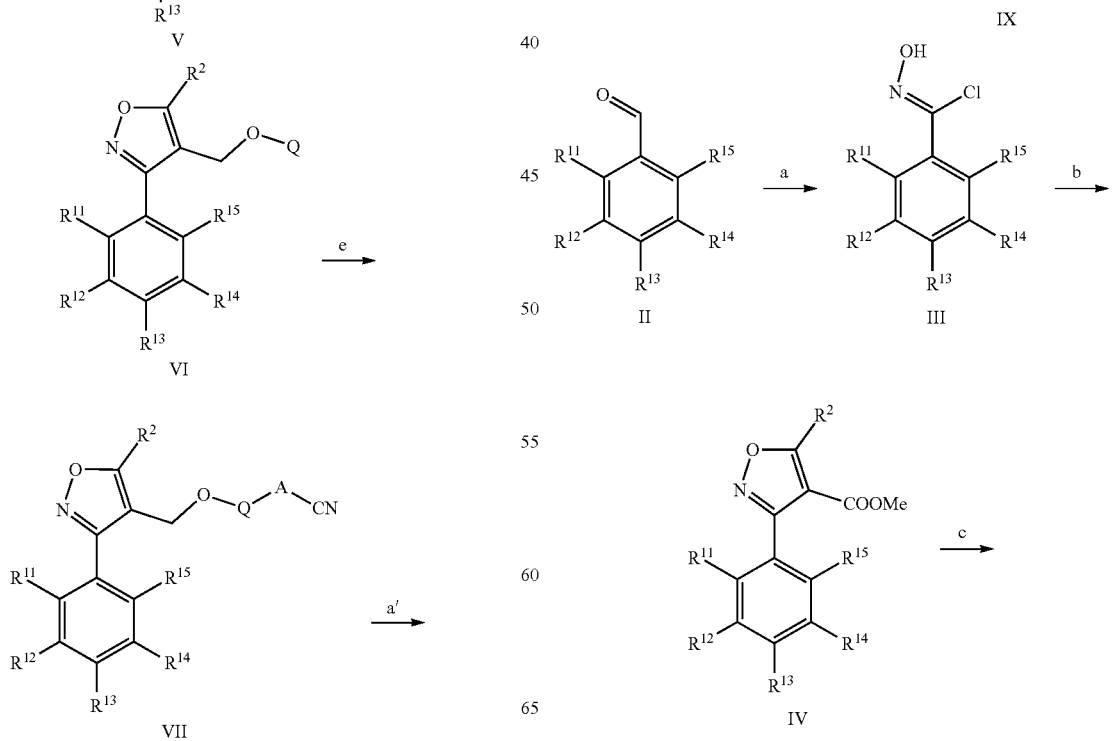

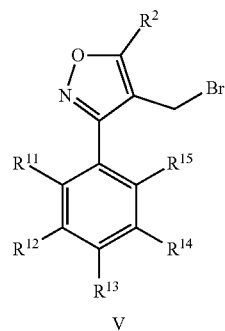
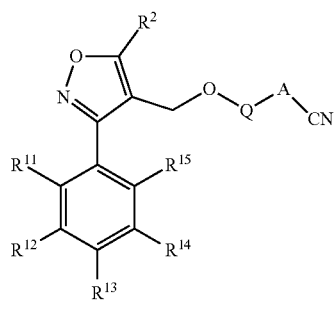
Example 1 LXF-32

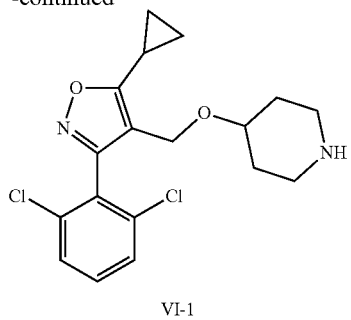

VI-1

At 0° C., aqueous potassium carbonate solution (3 N, 182 mmol) was added dropwise to a stirring solution of hydroxylamine hydrochloride (182 mmol) in ethanol (100 mL), 2,6-dichlorobenzaldehyde (20 g, 114 mmol) was dissolved in 100 ml of ethanol, and then added to the hydroxylamine solution. The temperature was raised to 90° C. and the mixture was reacted for two hours. The mixture was cooled to room temperature and then concentrated to a solid. A water/ethanol (1000 mL/100 mL) solution was added and the solid was stirred to break up, filtered, and dried under vacuum at 50° C. overnight to obtain a compound intermediate (18.4 g). This intermediate was dissolved in N,N-dimethylformamide (50 mL), and added dropwise to N-chlorosuccinimide (97 mmol) solution in N,N-dimethylformamide (100 mL) at 0° C. and stirred overnight. The reaction solution was poured into ice water at 0° C., and then extracted with methyl tert-butyl ether (200 mL each time, 3 times in total), the organic phase was washed with saturated brine, and concentrated to obtain a crude product. N-hexane (600 mL) was added to the flask containing the crude product, stirred with a magnetic stir bar, filter, and the solid was dried under vacuum (30° C.) to obtain intermediate III-1 (18.3 g, yield 73%). $^1$H NMR (400 MH z, CDCl$_3$) δ 67.43-7.39 (m, 2H), 7.39-7.33 (m, 1H).

Triethylamine (8.2 g) was added to methyl 3-cyclopropyl-3-oxopropionate (82 mmol) and stirred for 30 minutes. Then the mixture was cooled to 10° C., and a solution of III-1 (18.3 g, 82 mmol) in absolute ethanol (80 mL) was added dropwise (internal temperature did not exceed 30° C.), and the reaction was kept overnight at room temperature. The reaction solution was diluted by adding ethyl acetate (100 mL), washed with water, and the aqueous phase was extracted with ethyl acetate (100 mL each time, 3 times in total). The organic phases were mixed, washed with saturated brine, and concentrated. 100 mL of ether was added to the concentrate and stirred, and the solvent was removed under vacuum to obtain solid product IV-1 (21.6 g, yield 84%). $^1$H NMR (400 MHz, CDCl$_3$) δ 7.43-7.39 (m, 2H), 7.39-7.33 (m, 1H), 3.72 (s, 3H), 2.21-2.09 (m, 1H), 1.35-1.28 (m, 2H), 1.25-1.18 (m, 2H).

IV-1 (21.6 g, 69 mmol) was dissolved in tetrahydrofuran (140 mL) and cooled to 0° C. A solution of diisobutylaluminum hydride (1.5 M, 102 mL) in toluene was slowly added and the reaction solution is stirred at room temperature for 6 h. The reaction solution was slowly poured into ice water, and 1M aqueous hydrochloric acid solution was added to adjust the pH to about 2. The mixture was extracted with ethyl acetate (100 mL each time, three times in total), concentrated, and subjected to column chromatography to obtain the intermediate alcohol. This intermediate and triphenyl phosphine (59 mmol) were dissolved in dichloromethane (60 mL) and cooled to 0° C. and a solution of carbon tetrabromide (62 mmol) in dichloromethane (60 mL) was added dropwise under the protection of nitrogen and reacted at room temperature for 4 h. The solvent was removed from the reaction solution to obtain an oily substance, which was subjected to column chromatography to obtain intermediate V-1 (15.3 g, yield 96%). $^1$H NMR (400 MHz, CDCl$_3$) δ 7.49-7.44 (m, 2H), 7.43-7.37 (m, 1H), 4.25 (d, J=1.3 Hz, 2H), 2.21-2.09 (m, 1H), 1.35-1.28 (m, 2H), 1.25-1.18 (m, 2H).

At 0° C., potassium tert-butoxide (6.5 mmol) was added to a solution of tert-butyl 4-hydroxypiperidine-1-carboxylate (1.3 g, 6.5 mmol) in anhydrous tetrahydrofuran (20 mL) and stirred for 30 minutes, and then a solution of V-1 (4.3 mmol) in anhydrous tetrahydrofuran (5 mL) was added dropwise, and the reaction was carried out for 8 h. Water (20 mL) was added to the reaction solution, extracted with ethyl acetate (15 mL each time, 3 times in total), the organic phase was washed with saturated brine, concentrated, and subjected to column chromatography to obtain intermediate tert-butyl 4-((5-cyclopropyl)-3-(2,6-dichlorophenyl)isoxazol-4-yl)methoxy)piperidine-1-carboxylate (1.55 g). Intermediate tert-butyl 4-((5-cyclopropyl)-3-(2,6-dichlorophenyl)isoxazol-4-yl)methoxy)piperidine-1-carboxylate (1.55 g, 3.3 mmol) was dissolved in dichloromethane (8 mL) and cooled to 0° C., and trifluoroacetic acid (8 mL) was added dropwise and stirred at room temperature for 3 h. The solvent was removed under vacuum, and the residue was dissolved in ethyl acetate (20 mL), washed with 2 N sodium hydroxide solution, saturated brine, and the solvent was removed to obtain intermediate VI-1 (1.0 g, yield 72%). $^1$H NMR (400 MHz, CDCl$_3$) δ 7.47-7.43 (m, 2H), 7.42-7.36 (m, 1H), 4.23 (s, 2H), 3.55-3.49 (m, 1H), 3.02-2.91 (m, 4H), 2.10-2.02 (m, 1H), 1.93-1.76 (m, 2H), 1.75-1.62 (m, 2H), 1.26-1.06 (m, 4H).

Synthesis of Example Compound 1, Namely LXF-32

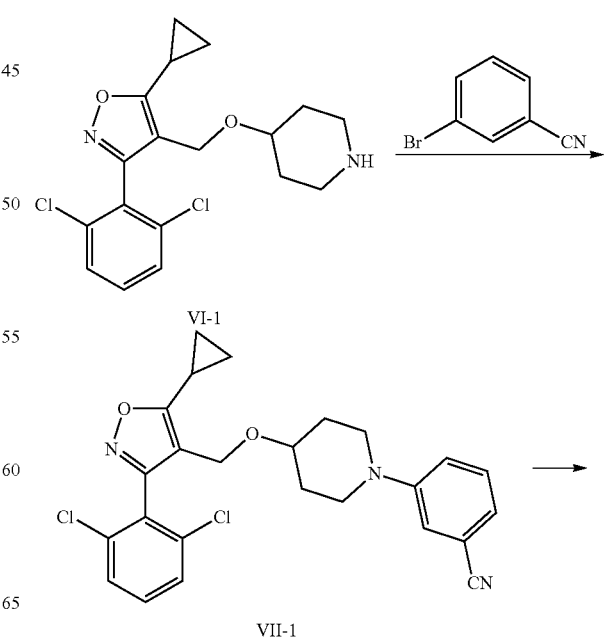

-continued

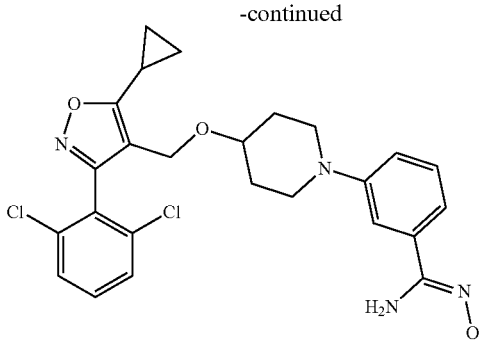

VIII-1

Intermediate VI-1 (1.0 g, 2.7 mmol), 3-bromobenzonitrile (4.1 mmol), sodium tert-butoxide (5.4 mmol), palladium acetate (0.14 mmol), and 1,1'-binaphthalene-2,2'-bisdiphenylphosphine (0.27 mmol) were added to a round bottom flask, and toluene (80 mL) was added under the protection of nitrogen, heated to reflux, and reacted overnight. The reaction solution was cooled to room temperature, and added with water, extracted, concentrated, and subjected to column chromatography to obtain intermediate VII-1 (0.55 g, yield 43%). $^1$H NMR (400 MHz, CDCl$_3$) δ 7.40 (d, J=1.2 Hz, 1H), 7.38 (s, 1H), 7.32-7.28 (m, 2H), 7.09-7.02 (m, 3H), 4.34 (s, 2H), 3.47-3.41 (m, 1H), 3.31-3.20 (m, 2H), 2.97-2.87 (m, 2H), 2.18-2.11 (m, 1H), 1.83-1.72 (m, 2H), 1.26 (qt, J=10.1, 5.1 Hz, 4H), 1.13 (ddd, J=11.4, 7.0, 4.4 Hz, 2H).

VII-1 (0.4 g, 0.9 mmol), hydroxylamine hydrochloride (2.3 mmol), and absolute ethanol (5 mL) were added into a round bottom flask and stirred. Triethylamine (2.3 mmol) was slowly added dropwise, and heated to 80° C. to react for 4 h. After the mixture was cooled to room temperature, the solvent was removed, and the residue was dissolved in ethyl acetate (15 mL), and washed with water and saturated brine. The organic phase was concentrated, and subjected to silica gel column chromatography to obtain intermediate 3-(4-((5-cyclopropyl-3-(2,6-dichlorophenyl)isoxazol-4-yl)methoxy)piperidin-1-yl)-N'-hydroxybenzamidine VIII-1 (0.41 g, yield 96%).

3-(4-((5-cyclopropyl-3-(2,6-dichlorophenyl)isoxazol-4-yl)methoxy)piperidin-1-yl)-N'-hydroxybenzamidine VIII-1 (0.41 g, 0.83 mmol), N,N'-carbonyldiimidazole (1.0 mmol), and 1,4-dioxane (4 mL) were added to a round bottom flask, and then 1,8-diazabicyclo[5.4.0]undec-7-ene (0.91 mmol) was added, heated to 100° C. and reacted for 3 hours. The reaction solution was cooled to room temperature, diluted with water (5 mL), adjusted to pH approximately equal to 2 with a 1M aqueous hydrochloric acid solution, and then extracted with ethyl acetate (4 mL each time, 3 times in total). The organic phases were combined, washed with saturated brine, and concentrated and the crude product obtained was subjected to silica gel column chromatography to obtain the final product 1 (0.28 g, yield 64%). $^1$H NMR (400 MHz, CDCl$_3$) δ 7.37 (d, J=7.5 Hz, 2H), 7.31-7.26 (m, 2H), 7.17 (d, J=10.4 Hz, 2H), 7.07 (d, J=7.5 Hz, 1H), 6.91 (d, J=7.6 Hz, 1H), 4.33 (s, 2H), 3.38 (m, 1H), 3.21 (m, 2H), 2.83 (t, J=8.6 Hz, 2H), 2.15 (m, 1H), 1.73 (m, 2H), 1.51 (m, 2H), 1.26 (m, 4H), 1.13 (m, 2H). MS (ESI, m/z): 541 [M+H]$^+$.

Example 2

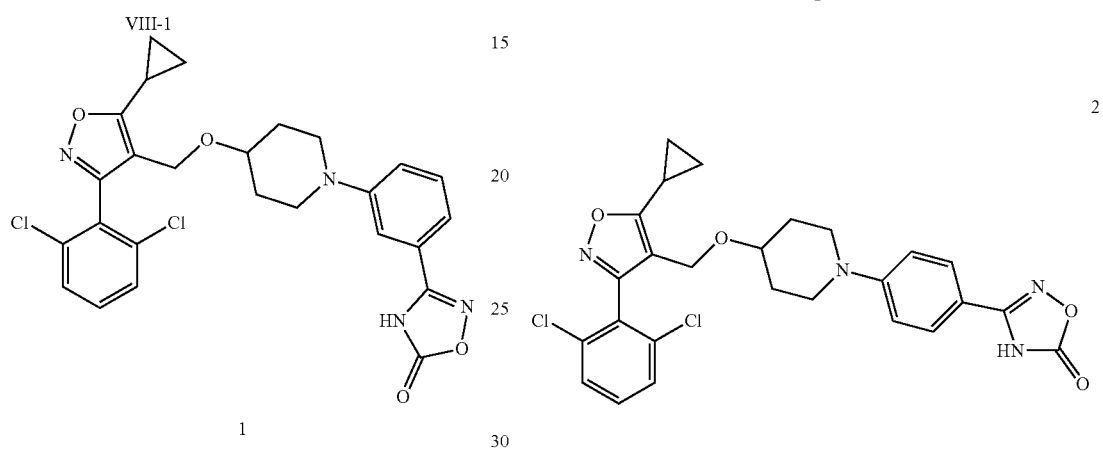

2

Example 2 was carried out by referring to the operation of example 1. The compound was prepared from intermediate VI-1 via route 1. The synthetic route was as follows.

Synthesis of Example Compound 2

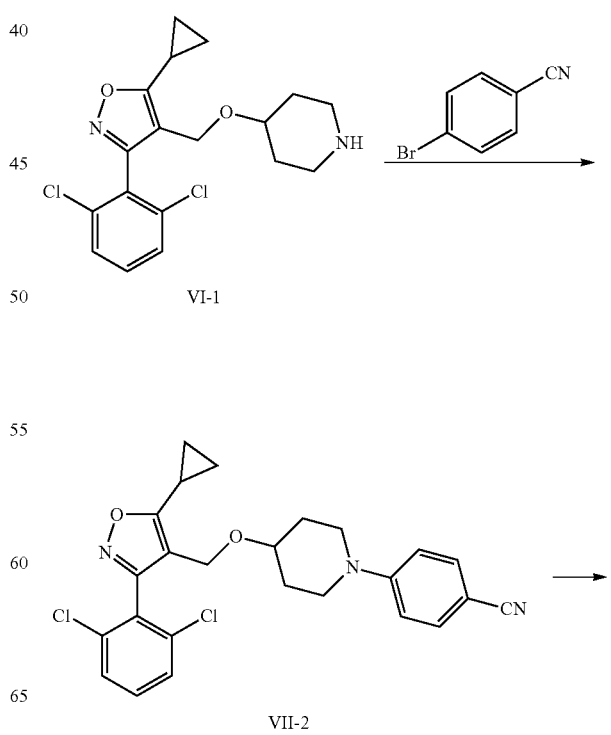

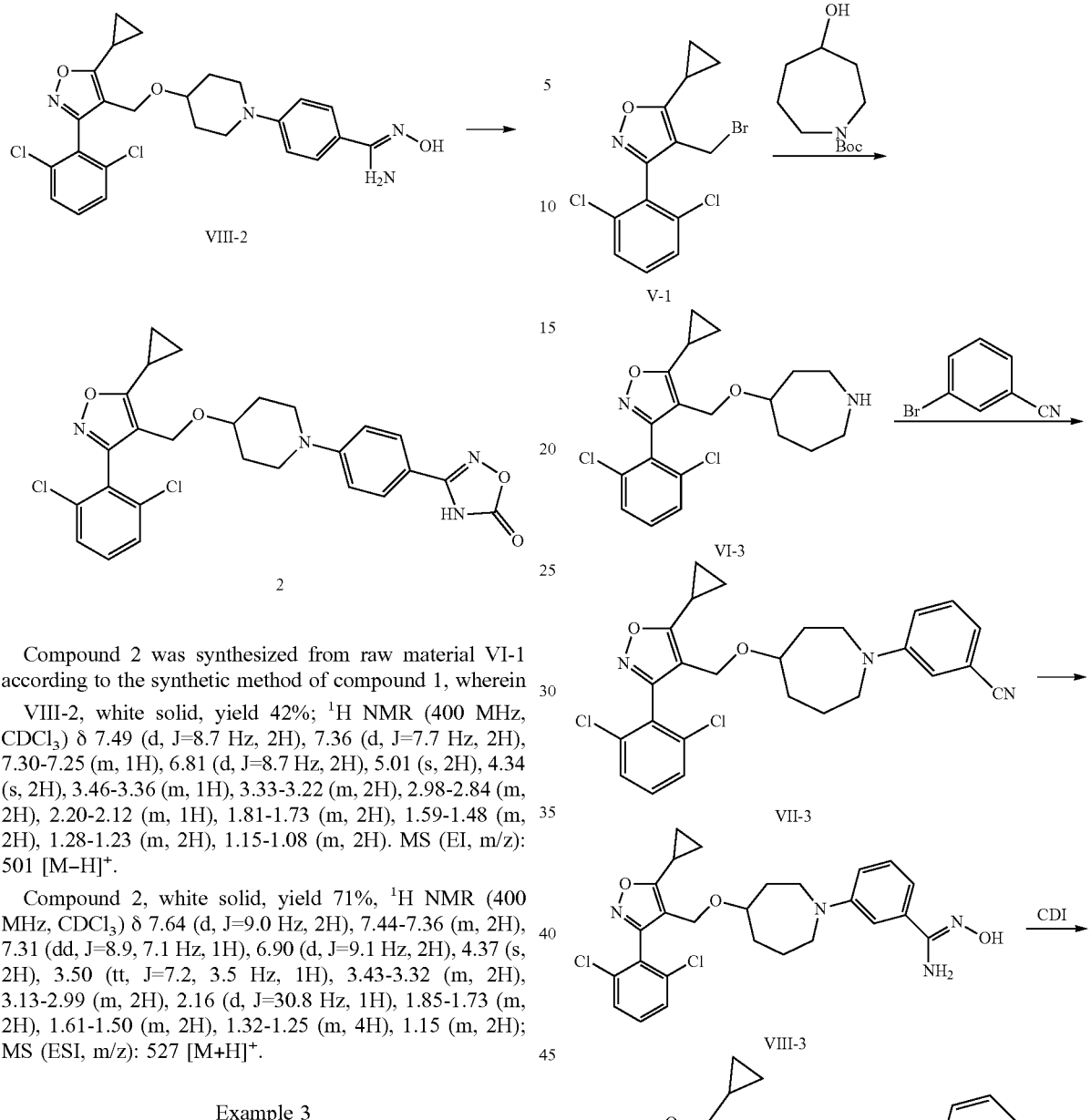

Compound 2 was synthesized from raw material VI-1 according to the synthetic method of compound 1, wherein VIII-2, white solid, yield 42%; $^1$H NMR (400 MHz, CDCl$_3$) δ 7.49 (d, J=8.7 Hz, 2H), 7.36 (d, J=7.7 Hz, 2H), 7.30-7.25 (m, 1H), 6.81 (d, J=8.7 Hz, 2H), 5.01 (s, 2H), 4.34 (s, 2H), 3.46-3.36 (m, 1H), 3.33-3.22 (m, 2H), 2.98-2.84 (m, 2H), 2.20-2.12 (m, 1H), 1.81-1.73 (m, 2H), 1.59-1.48 (m, 2H), 1.28-1.23 (m, 2H), 1.15-1.08 (m, 2H). MS (EI, m/z): 501 [M−H]$^+$.

Compound 2, white solid, yield 71%, $^1$H NMR (400 MHz, CDCl$_3$) δ 7.64 (d, J=9.0 Hz, 2H), 7.44-7.36 (m, 2H), 7.31 (dd, J=8.9, 7.1 Hz, 1H), 6.90 (d, J=9.1 Hz, 2H), 4.37 (s, 2H), 3.50 (tt, J=7.2, 3.5 Hz, 1H), 3.43-3.32 (m, 2H), 3.13-2.99 (m, 2H), 2.16 (d, J=30.8 Hz, 1H), 1.85-1.73 (m, 2H), 1.61-1.50 (m, 2H), 1.32-1.25 (m, 4H), 1.15 (m, 2H); MS (ESI, m/z): 527 [M+H]$^+$.

Example 3

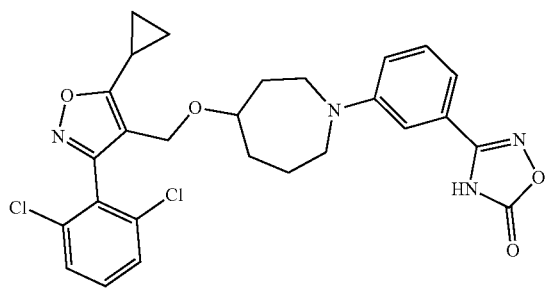

3

Example 3 was carried out by referring to the operation of example 1. The compound was prepared from intermediate V-1 via route 1. The synthetic route was as follows.

At 0° C., potassium tert-butoxide (6.5 mmol) was added to a solution of tert-butyl 4-hydroxyhexahydroazepine-1-carboxylate (6.5 mmol) in anhydrous tetrahydrofuran (20 mL) and stirred for 30 minutes, and then a solution of V-1 (4.3 mmol) in anhydrous tetrahydrofuran (5 mL) was added dropwise, and the reaction was carried out for 8 h. Water (20 mL) was added to the reaction solution, which was then extracted with ethyl acetate (15 mL each time, 3 times in total). The organic phase was washed with saturated brine, concentrated, and subjected to column chromatography to obtain an intermediate. The intermediate was dissolved in dichloromethane (8 mL) and cooled to 0° C., and trifluoroacetic acid (8 mL) was added dropwise, and stirred at room temperature for 3 h. The solvent was removed under vacuum, ethyl acetate (20 mL) was added to dissolve, washed with 2N sodium hydroxide solution, saturated brine, and the solvent was removed to obtain intermediate VI-3 (0.87 g, yield 53%). ¹H NMR (400 MHz, CDCl₃) δ 7.45-7.40 (m, 2H), 7.38-7.32 (m, 1H), 4.35-4.23 (m, 2H), 3.49-3.42 (m, 1H), 3.40-3.18 (m, 4H), 2.18-2.09 (m, 1H), 1.83-1.59 (m, 5H), 1.55-1.46 (m, 1H), 1.28-1.23 (m, 2H), 1.16-1.10 (m, 2H).

Intermediate VI-3 (0.8 g), 4-bromobenzonitrile (4.1 mmol), sodium tert-butoxide (5.4 mmol), palladium acetate (0.14 mmol), and 1,1'-binaphthyl-2,2'-bisdiphenylphosphine (0.27 mmol) were added to a round bottom flask, and toluene (60 mL) was added under the protection of nitrogen, heated to reflux, and reacted overnight. The reaction solution was cooled to room temperature and water was added. The mixture was extracted, concentrated, and subjected to column chromatography to obtain intermediate VII-3 (0.49 g, yield 48%). ¹H NMR (400 MHz, CDCl₃) δ 7.44-7.40 (m, 2H), 7.37-7.33 (m, 1H), 7.27-7.21 (m, 1H), 6.92-6.86 (m, 1H), 6.83-6.78 (m, 2H), 4.34-4.24 (m, 2H), 3.49-3.43 (m, 1H), 3.39-3.18 (m, 4H), 2.18-2.10 (m, 1H), 1.84-1.58 (m, 5H), 1.55-1.48 (m, 1H), 1.27-1.24 (m, 2H), 1.15-1.09 (m, 2H).

Compound 3 was synthesized from VII-3 as the raw material according to the synthesis method of compound 1, yield 66%, ¹H NMR (400 MHz, CDCl₃) δ 7.42-7.38 (m, 2H), 7.36-7.31 (m, 1H), 7.30-7.25 (m, 1H), 7.03-6.99 (m, 2H), 6.82-6.75 (m, 1H), 4.35-4.23 (m, 2H), 3.48-3.20 (m, 5H), 2.18-2.10 (m, 1H), 1.89-1.57 (m, 5H), 1.55-1.45 (m, 1H), 1.26-1.21 (m, 2H), 1.15-1.08 (m, 2H). MS (ESI, m/z): 541 [M+H]⁺.

Example 4

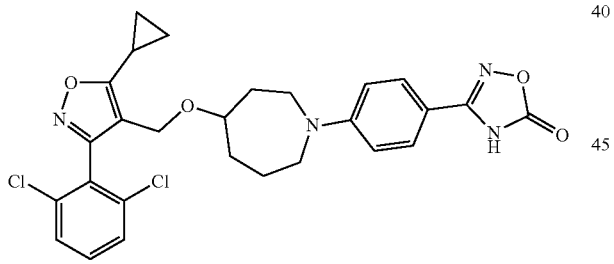

4

Example 4 was carried out by referring to the operation of example 1. The compound was prepared from intermediate VI-3 via route 1. The synthetic route was as follows.

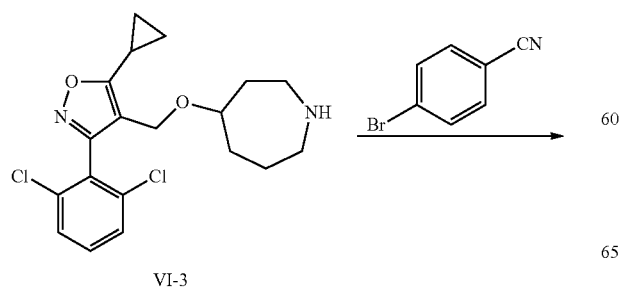

VI-3

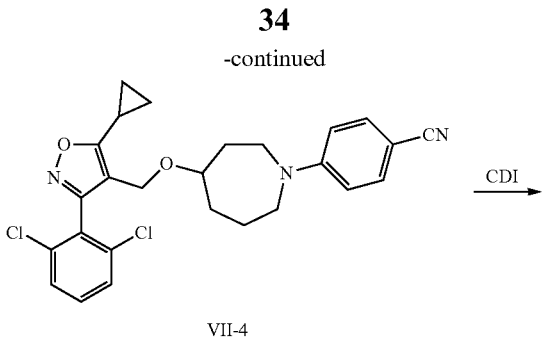

VII-4

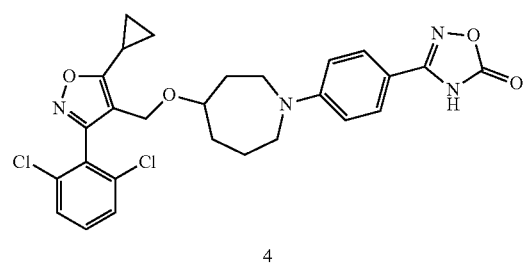

4

Compound 4 was synthesized from VI-3 as the raw material according to the synthesis method of compound 1, wherein, VII-4, white solid, yield 59%, ¹H NMR (400 MHz, CDCl₃) δ 7.45-7.40 (m, 4H), 7.37-7.32 (m, 1H), 6.60 (d, J=9.1 Hz, 2H), 4.33-4.24 (m, 2H), 3.52-3.19 (m, 5H), 2.17-2.09 (m, 1H), 1.82-1.60 (m, 5H), 1.51-1.43 (m, 1H), 1.29-1.24 (m, 2H), 1.15-1.09 (m, 2H).

Compound 4, white solid, yield 69%, ¹H NMR (400 MHz, CDCl₃) δ 7.60 (d, J=8.9 Hz, 2H), 7.44-7.39 (m, 2H), 7.38-7.33 (m, 1H), 6.66 (d, J=9.1 Hz, 2H), 4.35-4.23 (m, 2H), 3.51-3.19 (m, 5H), 2.18-2.08 (m, 1H), 1.83-1.59 (m, 5H), 1.54-1.45 (m, 1H), 1.28-1.23 (m, 2H), 1.15-1.08 (m, 2H). MS (ESI, m/z): 541 [M+H]⁺.

Example 5

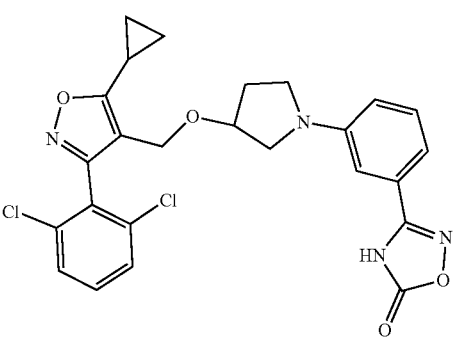

5

Example 5 was carried out by referring to the operation of example 1. The compound was prepared from intermediate V-1 via route 1. The synthetic route was as follows.

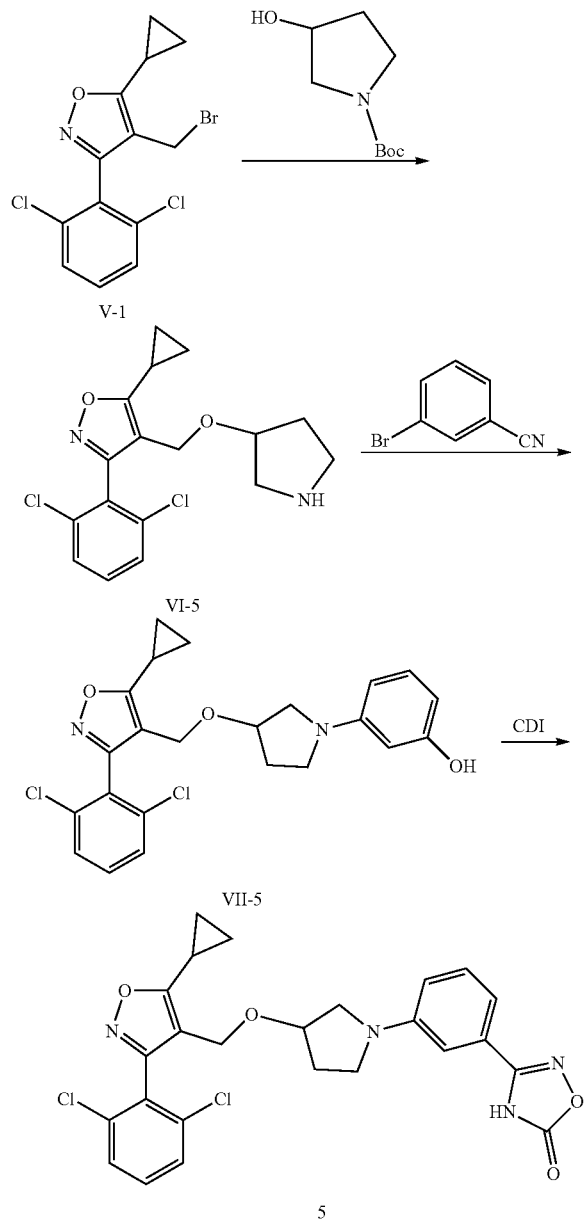

Compound 5 was synthesized from V-1 as the raw material according to the synthesis method of compound 1, wherein VI-5, colloid, yield 61%, $^1$H NMR (400 MHz, CDCl$_3$) δ 7.45-7.40 (m, 2H), 7.39-7.32 (m, 1H), 4.36-4.22 (m, 2H), 3.98-3.92 (m, 1H), 3.40-3.13 (m, 4H), 2.17-2.08 (m, 1H), 1.83-1.73 (m, 2H), 1.31-1.24 (m, 2H), 1.17-1.11 (m, 2H).

VII-5, white solid, yield 49%, $^1$H NMR (400 MHz, CDCl$_3$) δ 7.33 (dd, J=7.5, 1.8 Hz, 1H), 7.27-7.19 (m, 3H), 6.94 (d, J=7.5 Hz, 1H), 6.66-6.59 (m, 2H), 4.40-4.28 (m, 2H), 4.19-4.13 (m, 1H), 3.35-3.18 (m, 3H), 3.04 (d, J=10.5 Hz, 1H), 2.18-2.09 (m, 1H), 2.04-1.97 (m, 2H), 1.30-1.25 (m, 2H), 1.16-1.11 (m, 2H).

5, white solid, yield 63%, $^1$H NMR (400 MHz, CDCl$_3$) δ 7.33-7.13 (m, 4H), 7.06 (d, J=7.8 Hz, 1H), 6.83 (s, 1H), 6.62-6.57 (m, 1H), 4.39-4.29 (m, 2H), 3.38-3.32 (m, 1H), 3.31-3.19 (m, 2H), 3.11 (d, J=10.3 Hz, 1H), 2.18-2.10 (m, 1H), 2.01-1.94 (m, 2H), 1.26-1.22 (m, 2H), 1.16-1.09 (m, 2H). MS (ESI, m/z): 513 [M+H]$^+$.

Example 6

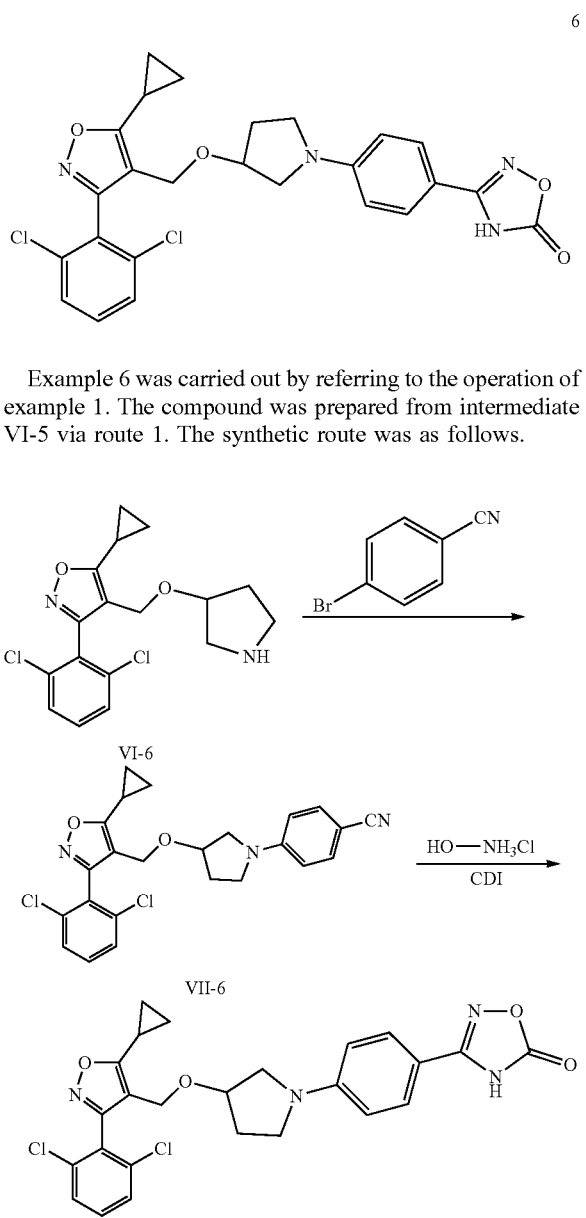

Example 6 was carried out by referring to the operation of example 1. The compound was prepared from intermediate VI-5 via route 1. The synthetic route was as follows.

Compound 6 was synthesized from VI-5 as the raw material according to the synthesis method of compound 1, wherein, VII-6, white solid, yield 38%. $^1$H NMR (400 MHz, CDCl$_3$) δ 7.46 (d, J=8.9 Hz, 2H), 7.31 (dd, J=7.9, 1.2 Hz, 1H), 7.25 (dd, J=8.1, 1.2 Hz, 1H), 7.18 (t, J=7.9 Hz, 1H), 6.40 (d, 0.1=8.9 Hz, 2H), 4.40-4.28 (m, 2H), 4.19-4.12 (m, 1H), 3.37-3.22 (m, 3H), 3.11 (d, J=11.0 Hz, 1H), 2.17-1.93 (m, 3H), 1.31-1.26 (m, 2H), 1.18-1.11 (m, 2H).

6, white solid, yield 69%. $^1$H NMR (400 MHz, DMSO-d6) δ 7.59 (d, J=8.8 Hz, 2H), 7.54-7.39 (m, 3H), 6.53 (d, J=8.8 Hz, 2H), 4.32 (q, J=12.1 Hz, 2H), 4.10 (s, 1H), 3.31-3.23 (m, 2H), 3.12-3.04 (m, 2H), 2.39-2.28 (m, 1H), 2.02-1.84 (m, 2H), 1.15-1.06 (m, 4H). MS (ESI, m/z): 513 [M+H]⁺.

Example 7

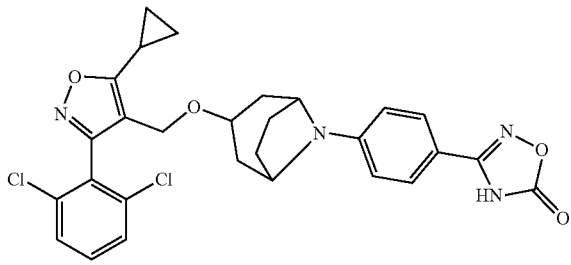

7

Example 7 was carried out by referring to the operation of example 1. The compound was prepared from intermediate V-1 via route 1. The synthetic route was as follows.

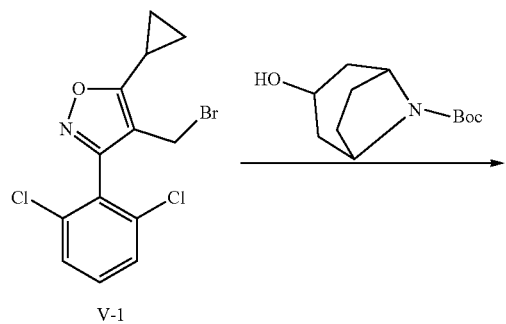

V-1

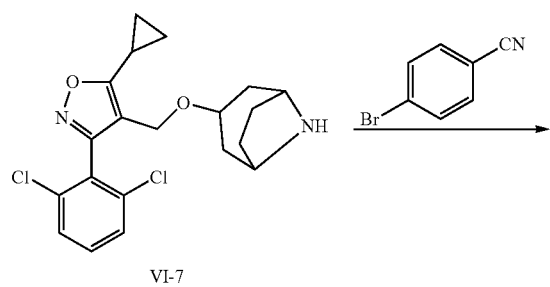

VI-7

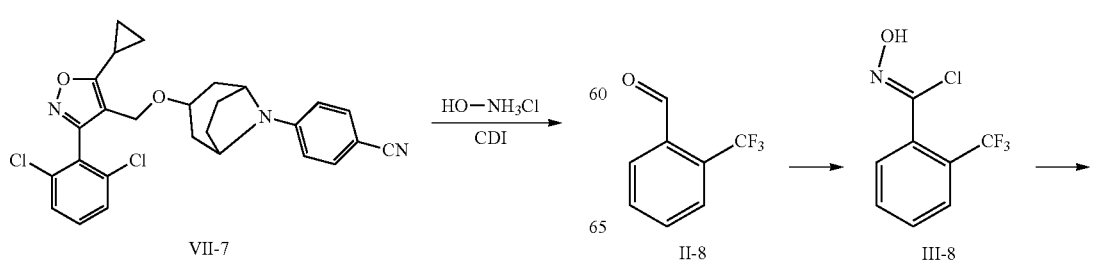

VII-7

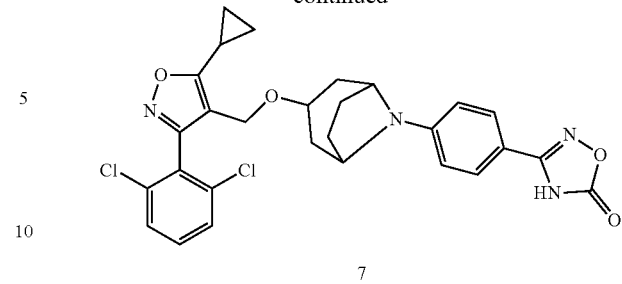

7

Compound 7 was synthesized from V-1 as the raw material according to the synthesis method of compound 1, wherein, VI-7, colloid, yield 67%. ¹H NMR (400 MHz, CDCl₃) δ 7.42-7.39 (m, 2H), 7.36-7.31 (m, 1H), 4.27-4.18 (m, 2H), 4.10-3.96 (m, 2H), 3.53 (t, J=4.7 Hz, 1H), 2.16-2.07 (m, 1H), 1.91-1.69 (m, 6H), 1.64 (d, J=14.4 Hz, 2H), 1.26-1.22 (m, 2H), 1.14-1.08 (m, 2H).

VII-7, white solid, yield 54%. ¹H NMR (400 MHz, CDCl₃) δ 7.47-7.42 (m, 4H), 7.38-7.34 (m, 1H), 6.65 (d, J=8.9 Hz, 2H), 4.26 (s, 2H), 4.13-4.10 (m, 2H), 3.46-3.41 (m, 1H), 2.17-2.09 (m, 1H), 1.97-1.81 (m, 6H), 1.66-1.61 (m, 2H), 1.28-1.25 (m, 2H), 1.17-1.11 (m, 2H).

7, white solid, yield 77%. ¹H NMR (400 MHz, CDCl₃) δ 7.60 (d, J=8.8 Hz, 2H), 7.44-7.40 (m, 2H), 7.37-7.32 (m, 1H), 6.70 (d, J=9.0 Hz, 2H), 4.25 (s, 2H), 4.12-4.08 (m, 2H), 3.42 (s, 1H), 2.18-2.10 (m, 1H), 1.99-1.82 (m, 6H), 1.61 (d, J=14.4 Hz, 2H), 1.26-1.22 (m, 2H), 1.16-1.10 (m, 2H). MS (ESI, m/z): 553 [M+H]⁺.

Example 8

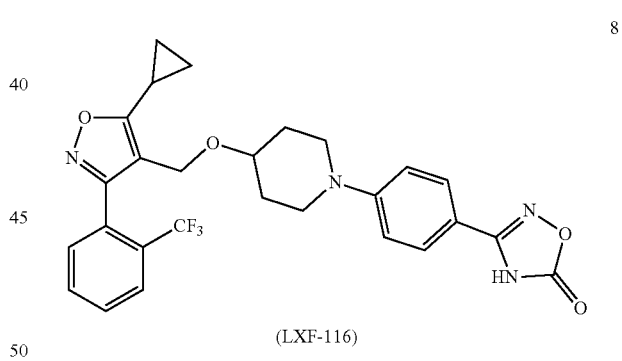

(LXF-116)

Example 8, i.e., the preparation of LXF-116 was carried out by referring to the operation of example 1. The compound was prepared from intermediate II-8 via route 1. The synthetic route was as follows.

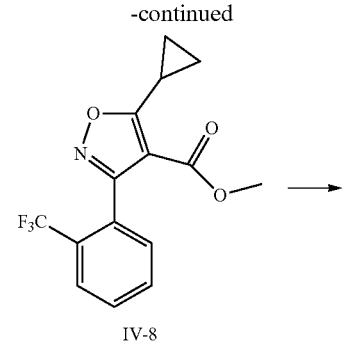

IV-8

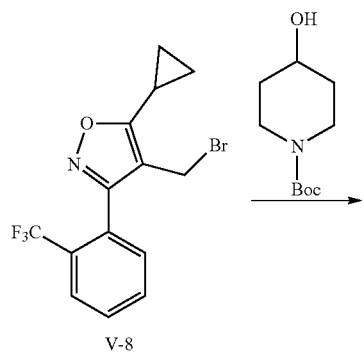

V-8

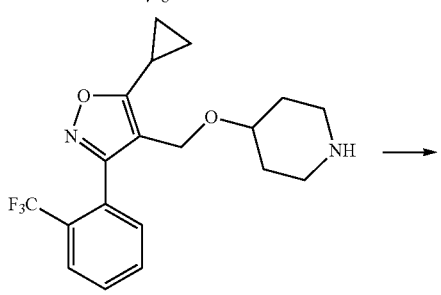

VI-8

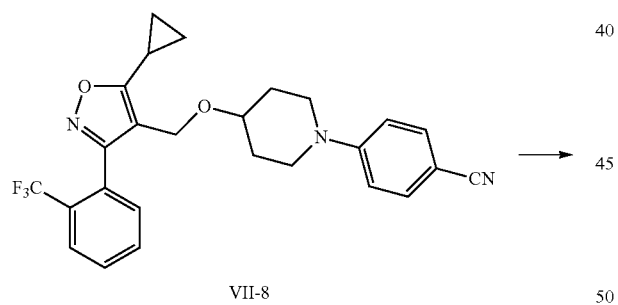

VII-8

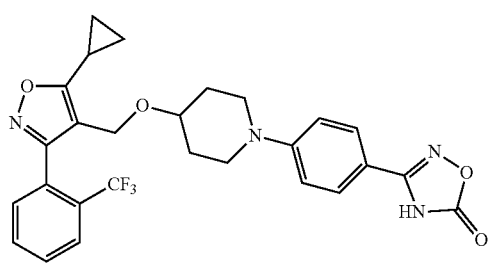

8

Compound 8 was synthesized from II-8 as the raw material according to the synthesis method of compound 1, wherein, IV-8, white solid, yield 58%. $^1$H NMR (400 MHz, CDCl$_3$) δ 7.82 (d, J=7.5 Hz, 1H), 7.74-7.59 (m, 2H), 7.56 (d, J=7.5 Hz, 1H), 3.3.73 (s, 3H), 2.19-2.09 (m, 1H), 1.33-1.27 (m, 2H), 1.24-1.15 (m, 2H).

V-8, colourless liquid, yield 88%. $^1$H NMR (400 MHz, CDCl$_3$) δ 7.84 (d, J=7.4 Hz, 1H), 7.73-7.61 (m, 2H), 7.57 (d, J=7.4 Hz, 1H), 4.23 (s, 2H), 2.17-2.09 (m, 1H), 1.32-1.27 (m, 2H), 1.23-1.17 (m, 2H).

VI-8, colloid, yield 78%. $^1$H NMR (400 MHz, CDCl$_3$) δ 7.79 (d, J=7.0 Hz, 1H), 7.66-7.56 (m, 2H), 7.41 (d, J=7.0 Hz, 1H), 4.23 (s, 2H), 3.55-3.49 (m, 1H), 3.03-2.91 (m, 4H), 2.10-2.02 (m, 1H), 1.94-1.77 (m, 2H), 1.75-1.64 (m, 2H), 1.25-1.07 (m, 4H).

VII-8, white solid, yield 48%. $^1$H NMR (400 MHz, CDCl$_3$) δ 7.77 (d, J=7.2 Hz, 1H), 7.62-7.51 (m, 2H), 7.48-7.40 (m, 3H), 6.79 (d, J=9.0 Hz, 2H), 4.27 (s, 2H), 3.49-3.35 (m, 3H), 3.12-2.96 (m, 2H), 2.16-2.07 (m, 1H), 1.85-1.70 (m, 2H), 1.58-1.46 (m, 2H), 1.23-1.18 (m, 2H), 1.13-1.06 (m, 2H).

8, white solid, yield 72%. $^1$H NMR (400 MHz, DMSO-d6) δ 7.88 (d, J=7.6 Hz, 1H), 7.80-7.67 (m, 2H), 7.64-7.56 (m, 3H), 6.99 (d, J=8.8 Hz, 2H), 4.28 (s, 2H), 3.46-3.37 (m, 3H), 3.04-2.94 (m, 2H), 2.35-2.25 (m, 1H), 1.70 (s, 2H), 1.41-1.27 (m, 2H), 1.17-1.03 (m, 4H). MS (ESI, m/z): 527 [M+H]$^+$.

Example 9

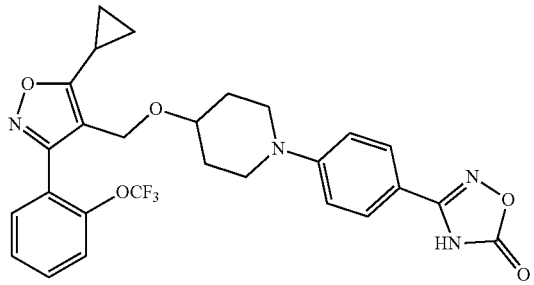

9

Example 9 was carried out by referring to the operation of example 1. The compound was prepared from intermediate II-9 via route 1. The synthetic route was as follows.

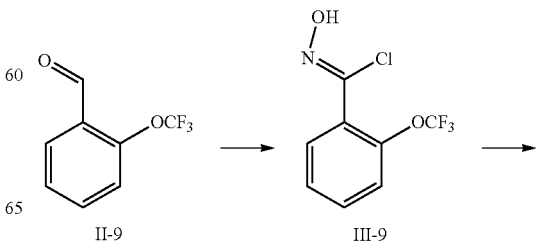

II-9          III-9

-continued

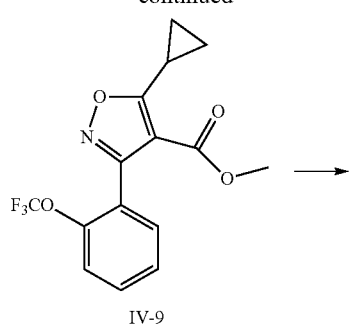

IV-9, white solid, yield 59%. $^1$H NMR (400 MHz, CDCl$_3$) δ 7.66-7.50 (m, 2H), 7.49-7.41 (m, 2H), 3.70 (s, 2H), 2.18-2.10 (m, 1H), 1.31-1.26 (m, 2H), 1.23-1.17 (m, 2H).

V-9, colourless liquid, yield 82%. $^1$H NMR (400 MHz, CDCl$_3$) δ 7.65-7.52 (m, 2H), 7.49-7.40 (m, 2H), 4.36 (s, 2H), 2.18-2.10 (m, 1H), 1.31-1.26 (m, 2H), 1.23-1.17 (m, 2H).

VI-9, colloid, yield 80%. $^1$H NMR (400 MHz, CDCl$_3$) δ 7.45-7.30 (m, 4H), 4.29-4.18 (m, 2H), 2H), 3.50-3.36 (m, 3H), 3.12-3.00 (m, 2H), 2.18-2.10 (m, 1H), 1.86-1.76 (m, 2H), 1.61-1.50 (m, 2H), 1.28-1.22 (m, 2H), 1.13-1.07 (m, 2H).

VII-9, white solid, yield 55%. $^1$H NMR (400 MHz, CDCl$_3$) δ 7.58-7.47 (m, 2H), 7.45-7.34 (m, 4H), 6.81 (d, J=9.0 Hz, 2H), 4.28 (s, 2H), 3.50-3.38 (m, 3H), 3.14-3.00 (m, 2H), 2.18-2.10 (m, 1H), 1.85-1.76 (m, 2H), 1.61-1.50 (m, 2H), 1.27-1.22 (m, 2H), 1.13-1.07 (m, 2H).

9, white solid, yield 69%. $^1$H NMR (400 MHz, DMSO) δ 7.69-7.48 (m, 6H), 7.00 (d, J=8.9 Hz, 2H), 4.37 (s, 2H), 3.55-3.40 (m, 3H), 3.06-2.96 (m, 2H), 2.37-2.28 (m, 1H), 1.80-1.69 (m, 2H), 1.44-1.31 (m, 2H), 1.16-1.03 (m, 4H). MS (EsI, m/z): 543 [M+H]$^+$.

Example 10

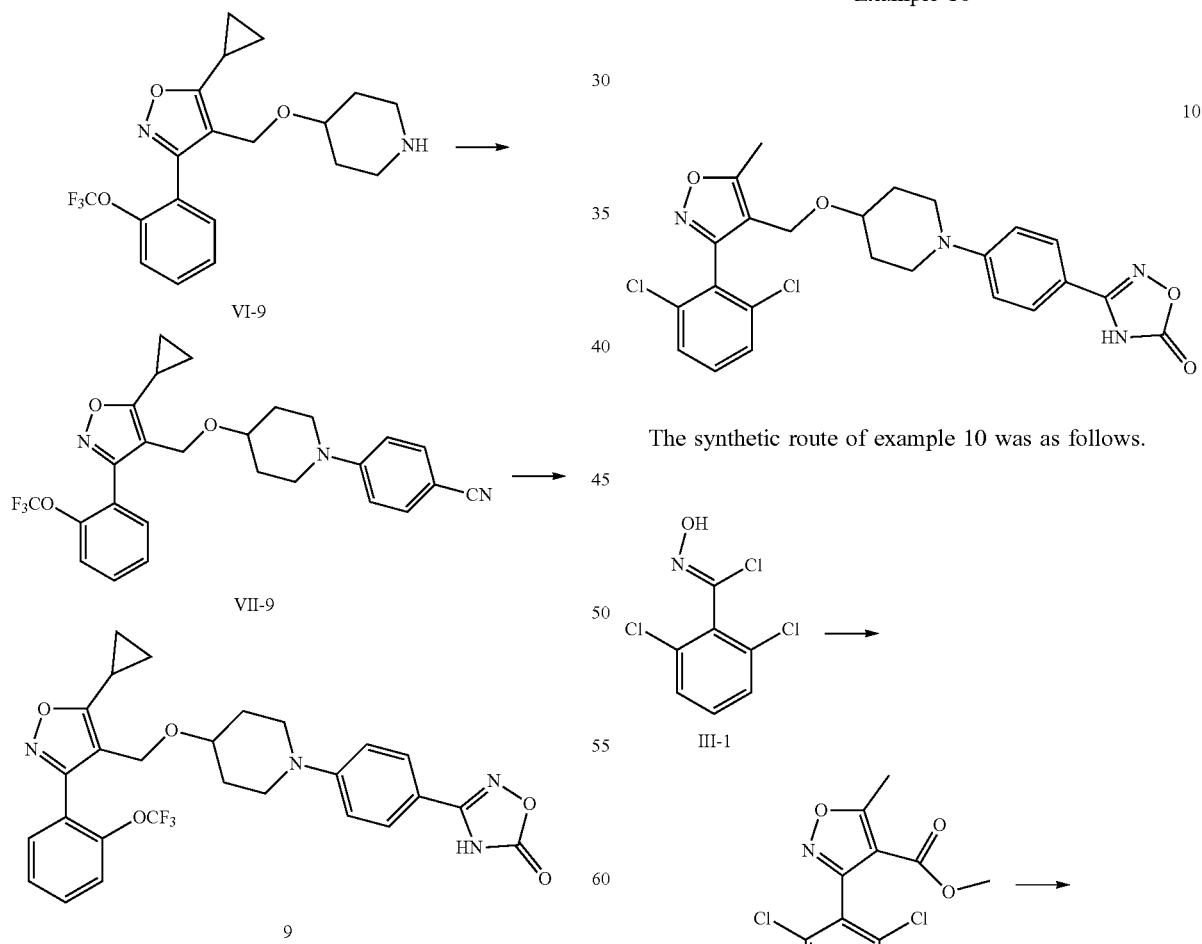

The synthetic route of example 10 was as follows.

Compound 9 was synthesized from II-9 as the raw material according to the synthesis method of compound 1, wherein,

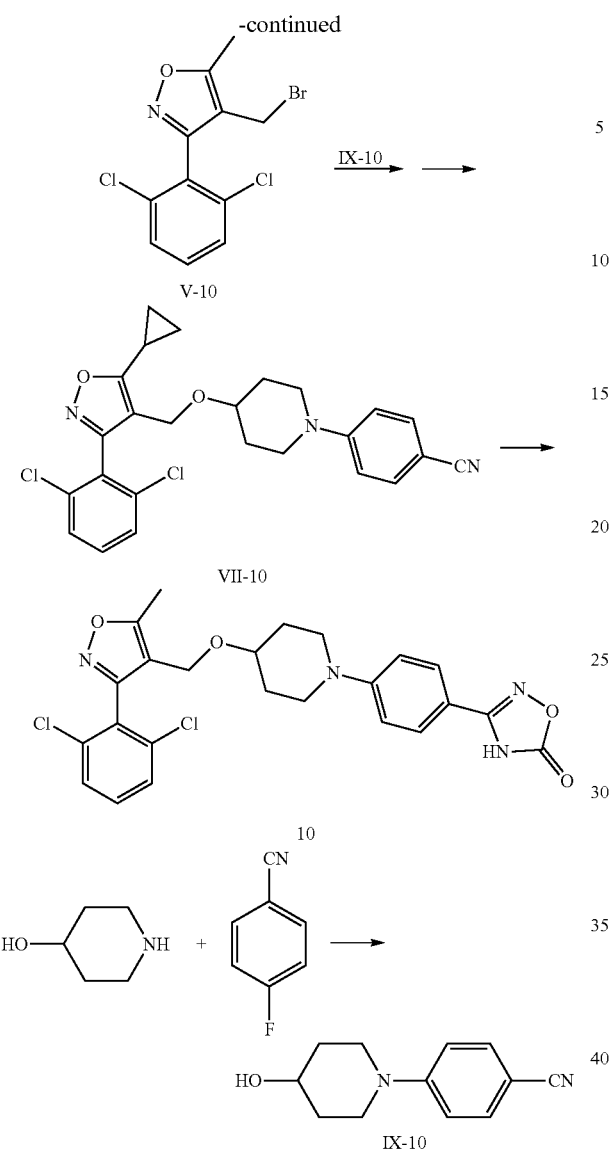

At 0° C., sodium methoxide/methanol solution (5.4 M, 4.1 mL) was slowly added dropwise into a solution of methyl acetoacetate (22.2 mmol) in anhydrous tetrahydrofuran (10 ml), and then a solution of III-1 (5 g, 22.2 mmol)) in anhydrous tetrahydrofuran (10 mL) was added and stirred at room temperature for 12 h. Ethyl acetate (40 mL) was added to the reaction solution, the organic phase was washed with water and saturated brine, and the solvent was removed to obtain an oily substance, which was then subjected to column chromatography to obtain intermediate IV-10 (3.4 g, yield 54%). $^1$H NMR (400 MHz, CDCl$_3$) δ 7.45-7.41 (m, 2H), 7.39-7.34 (m, 1H), 3.71 (s, 3H), 2.82 (s, 3H).

4-fluorobenzonitrile (2 g, 16.5 mmol), 4-hydroxypiperidine (18.2 mmol), anhydrous potassium carbonate (41.3 mmol) and DMSO (16 mL) were added to a round bottom flask, heated to 130° C., and reacted for 12 h. The mixture was cooled to room temperature, added with 30 mL of water, and filtered. The solid was washed with water to obtain intermediate IX-10 (3.1 g, yield 93%). $^1$H NMR (400 MHz, CDCl$_3$) δ 7.52-7.43 (m, 2H), 6.91-6.80 (m, 2H), 4.00-3.91 (m, 1H), 3.77-3.63 (m, 2H), 3.13 (ddd, J=13.0, 9.4, 3.3 Hz, 2H), 2.05-1.95 (m, 2H), 1.70-1.59 (m, 2H).

The compound intermediate V-10 was synthesized by IV-10 as the raw material according to the synthesis method of the compound V-1. At 0° C., potassium tert-butoxide (6.5 mmol) was added to a solution of IX-10 (1.3 g, 6.5 mmol) in anhydrous tetrahydrofuran (20 ml) and stirred for 30 minutes, and then a solution of V-10 (4.3 mmol) in anhydrous tetrahydrofuran (5 mL) was added dropwise and reacted for 8 h. Water (20 mL) was added to the reaction solution, which was then extracted with ethyl acetate (15 mL×3). The organic phase was washed with saturated brine, concentrated, and subjected to column chromatography to obtain intermediate VII-10 (1.21 g, yield 64%). $^1$H NMR (400 MHz, CDCl$_3$) δ 7.47 (d, J=9.0 Hz, 2H), 7.42-7.38 (m, 2H), 7.33-7.29 (m, 1H), 6.80 (d, J=9.0 Hz, 2H), 4.28 (s, 2H), 3.51-3.43 (m, 1H), 3.37-3.29 (m, 2H), 3.12-2.97 (m, 2H), 2.55 (s, 3H), 1.78-1.72 (m, 2H), 1.59-1.49 (m, 2H).

Compound 10 was synthesized from VII-10 as the raw material according to the synthesis method of compound 1, white solid, yield 64%. $^1$H NMR (400 MHz, CDCl$_3$) δ 7.64 (d, J=8.9 Hz, 2H), 7.45-7.36 (m, 2H), 7.34-7.28 (m, 1H), 6.88 (d, J=8.9 Hz, 2H), 4.29 (s, 2H), 3.51-3.27 (m, 3H), 3.14-2.99 (m, 2H), 2.55 (s, 3H), 1.85-1.70 (m, 2H), 1.62-1.47 (m, 2H). MS (ESI, m/z): 501 [M+H]

Example 11

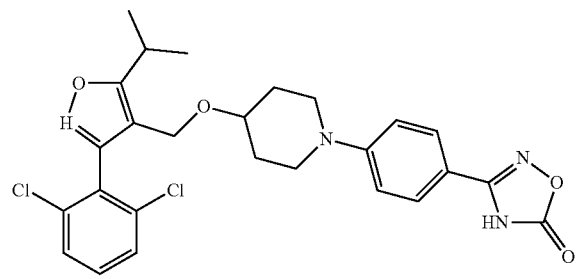

The synthetic route of example 11 was as follows.

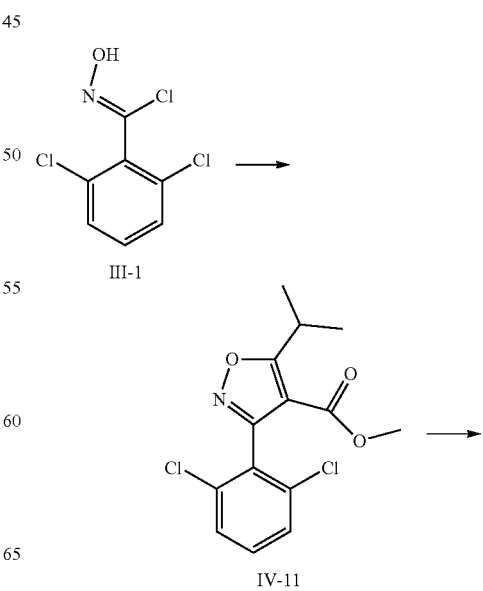

-continued

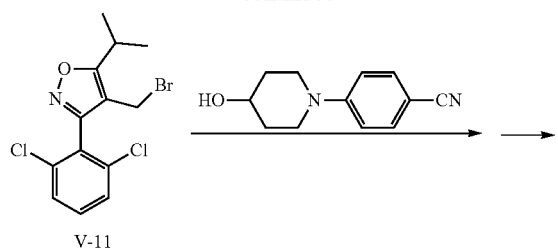

V-11

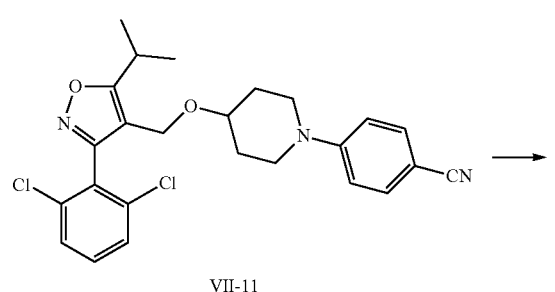

VII-11

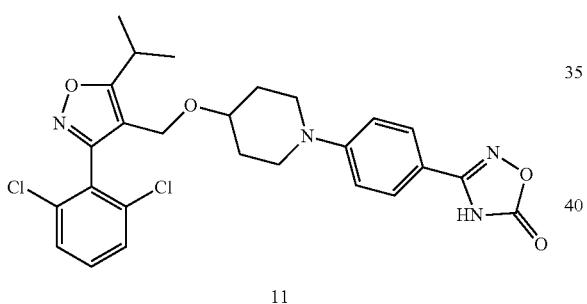

11

Compound intermediate IV-11 (yield 61%) was synthesized from III-1 as the raw material according to the synthesis method of compound IV-10, wherein, methyl acetoacetate was replaced by methyl isobutyryl acetate. ¹H NMR (400 MHz, CDCl₃) δ 7.44-7.41 (m, 2H), 7.38-7.33 (m, 1H), 3.95-3.83 (m, 1H), 3.69 (s, 3H), 1.46 (d, J=7.0 Hz, 6H).

Compound intermediate VII-11 was synthesized from IV-1 as the raw material according to the synthesis method of compound VII-10, white solid, yield 71%; ¹H NMR (400 MHz, CDCl₃) δ 7.43-7.38 (m, 2H), 7.37-7.32 (m, 2H), 7.28-7.23 (m, 1H), 6.79-6.71 (m, 2H), 4.23 (s, 2H), 3.46-3.36 (m, 1H), 3.34-3.23 (m, 2H), 3.07-2.98 (m, 2H), 1.73-1.63 (m, 2H), 1.50-1.45 (m, 2H), 1.38 (d, J=7.1 Hz, 6H).

Compound 11 was synthesized from VII-11 as the raw material according to the synthesis method of compound 1, white solid, yield 66%. ¹H NMR (400 MHz, CDCl₃) δ 7.63 (d, J=8.9 Hz, 2H), 7.43-7.37 (m, 2H), 7.34-7.27 (m, 1H), 6.87 (d, J=9.0 Hz, 2H), 4.29 (s, 2H), 3.50-3.29 (m, 4H), 3.12-2.98 (m, 2H), 1.80-1.69 (m, 2H), 1.59-1.47 (m, 2H), 1.43 (d, J=7.0 Hz, 6H). MS (ESI, m/z): 529 [M+H]⁺.

Example 12

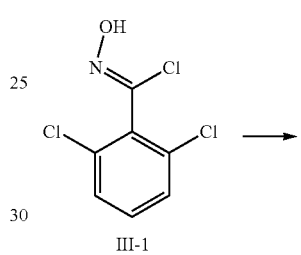

12

The synthetic route of example 12 was as follows.

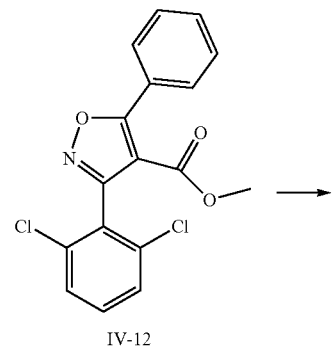

III-1

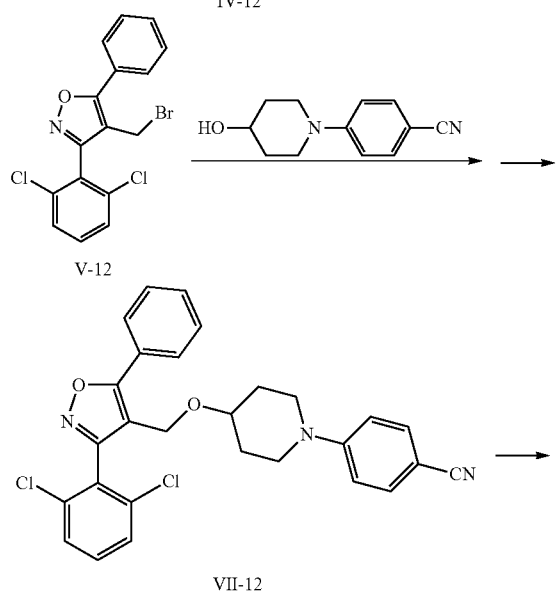

IV-12

V-12

VII-12

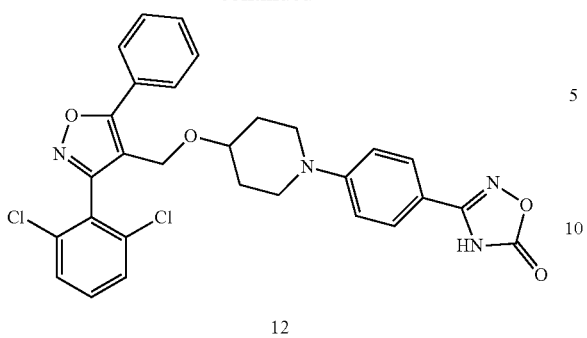

12

Compound intermediate IV-12 (yield 67%) was synthesized from III-1 as the raw material according to the synthesis method of compound IV-10, wherein, methyl acetoacetate was replaced by methyl benzoylacetate. $^1$H NMR (400 MHz, CDCl$_3$) δ 8.10 (d, J=7.9 Hz, 1H), 7.97 (d, J=7.9 Hz, 1H), 7.58-7.44 (m, 5H), 7.41-7.36 (m, 1H), 3.65 (s, 3H).

Compound intermediate VII-12 was synthesized from IV-12 as the raw material according to the synthesis method of compound VII-10, white solid, yield 74%; $^1$H NMR (400 MHz. CDCl$_3$) δ 7.95 (dd, J=7.8, 1.7 Hz, 2H), 7.64 (d, J=8.9 Hz, 2H), 7.59-7.51 (m, 3H), 7.49-7.44 (m, 2H), 7.42-7.35 (m, 1H), 6.90 (d, J=8.9 Hz, 2H), 4.46 (s, 2H), 3.57-3.50 (m, 1H), 3.46-3.37 (m, 2H), 3.12-2.99 (m, 2H), 1.81-1.70 (m, 2H), 1.62-1.49 (m, 2H).

Compound 12 was synthesized from VII-12 as the raw material according to the synthesis method of compound 1, white solid, yield 56%. $^1$H NMR (400 MHz, CDCl$_3$) δ 11.50 (s, 1H), 7.95 (dd, J=7.8, 1.7 Hz, 2H), 7.64 (d, J=8.9 Hz, 2H), 7.59-7.51 (m, 3H), 7.49-7.44 (m, 2H), 7.42-7.35 (m, 1H), 6.90 (d, J=8.9 Hz, 2H), 4.46 (s, 2H), 3.57-3.50 (m, 1H), 3.46-3.37 (m, 2H), 3.12-2.99 (m, 2H), 1.81-1.70 (m, 2H), 1.62-1.49 (m, 2H). MS (ESI, m/z): 562 [M+H]$^+$.

Example 13

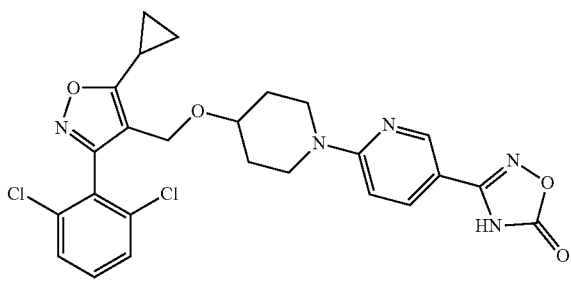

13

The synthetic route of example 13 was as follows.

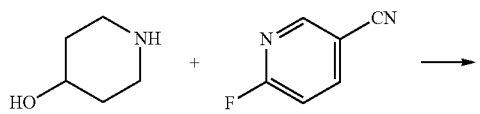

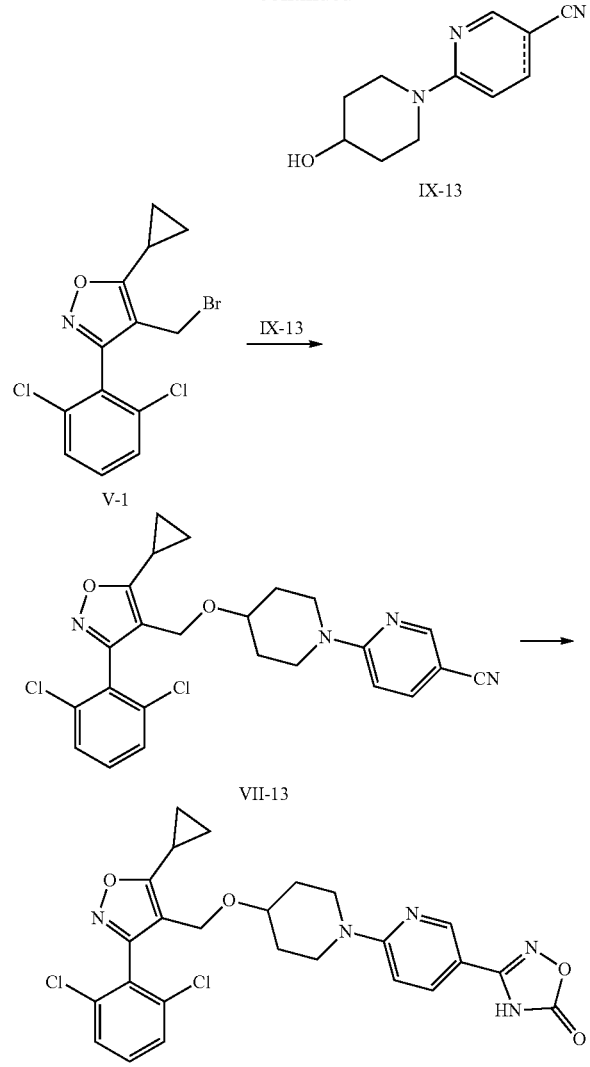

Compound intermediate IX-13 was synthesized from 4-hydroxypiperidine as the raw material according to the synthesis method of compound IX-10, white solid, yield 94%; $^1$H NMR (400 MHz, CDCl$_3$) δ 8.37 (d, J=2.0 Hz, 1H), 7.57 (dd, J=9.1, 2.0 Hz, 1H), 6.62 (d, J=9.1 Hz, 1H), 4.16-3.93 (m, 3H), 3.41-3.30 (m, 2H), 2.00-1.91 (m, 2H), 1.63-1.52 (m, 2H).

Compound intermediate VII-13 was synthesized from V-1 as the raw material according to the synthesis method of compound VII-1, white solid, yield 74%; $^1$H NMR (400 MHz. CDCl$_3$) δ 8.26 (d, J=2.1 Hz, 1H), 7.47 (dd, J=9.1, 2.1 Hz, 1H), 7.35-7.30 (m, 2H), 7.27-7.22 (m, 1H), 6.50 (d, J=9.1 Hz, 1H), 4.27 (s, 2H), 3.66-3.56 (m, 2H), 3.45-3.40 (m, 1H), 3.36-3.24 (m, 2H), 2.13-2.04 (m, 1H), 1.65-1.58 (m, 3H), 1.45-1.35 (m, 2H), 1.16-1.12 (m, 2H), 1.07-1.00 (m, 2H).

Compound 13 was synthesized from VII-13 as the raw material according to the synthesis method of compound 1, white solid, yield 71%; $^1$H NMR (400 MHz, CDCl$_3$) δ 8.52 (d, J=2.4 Hz, 1H), 7.79 (dd, J=9.1, 2.5 Hz, 1H), 7.45-7.31 (m, 3H), 6.67 (d, J=9.1 Hz, 1H), 4.38 (s, 2H), 3.81-3.67 (m, 2H), 3.61-3.50 (m, 1H), 3.46-3.33 (m, 2H), 2.17 (s, 1H), 1.82-1.68 (m, 2H), 1.59-1.45 (m, 2H), 1.31-1.27 (m, 2H), 1.19-1.12 (m, 2H). MS (ESI, m/z): 528 [M+H]P.

Example 14

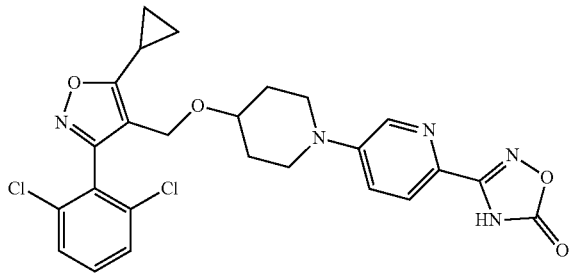

14

The synthetic route of example 14 was as follows.

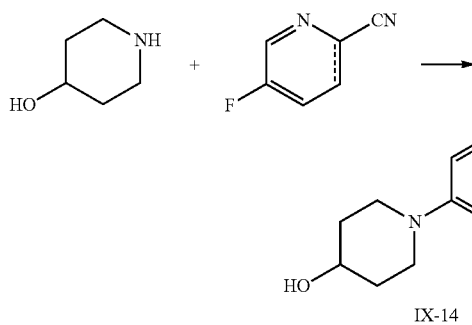

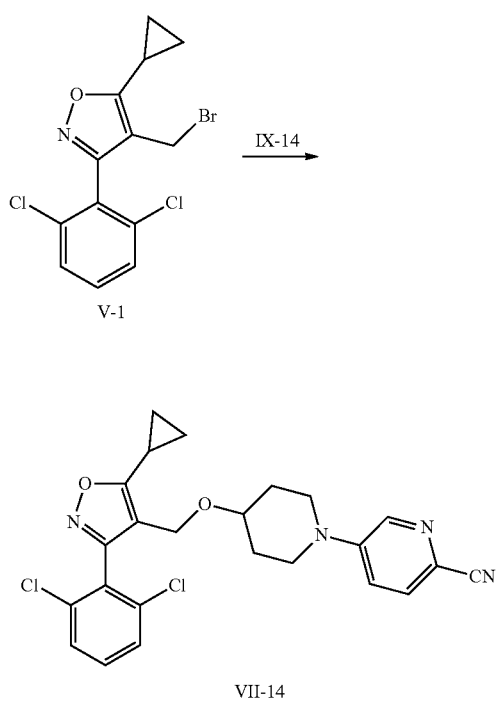

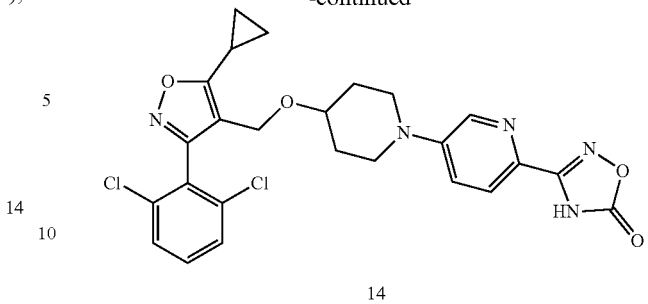

14

Compound intermediate IX-14 was synthesized from 4-hydroxypiperidine as the raw material according to the synthesis method of compound IX-10, white solid, yield 91%; $^1$H NMR (400 MHz, CDCl$_3$) δ 8.26 (d, J=3.0 Hz, 1H), 7.47 (d, J=8.8 Hz, 1H), 7.09 (dd, J=8.8, 3.0 Hz, 1H), 4.03-3.95 (m, 1H), 3.76-3.65 (m, 2H), 3.25-3.14 (m, 2H), 2.04-1.94 (m, 2H), 1.73-1.60 (m, 2H).

Compound intermediate VII-14 was synthesized from V-1 as the raw material according to the synthesis method of compound VII-1, white solid, yield 71%; $^1$H NMR (400 MHz. CDCl$_3$) δ 8.27 (d, J=2.7 Hz, 1H), 7.50 (d, J=8.9 Hz, 1H), 7.44-7.38 (m, 2H), 7.37-7.29 (m, 1H), 7.23-7.17 (m, 1H), 4.27 (s, 2H), 3.58-3.35 (m, 3H), 3.24-3.14 (m, 2H), 2.08-1.96 (m, 1H), 1.84-1.77 (m, 2H), 1.67-1.59 (m, 2H), 1.30-1.25 (m, 2H), 1.18-1.11 (m, 2H).

Compound 14 was synthesized from VII-14 as the raw material according to the synthesis method of compound 1, white solid, yield 55%; $^1$H NMR (400 MHz, CDCl$_3$) δ 8.29 (d, J=2.7 Hz, 1H), 7.89 (d, J=8.9 Hz, 1H), 7.44-7.39 (m, 2H), 7.33 (d, J=7.1 Hz, 1H), 7.23-7.17 (m, 1H), 4.37 (s, 2H), 3.58-3.48 (m, 1H), 3.42-3.35 (m, 2H), 3.20-3.13 (m, 2H), 2.20-2.12 (m, 1H), 1.84-1.77 (m, 2H), 1.64-1.57 (m, 2H), 1.30-1.27 (m, 2H), 1.18-1.12 (m, 2H). MS (ESI, m/z): 528 [M+H]$^+$.

Example 15

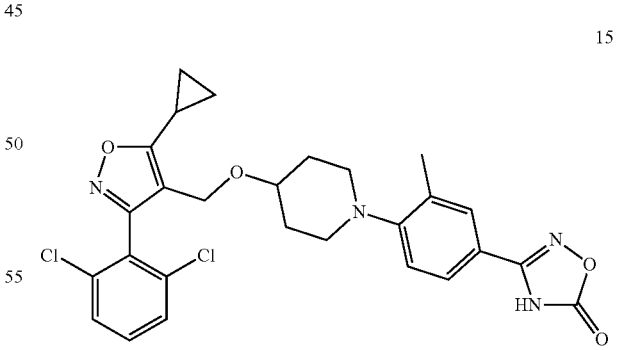

15

The synthetic route of example 15 was as follows.

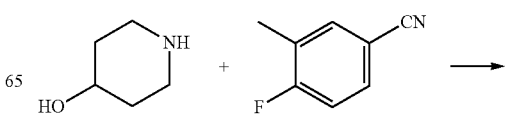

-continued

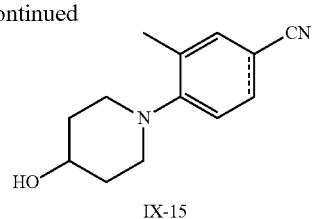

IX-15

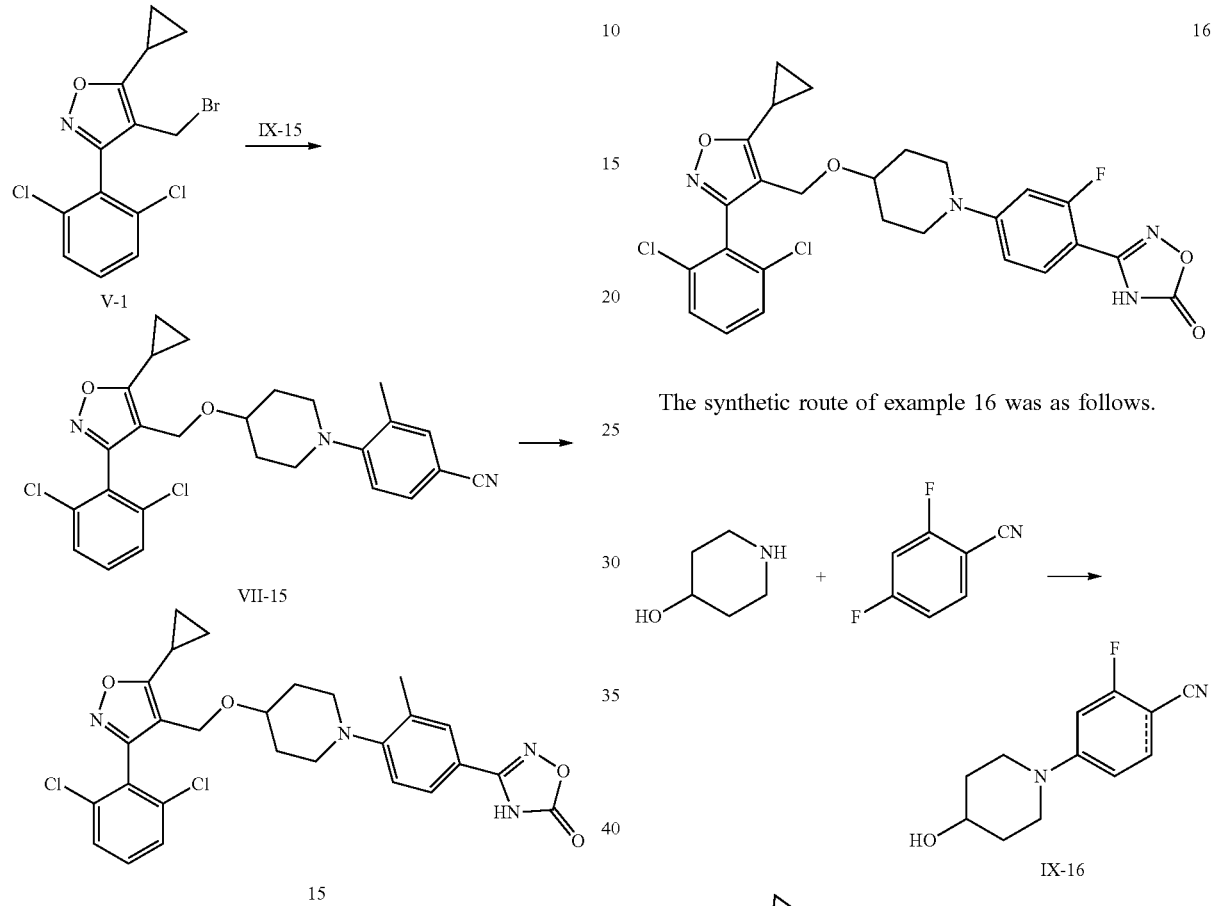

Compound intermediate IX-15 was synthesized from 4-hydroxypiperidine as the raw material according to the synthesis method of compound IX-10, white solid, yield 78%; $^1$H NMR (400 MHz, CDCl$_3$) δ 7.41-7.34 (m, 2H), 6.96 (d, J=8.9 Hz, 1H), 3.90-3.80 (m, 1H), 3.18-3.10 (m, 2H), 2.78-2.70 (m, 2H), 2.26 (s, 3H), 2.03-1.97 (m, 2H), 1.77-1.67 (m, 2H).

Compound intermediate VII-15 was synthesized from V-1 as the raw material according to the synthesis method of compound VII-1, white solid, yield 62%; $^1$H NMR (400 MHz, CDCl$_3$) δ 7.38-7.33 (m, 4H), 7.30-7.25 (m, 1H), 6.87 (d, J=8.2 Hz, 1H), 4.32 (s, 2H), 3.43-3.34 (m, 1H), 2.94-2.85 (m, 2H), 2.65-2.56 (m, 2H), 2.20 (s, 3H), 2.16-2.09 (m, 1H), 1.82-1.74 (m, 2H), 1.61-1.52 (m, 2H), 1.22-1.18 (m, 2H), 1.11-1.05 (m, 2H).

Compound 15 was synthesized from VII-15 as the raw material according to the synthesis method of compound 1, white solid, yield 65%; $^1$H NMR (400 MHz, CDCl$_3$) δ 7.62 (d, J=1.7 Hz, 1H), 7.59-7.54 (m, 1H), 7.46-7.42 (m, 2H), 7.38-7.32 (m, 1H), 7.00 (d, J=8.4 Hz, 1H), 4.38 (s, 2H), 3.48-3.39 (m, 1H), 3.03-2.94 (m, 2H), 2.72-2.64 (m, 2H), 2.31 (s, 3H), 2.22-2.15 (m, 1H), 1.89-1.80 (m, 2H), 1.69-1.58 (m, 2H), 1.31-1.28 (m, 2H), 1.18-1.13 (m, 2H). MS (ESI, m/z): 541 [M+H]$^+$.

Example 16

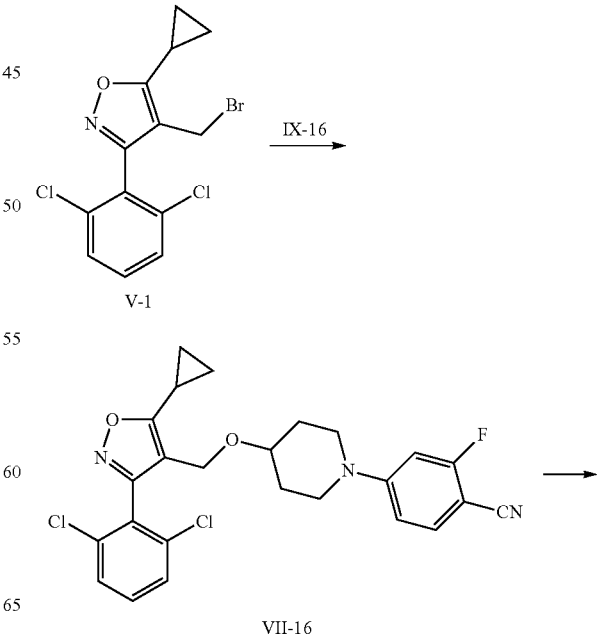

The synthetic route of example 16 was as follows.

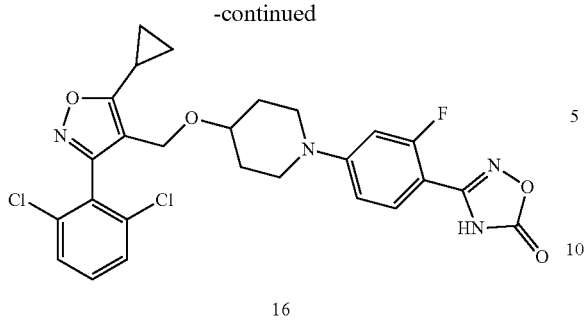

16

Compound intermediate IX-16 was synthesized from 4-hydroxypiperidine as the raw material according to the synthesis method of compound IX-10, white solid, yield 78%; $^1$H NMR (400 MHz, CDCl$_3$) δ 7.38-7.30 (m, 1H), 6.67-6.49 (m, 2H), 4.02-3.91 (m, 1H), 3.78-3.57 (m, 2H), 3.26-3.04 (m, 2H), 2.01-1.88 (m, 2H), 1.68-1.55 (m, 2H).

Compound intermediate VII-16 was synthesized from V-1 as the raw material according to the synthesis method of compound VII-1, white solid, yield 67%; $^1$H NMR (400 MHz, CDCl$_3$) δ 7.41-7.37 (m, 2H), 7.37-7.28 (m, 2H), 6.59-6.45 (m, 2H), 4.34 (s, 2H), 3.55-3.47 (m, 1H), 3.37-3.28 (m, 2H), 3.16-3.05 (m, 2H), 2.19-2.10 (m, 1H), 1.78-1.70 (m, 2H), 1.59-1.48 (m, 2H), 1.28-1.22 (m, 2H), 1.16-1.10 (m, 2H).

Compound 16 was synthesized from VII-16 as the raw material according to the synthesis method of compound 1, white solid, yield 61%; $^1$H NMR (400 MHz, CDCl$_3$) δ 10.12 (s, 1H), 7.71 (t, J=8.8 Hz, 1H), 7.44-7.38 (m, 2H), 7.35-7.30 (m, 1H), 6.68 (dd, J=9.1, 2.2 Hz, 1H), 6.53 (dd, J=15.5, 2.2 Hz, 1H), 4.36 (s, 2H), 3.56-3.47 (m, 1H), 3.39-3.31 (m, 2H), 3.16-3.07 (m, 2H), 2.21-2.11 (m, 1H), 1.81-1.74 (m, 2H), 1.62-1.51 (m, 2H), 1.32-1.27 (m, 2H), 1.18-1.11 (m, 2H). MS (ESI, m/z): 545 [M+H]$^+$.

Example 17

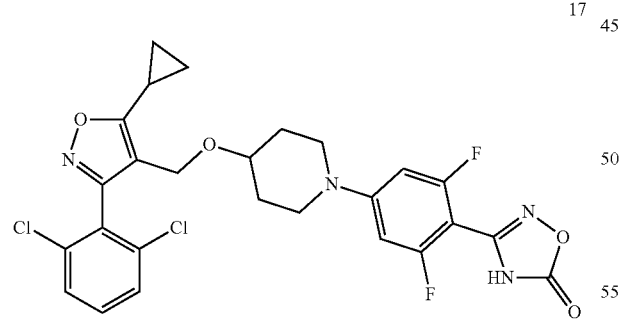

17

The synthetic route of example 17 was as follows.

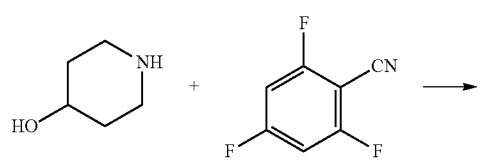

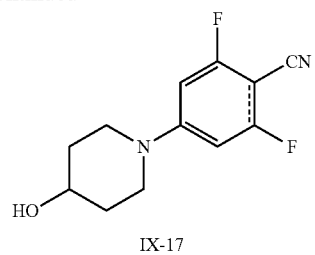

IX-17

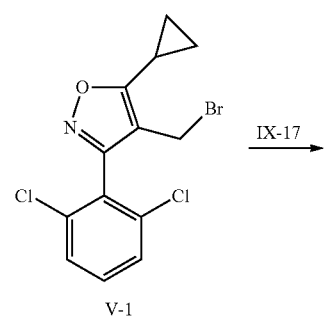

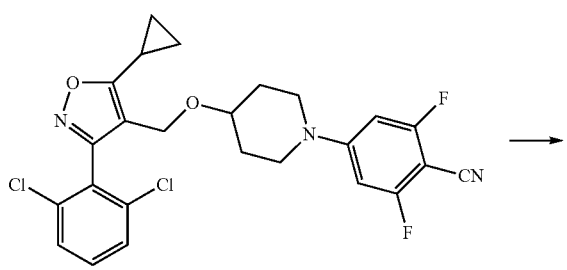

VII-17

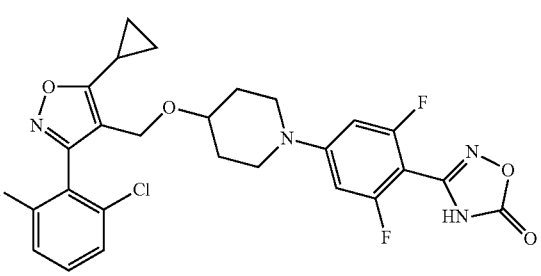

17

Compound intermediate IX-17 was synthesized from 4-hydroxypiperidine as the raw material according to the synthesis method of compound IX-10, white solid, yield 55%; $^1$H NMR (400 MHz, CDCl$_3$) δ 6.43-6.32 (m, 2H), 4.08-3.98 (m, 1H), 3.71-3.62 (m, 2H), 3.27-3.17 (m, 2H), 2.02-1.94 (m, 2H), 1.70-1.61 (m, 2H).

Compound intermediate VII-17 was synthesized from V-1 as the raw material according to the synthesis method of compound VII-1, white solid, yield 67%; ¹H NMR (400 MHz, CDCl₃) δ 7.43-7.39 (m, 2H), 7.36-7.30 (m, 1H), 6.34-6.27 (m, 2H), 4.35 (s, 2H), 3.60-3.50 (m, 1H), 3.35-3.26 (m, 2H), 3.19-3.08 (m, 2H), 2.18-2.10 (m, 1H), 1.74-1.68 (m, 2H), 1.59-1.50 (m, 2H), 1.28-1.25 (m, 2H), 1.17-1.11 (m, 2H).

Compound 17 was synthesized from VII-16 as the raw material according to the synthesis method of compound 1, white solid, yield 73%; ¹H NMR (400 MHz, CDCl₃) δ 7.45-7.39 (m, 2H), 7.37-7.31 (m, 1H), 6.40 (d, J=13.5 Hz, 2H), 4.36 (s, 2H), 3.58-3.48 (m, 1H), 3.36-3.27 (m, 2H), 3.18-3.07 (m, 2H), 2.22-2.10 (m, 1H), 1.79-1.70 (m, 2H), 1.61-1.52 (m, 2H), 1.30-1.26 (m, 2H), 1.18-1.12 (m, 2H). MS (ESI, m/z): 563 [M+H]⁺.

Example 18

18

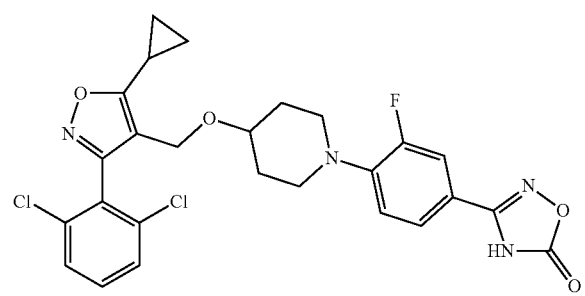

The synthetic route of example 18 was as follows.

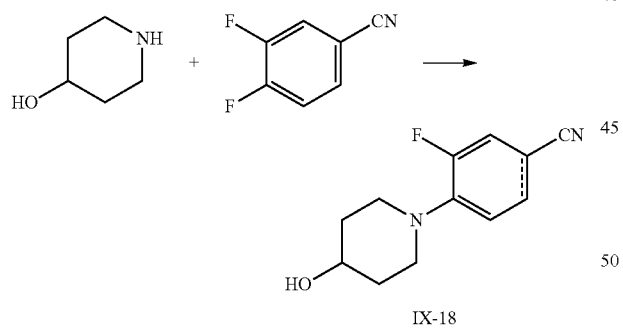

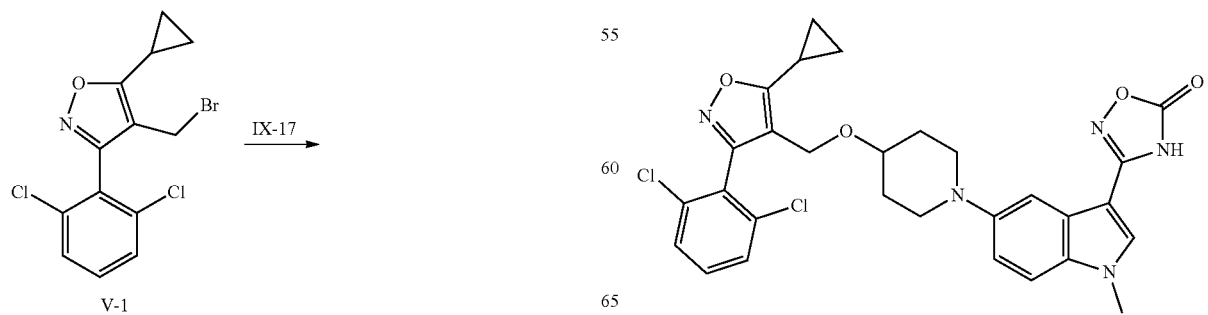

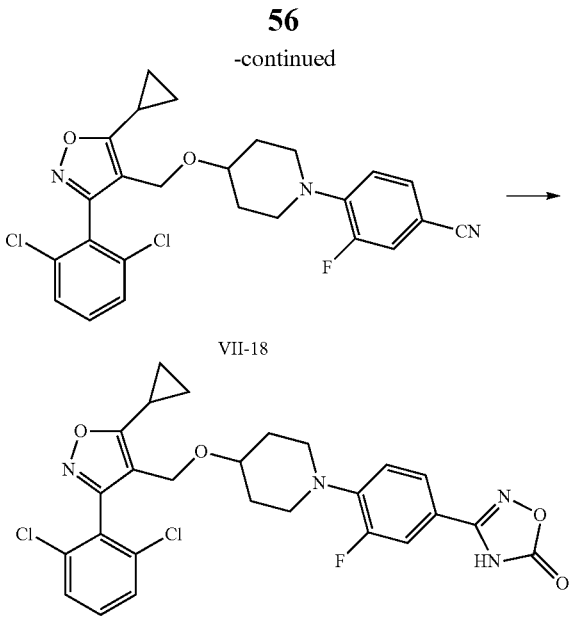

Compound intermediate IX-18 was synthesized from 4-hydroxypiperidine as the raw material according to the synthesis method of compound IX-10, white solid, yield 61%; ¹H NMR (400 MHz, DMSO) δ 7.62-7.47 (m, 2H), 7.08 (t, J=8.8 Hz, 1H), 3.71-3.62 (m, 1H), 3.43-3.37 (m, 2H), 3.01-2.79 (m, 2H), 1.92-1.74 (m, 2H), 1.57-1.42 (m, 2H).

Compound intermediate VII-18 was synthesized from V-1 as the raw material according to the synthesis method of compound VII-1, white solid, yield 63%; ¹H NMR (400 MHz, CDCl₃) δ 7.43-7.38 (m, 2H), 7.35-7.28 (m, 2H), 7.26-7.21 (m, 1H), 6.86 (t, J=8.6 Hz, 1H), 4.35 (s, 2H), 3.49-3.41 (m, 1H), 3.26-3.15 (m, 2H), 2.96-2.86 (m, 2H), 2.20-2.12 (m, 1H), 1.86-1.77 (m, 2H), 1.65-1.55 (m, 2H), 1.30-1.26 (m, 2H), 1.16-1.09 (m, 2H).

Compound 18 was synthesized from VII-16 as the raw material according to the synthesis method of compound 1, white solid, yield 65%; ¹H NMR (400 MHz, CDCl₃) δ 7.50-7.39 (m, 4H), 7.36-7.30 (m, 1H), 6.94 (t, J=8.5 Hz, 1H), 4.37 (s, 2H), 3.55-3.42 (m, 1H), 3.33-3.17 (m, 2H), 3.00-2.84 (m, 2H), 2.22-2.13 (m, 1H), 1.89-1.80 (m, 2H), 1.69-1.58 (m, 2H), 1.32-1.26 (m, 2H), 1.19-1.12 (m, 2H). MS (ESI, m/z): 545 [M+H]⁺.

Example 19

19

The synthetic route of example 19 was as follows.

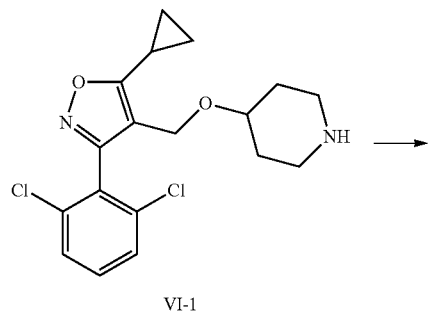

VI-1

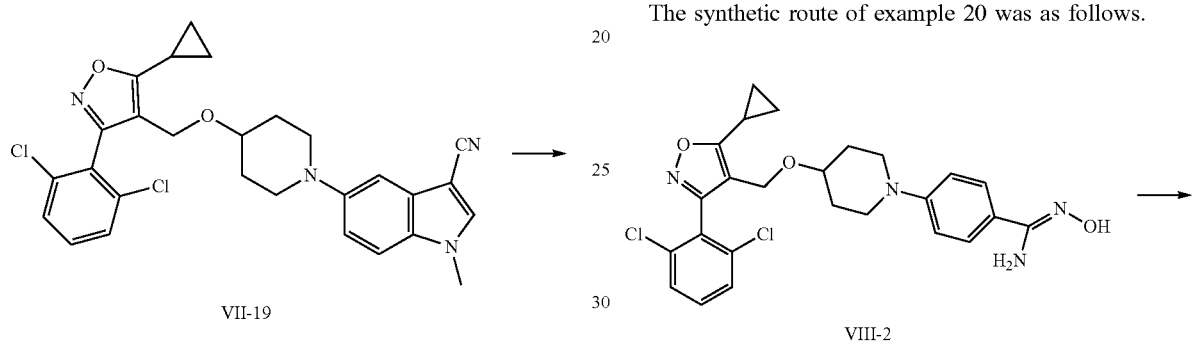

VII-19

19

Compound intermediate VII-19 was synthesized from VI-1 as the raw material according to the synthesis method of compound VII-1, white solid, yield 37%; $^1$H NMR (400 MHz, CDCl$_3$) δ 7.67 (s, 1H), 7.56 (s, 1H), 7.37 (d, J=7.9 Hz, 2H), 7.29-7.23 (m, 1H), 7.09 (d, J=8.9 Hz, 1H), 6.93 (d, J=8.9 Hz, 1H), 4.31 (s, 2H), 3.52 (s, 3H), 3.37-3.27 (m, 1H), 3.24-3.14 (m, 2H), 2.83-2.71 (m, 2H), 2.20-2.09 (m, 1H), 1.86-1.75 (m, 2H), 1.63-1.52 (m, 2H), 1.26-1.18 (m, 2H), 1.12-1.07 (m, 2H).

Compound 19 was synthesized from VII-19 as the raw material according to the synthesis method of compound 1, white solid, yield 29%; $^1$H NMR (400 MHz, DMSO-d6) δ 7.81 (s, 1H), 7.63 (d, J=7.7 Hz, 2H), 7.55-7.50 (m, 1H), 7.43 (d, J=9.0 Hz, 1H), 7.28 (s, 1H), 7.04 (d, J=9.0 Hz, 1H), 4.33 (s, 2H), 3.83 (s, 3H), 3.35 (s, 1H), 3.09 (s, 2H), 2.80-2.72 (m, 2H), 2.04-1.95 (m, 1H), 1.75 (s, 2H), 1.50-1.41 (m, 2H), 1.20-1.07 (m, 4H). MS (ESI, m/z): 580 [M+H]$^+$.

Example 20

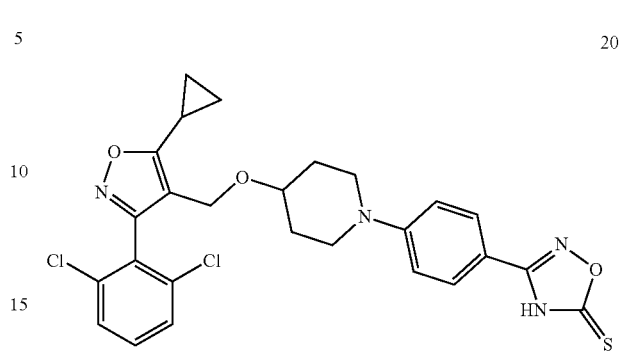

The synthetic route of example 20 was as follows.

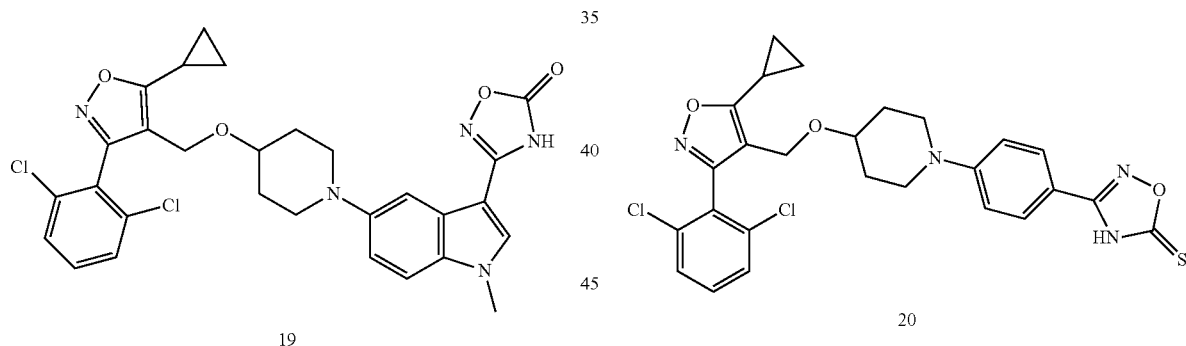

VIII-2

20

VIII-2 (0.41 g, 0.83 mmol), N,N'-thiocarbonyldiimidazole (1.0 mmol) and 1,4-dioxane (4 mL) were added into a round bottom flask, and then 1,8-diazabicyclic[5.4.0]undecarbon-7-ene (0.91 mmol) was heated to 100° C. and reacted for 3 hours. The reaction solution was cooled to room temperature, diluted with water (5 mL), adjusted to pH approximately equal to 2 with a 1M aqueous hydrochloric acid solution, and then extracted with ethyl acetate (4 mL each time, 3 times in total). The organic phases were combined, washed with saturated brine, concentrated and the crude product obtained was subjected to silica gel column chromatography to obtain the final product 20 (0.22 g, yield 49%). $^1$H NMR (400 MHz, CDCl$_3$) δ 7.44-7.37 (m, 3H), 7.34-7.30 (m, 1H), 6.89 (d, J=8.9 Hz, 2H), 4.36 (s, 2H), 3.44-3.37 (m, 1H), 3.24-3.14 (m, 2H), 2.83-2.73 (m, 2H), 2.21-2.14 (m, 1H), 1.81-1.76 (m, 2H), 1.61-1.54 (m, 2H), 1.32-1.26 (m, 2H), 1.17-1.09 (m, 2H). MS (ESI, m/z): 543 [M+H]$^+$.

Example 21

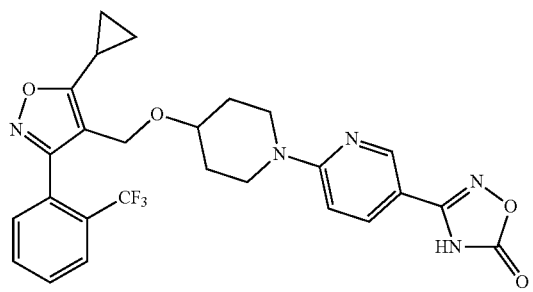

The synthetic route of example 21 was as follows.

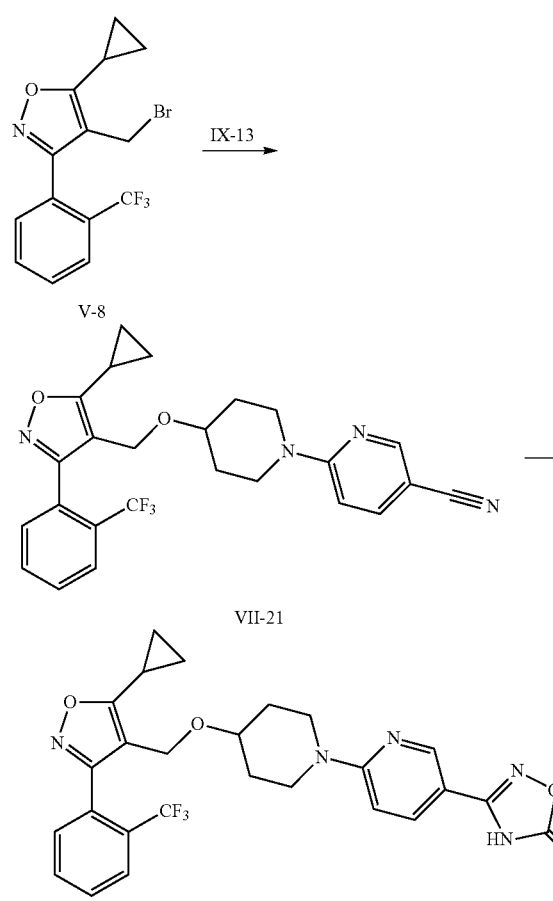

Compound intermediate VII-21 was synthesized from V-8 and IX-13 as the raw materials according to the synthesis method of compound VII-10, white solid, yield 62%; $^1$H NMR (400 MHz, CDCl$_3$) δ 8.37 (d, J=1.1 Hz, 1H), 7.79 (d, J=7.8 Hz, 1H), 7.66-7.53 (m, 3H), 7.46 (d, J=6.8 Hz, 1H), 6.57 (d, J=9.1 Hz, 1H), 4.28 (s, 2H), 3.80-3.71 (m, 2H), 3.54-3.46 (m, 1H), 3.41-3.33 (m, 2H), 2.16-2.08 (m, 1H), 1.79-1.70 (m, 2H), 1.55-1.45 (m, 2H), 1.26-1.21 (m, 2H), 1.14-1.08 (m, 2H).

Compound 21 was synthesized from VII-21 as the raw material according to the synthesis method of compound 1, white solid, yield 69%; $^1$H NMR (400 MHz, DMSO) δ 8.46 (d, J=2.1 Hz, 1H), 7.86 (d, J=7.8 Hz, 1H), 7.81-7.72 (m, 2H), 7.68 (t, J=7.6 Hz, 1H), 7.58 (d, J=7.6 Hz, 1H), 6.85 (d, J=9.2 Hz, 1H), 4.28 (s, 2H), 3.81-3.70 (m, 2H), 3.45 (s, 1H), 3.25 (t, J=9.4 Hz, 2H), 2.33-2.23 (m, 1H), 1.75-1.61 (m, 2H), 1.38-1.25 (m, 2H), 1.17-1.04 (m, 4H). MS (ESI, m/z): 528 [M+H]$^+$.

Example 22

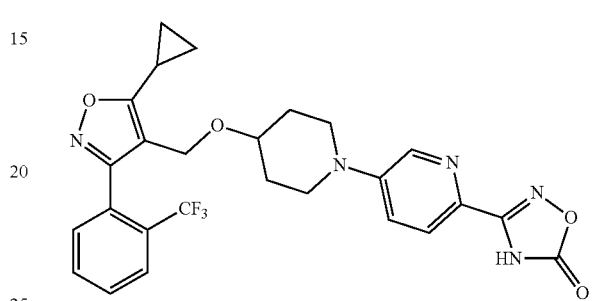

The synthetic route of example 22 was as follows.

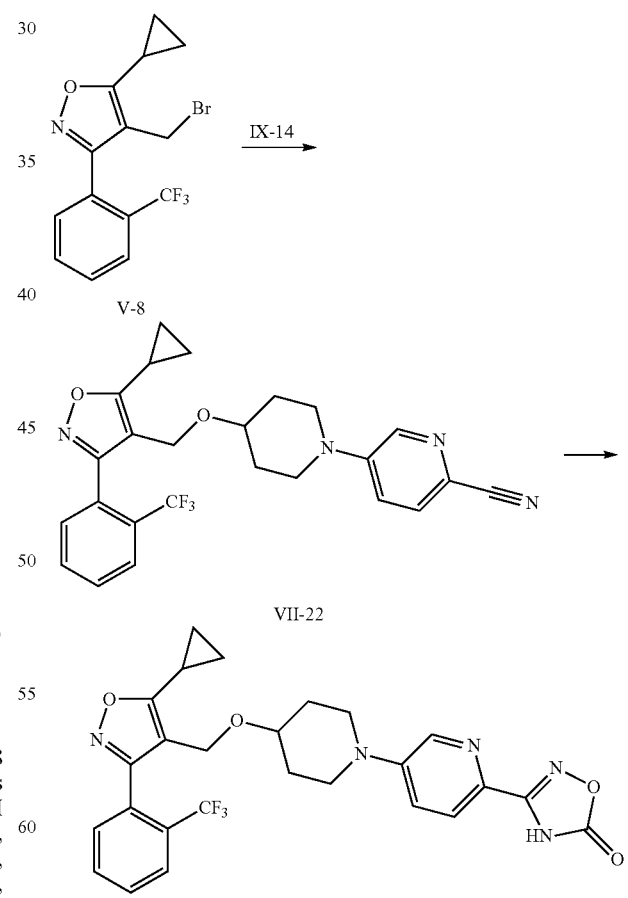

Compound intermediate VII-22 was synthesized from V-8 and IX-14 as the raw materials according to the synthesis method of compound VII-10, white solid, yield 71%; ¹H NMR (400 MHz, CDCl₃) δ 8.23 (d, J=2.7 Hz, 1H), 7.78 (d, J=7.2 Hz, 1H), 7.62-7.53 (m, 2H), 7.49-7.43 (m, 2H), 7.03 (dd, J=8.8, 2.7 Hz, 1H), 4.28 (s, 2H), 3.53-3.46 (m, 1H), 3.43-3.36 (m, 2H), 3.18-3.10 (m, 2H), 2.15-2.07 (m, 1H), 1.83-1.75 (m, 2H), 1.62-1.52 (m, 2H), 1.24-1.20 (m, 2H), 1.15-1.09 (m, 2H).

Compound 22 was synthesized from VII-22 as the raw material according to the synthesis method of compound 1, white solid, yield 66%; ¹H NMR (400 MHz, DMSO) δ 8.33 (d, J=2.3 Hz, 1H), 7.85 (d, J=7.7 Hz, 1H), 7.78-7.64 (m, 3H), 7.59 (d, J=7.5 Hz, 1H), 7.32 (dd, J=9.0, 2.3 Hz, 1H), 4.29 (s, 2H), 3.50-3.36 (m, 3H), 3.06 (t, J=9.1 Hz, 2H), 2.34-2.23 (m, 1H), 1.79-1.68 (m, 2H), 1.46-1.33 (m, 2H), 1.14-1.04 (m, 4H). MS (ESI, m/z): 528 [M+H]⁺.

Example 23

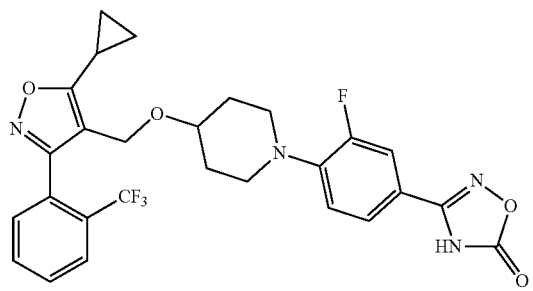

23

The synthetic route of example 23 was as follows.

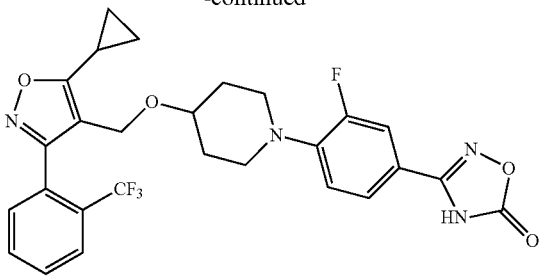

23

Compound intermediate VII-23 was synthesized from V-8 and IX-18 as the raw materials according to the synthesis method of compound VII-10, white solid, yield 70%; ¹H NMR (400 MHz, CDCl₃) δ 7.84-7.79 (m, 1H), 7.66-7.56 (m, 2H), 7.49 (d, J=6.8 Hz, 1H), 7.35 (dd, J=8.4, 1.3 Hz, 1H), 7.28-7.24 (m, 1H), 6.87 (t, J=8.4 Hz, 1H), 4.29 (s, 2H), 3.49-3.38 (m, 1H), 3.32-3.23 (m, 2H), 2.97-2.88 (m, 2H), 2.18-2.09 (m, 1H), 1.90-1.82 (m, 2H), 1.68-1.59 (m, 2H), 1.29-1.25 (m, 2H), 1.17-1.10 (m, 2H).

Compound 23 was synthesized from VII-23 as the raw material according to the synthesis method of compound 1, white solid, yield 61%; ¹H NMR (400 MHz, DMSO) δ 7.91 (d, J=7.7 Hz, 1H), 7.83-7.70 (m, 2H), 7.60 (d, J=7.5 Hz, 1H), 7.56-7.47 (m, 2H), 7.14-7.07 (m, 1H), 4.29 (s, 2H), 3.44-3.33 (m, 1H), 3.18-3.09 (m, 2H), 2.88-2.79 (m, 2H), 2.37-2.29 (m, 1H), 1.82-1.73 (m, 2H), 1.50-1.39 (m, 2H), 1.18-1.06 (m, 4H). MS (ESI, m/z): 545 [M+H]⁺.

Example 24

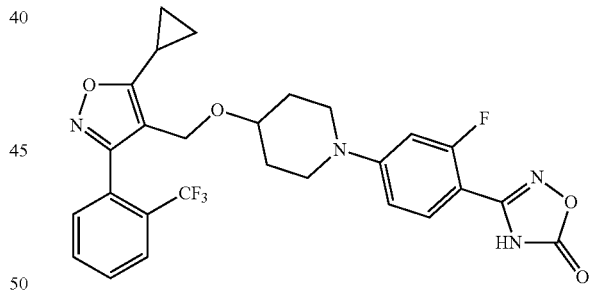

24

The synthetic route of example 24 was as follows.

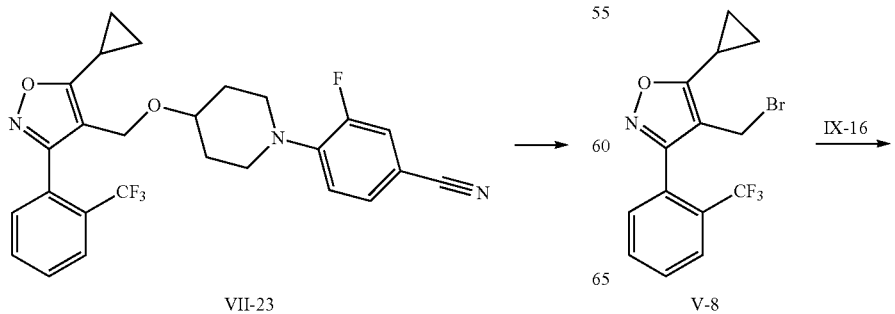

-continued

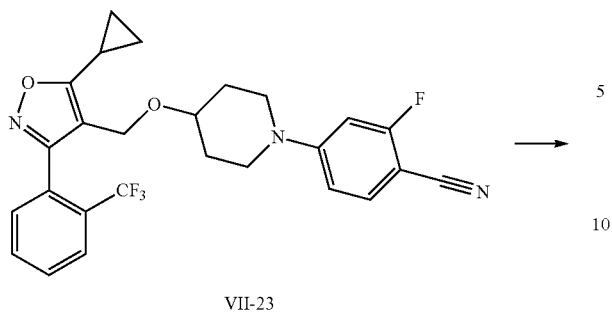

VII-23

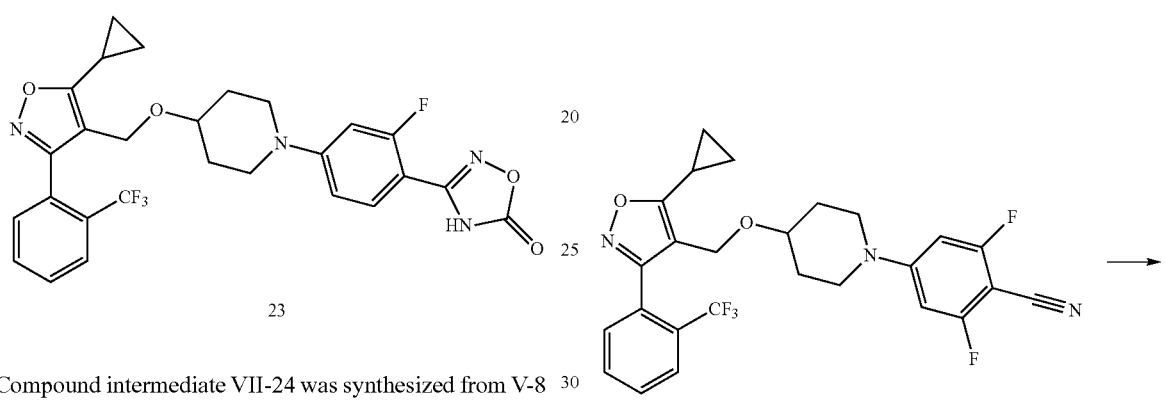

23

Compound intermediate VII-24 was synthesized from V-8 and IX-16 as the raw materials according to the synthesis method of compound VII-10, white solid, yield 70%; $^1$H NMR (400 MHz, CDCl$_3$) δ 7.82-7.75 (m, 1H), 7.64-7.54 (m, 2H), 7.47-7.43 (m, 1H), 7.38-7.31 (m, 1H), 6.57 (dd, J=8.9, 2.4 Hz, 1H), 6.48 (dd, J=13.3, 2.4 Hz, 1H), 4.28 (s, 2H), 3.52-3.45 (m, 1H), 3.43-3.34 (m, 2H), 3.15-3.04 (m, 2H), 2.16-2.07 (m, 1H), 1.83-1.72 (m, 2H), 1.59-1.49 (m, 2H), 1.25-1.20 (m, 2H), 1.15-1.09 (m, 2H).

Compound 24 was synthesized from VII-24 as the raw material according to the synthesis method of compound 1, white solid, yield 61%; $^1$H NMR (400 MHz, DMSO) δ 7.89 (d, J=7.7 Hz, 1H), 7.81-7.68 (m, 2H), 7.59 (d, J=7.5 Hz, 1H), 7.52 (t, J=8.9 Hz, 1H), 6.85 (dd, J=10.2, 7.5 Hz, 2H), 4.28 (s, 2H), 3.48-3.39 (m, 3H), 3.11-3.00 (m, 2H), 2.38-2.27 (m, 1H), 1.75-1.65 (m, 2H), 1.39-1.27 (mS, 2H), 1.17-1.05 (m, 4H). MS (ESI, m/z): 545 [M+H]$^+$.

Example 25

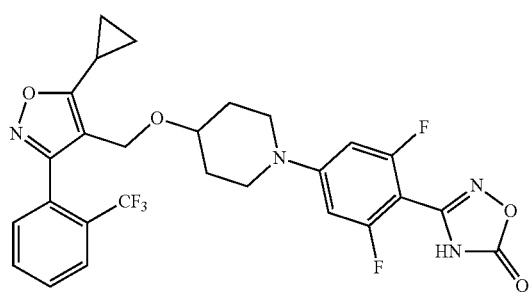

The synthetic route of example 25 was as follows.

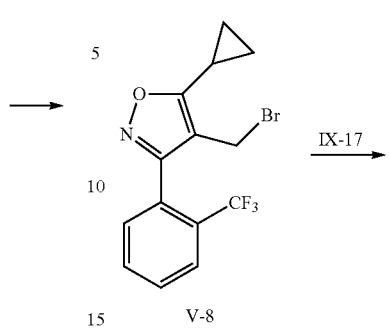

V-8

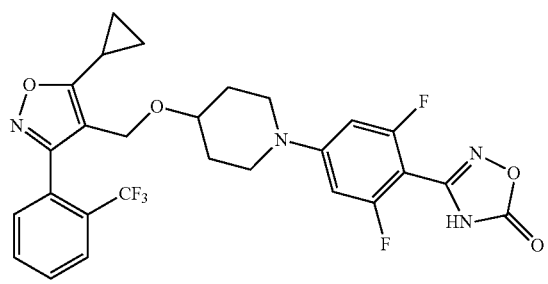

VII-25

Compound intermediate VII-25 was synthesized from V-8 and IX-17 as the raw materials according to the synthesis method of compound VII-10, white solid, yield 59%; $^1$H NMR (400 MHz, CDCl$_3$) δ 7.79-7.76 (m, 1H), 7.64-7.54 (m, 2H), 7.47-7.43 (m, 1H), 6.30 (d, J=11.7 Hz, 2H), 4.27 (s, 2H), 3.54-3.46 (m, 1H), 3.40-3.30 (m, 2H), 3.18-3.06 (m, 2H), 2.16-2.05 (m, 1H), 1.82-1.70 (m, 2H), 1.57-1.49 (m, 2H), 1.23-1.18 (m, 2H), 1.14-1.07 (m, 2H).

Compound 25 was synthesized from VII-25 as the raw material according to the synthesis method of compound 1, white solid, yield 64%; $^1$H NMR (400 MHz, DMSO) δ 7.89 (d, J=7.7 Hz, 1H), 7.80-7.68 (m, 2H), 7.60 (d, J=7.4 Hz, 1H), 6.77 (d, J=13.3 Hz, 2H), 4.29 (s, 2H), 3.50-3.38 (m, 3H), 3.18-3.03 (m, 2H), 2.37-2.25 (m, 1H), 1.78-1.64 (m, 2H), 1.43-1.27 (m, 2H), 1.20-1.03 (m, 4H). MS (ESI, m/z): 563 [M+H]$^+$.

Example 26

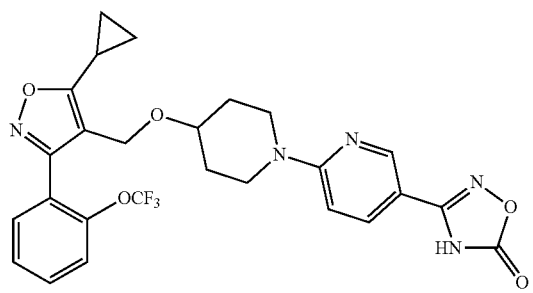

The synthetic route of example 26 was as follows.

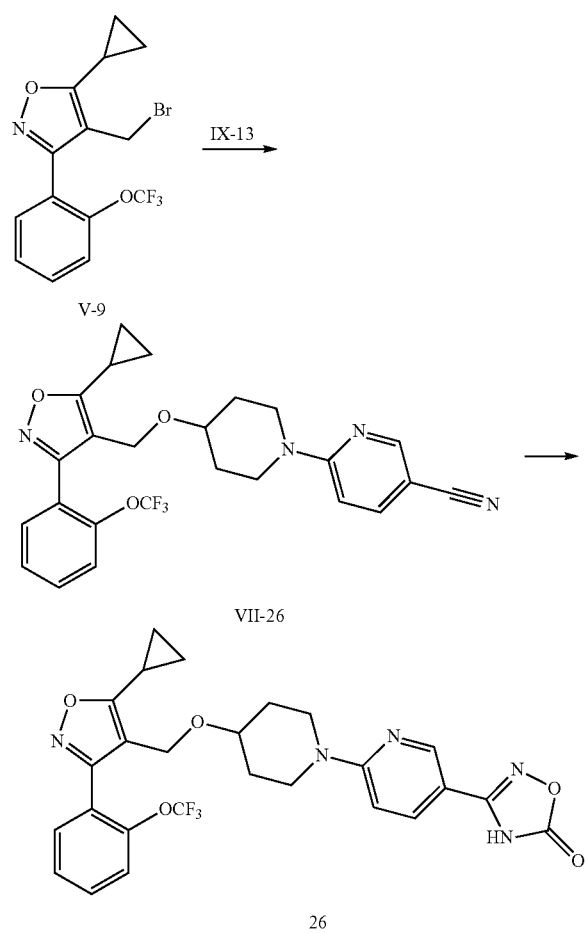

Compound intermediate VII-26 was synthesized from V-9 and IX-13 as the raw materials according to the synthesis method of compound VII-10, white solid, yield 67%; $^1$H NMR (400 MHz, CDCl$_3$) δ 8.37 (s, 1H), 7.60-7.47 (m, 3H), 7.41-7.34 (m, 2H), 6.57 (d, J=9.1 Hz, 1H), 4.41 (s, 2H), 3.85-3.73 (m, 2H), 3.60-3.50 (m, 1H), 3.43-3.32 (m, 2H), 2.19-2.09 (m, 1H), 1.81-1.73 (m, 2H), 1.57-1.47 (m, 2H), 1.25-1.20 (m, 2H), 1.14-1.07 (m, 2H).

Compound 26 was synthesized from VII-26 as the raw material according to the synthesis method of compound 1, white solid, yield 68%; $^1$H NMR (400 MHz, DMSO) δ 8.46 (d, J=2.3 Hz, 1H), 7.80 (dd, J=9.1, 2.3 Hz, 1H), 7.69-7.61 (m, 2H), 7.57-7.49 (m, 2H), 6.92 (d, J=9.2 Hz, 1H), 4.38 (s, 2H), 3.88-3.75 (m, 2H), 3.57-3.47 (m, 1H), 3.32-3.21 (m, 2H), 2.37-2.27 (m, 1H), 1.77-1.67 (m, 2H), 1.38-1.27 (m, 2H), 1.16-1.05 (m, 4H). MS (ESI, m/z): 544 [M+H]$^+$.

Example 27

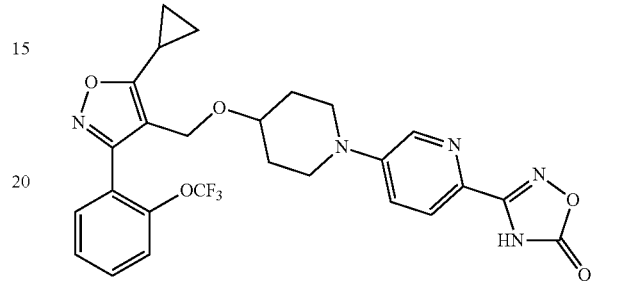

The synthetic route of example 27 was as follows.

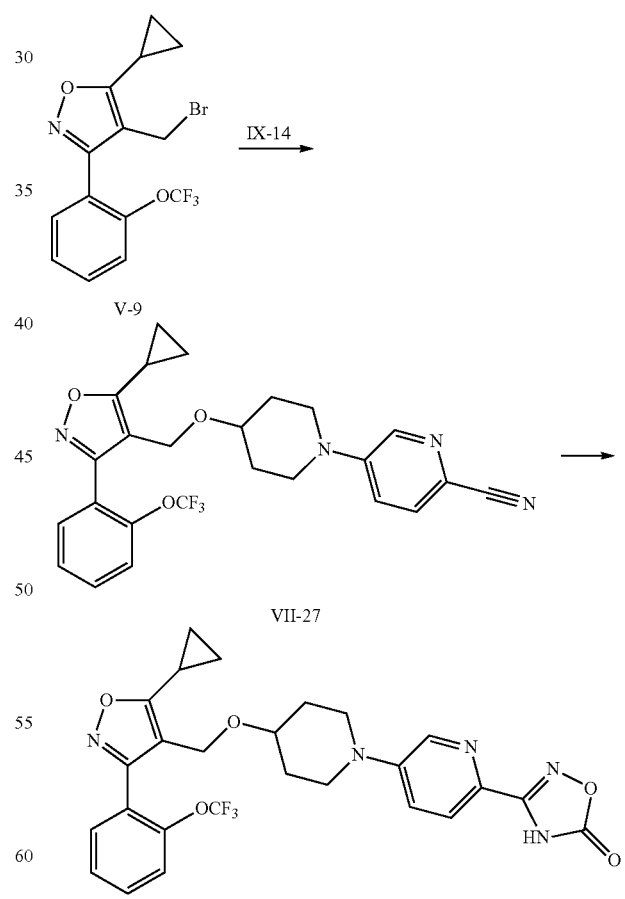

Compound intermediate VII-27 was synthesized from V-9 and IX-14 as the raw materials according to the synthesis method of compound VII-10, white solid, yield 74%; $^1$H NMR (400 MHz, CDCl₃) δ 8.23 (s, 1H), 7.58-7.43 (m, 3H), 7.37 (d, J=7.8 Hz, 2H), 7.03 (dd, J=8.8, 2.7 Hz, 1H), 4.40 (s, 2H), 3.57-3.50 (m, 1H), 3.48-3.38 (m, 2H), 3.19-3.09 (m, 2H), 2.17-2.08 (m, 1H), 1.87-1.75 (m, 2H), 1.65-1.54 (m, 2H), 1.24-1.18 (m, 2H), 1.13-1.07 (m, 2H).

Compound 27 was synthesized from VII-27 as the raw material according to the synthesis method of compound 1, white solid, yield 61%; ¹H NMR (400 MHz, DMSO) δ 8.34 (d, J=2.4 Hz, 1H), 7.71 (d, J=8.9 Hz, 1H), 7.67-7.58 (m, 2H), 7.52-7.46 (m, 2H), 7.33 (dd, J=8.9, 2.1 Hz, 1H), 4.38 (s, 2H), 3.56-3.42 (m, 3H), 3.07 (t, J=9.3 Hz, 2H), 2.34-2.23 (m, 1H), 1.83-1.72 (m, 2H), 1.49-1.37 (m, 2H), 1.14-1.03 (m, 4H). MS (ESI, m/z): 544 [M+H]⁺.

Example 28

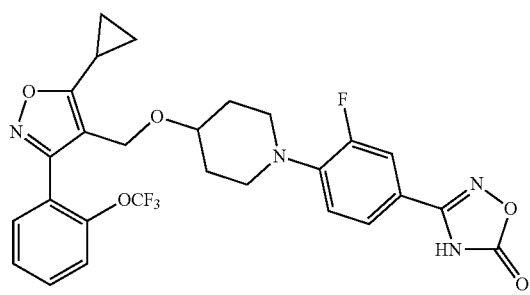

28

The synthetic route of example 28 was as follows.

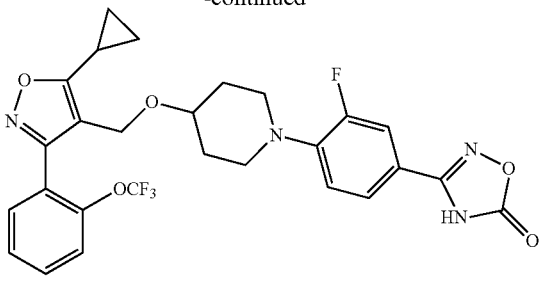

28

Compound intermediate VII-28 was synthesized from V-9 and IX-18 as the raw materials according to the synthesis method of compound VII-10, white solid, yield 67%; ¹H NMR (400 MHz, CDCl₃) δ 7.60-7.56 (m, 1H), 7.55-7.49 (m, 1H), 7.41-7.37 (m, 2H), 7.33 (d, J=8.4 Hz, 1H), 7.25 (d, J=12.7 Hz, 1H), 6.87 (t, J=8.6 Hz, 1H), 4.41 (s, 2H), 3.51-3.42 (m, 1H), 3.34-3.23 (m, 2H), 2.97-2.88 (m, 2H), 2.20-2.11 (m, 1H), 1.91-1.82 (m, 2H), 1.70-1.59 (m, 2H), 1.25-1.22 (m, 2H), 1.15-1.08 (m, 2H).

Compound 28 was synthesized from VII-28 as the raw material according to the synthesis method of compound 1, white solid, yield 72%; ¹H NMR (400 MHz, DMSO) δ 7.69-7.62 (m, 2H), 7.57-7.46 (m, 4H), 7.10 (t, J=8.7 Hz, 1H), 4.37 (s, 2H), 3.48-3.40 (m, 1H), 3.24-3.11 (m, 2H), 2.85 (t, J=9.2 Hz, 2H), 2.40-2.25 (m, 1H), 1.87-1.75 (m, 2H), 1.56-1.40 (m, 2H), 1.16-1.04 (m, 4H). MS (ESI, m/z): 561 [M+H]⁺.

Example 29

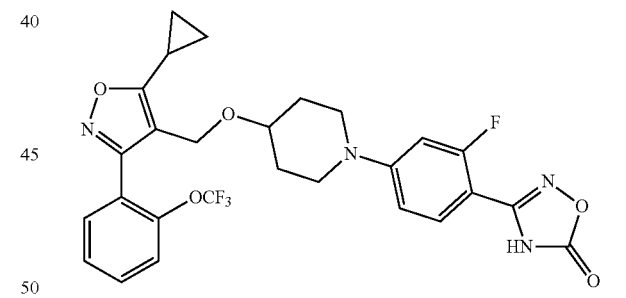

29

The synthetic route of example 29 was as follows:

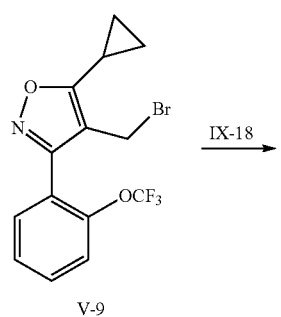

VII-28

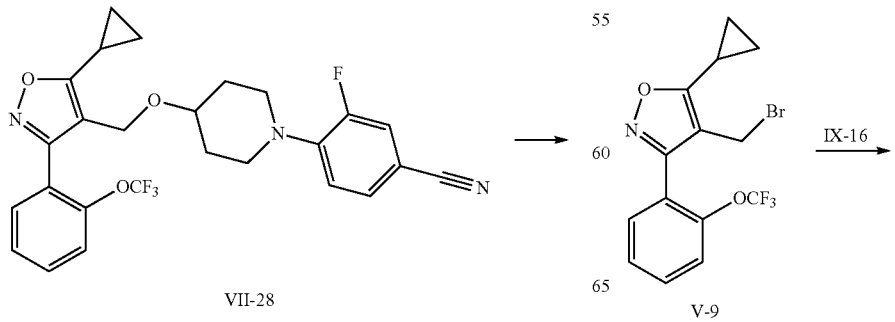

V-9

-continued

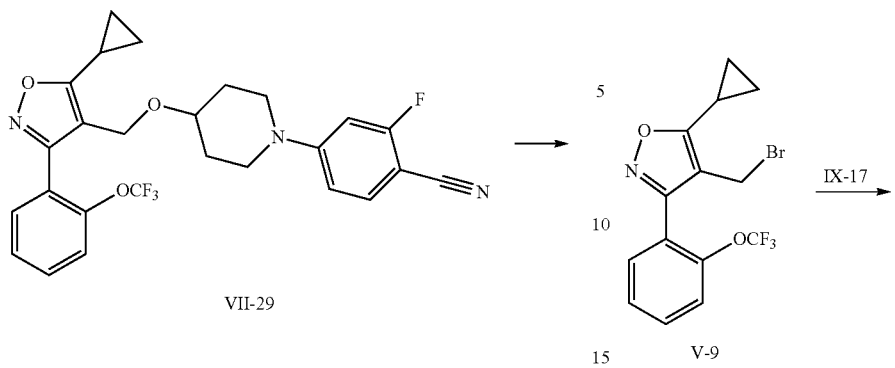

VII-29

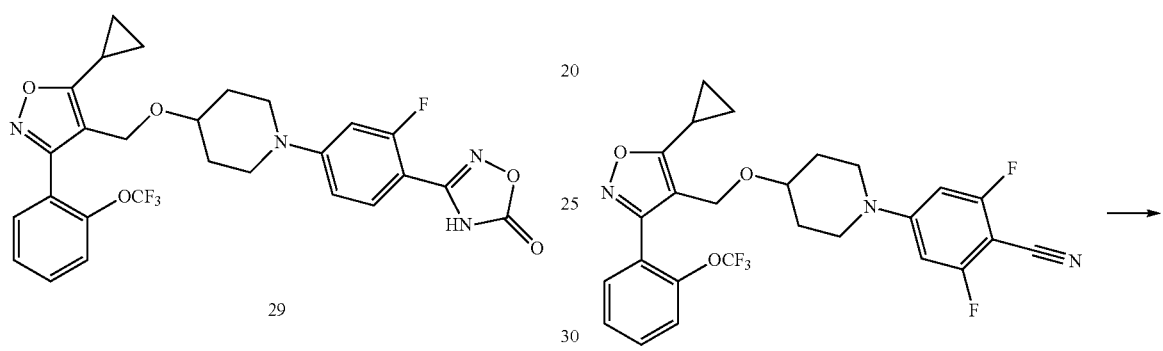

29

Compound intermediate VII-29 was synthesized from V-9 and IX-16 as the raw materials according to the synthesis method of compound VII-10, white solid, yield 72%; ¹H NMR (400 MHz, CDCl₃) δ 7.57-7.47 (m, 2H), 7.41-7.30 (m, 3H), 6.57 (dd, J=8.9, 2.4 Hz, 1H), 6.48 (dd, J=13.3, 2.4 Hz, 1H), 4.40 (s, 2H), 3.57-3.49 (m, 1H), 3.46-3.37 (m, 2H), 3.15-3.05 (m, 2H), 2.17-2.09 (m, 1H), 1.84-1.74 (m, 2H), 1.60-1.50 (m, 2H), 1.23-1.18 (m, 2H), 1.13-1.06 (m, 2H).

Compound 29 was synthesized from VII-29 as the raw material according to the synthesis method of compound 1, white solid, yield 60%; ¹H NMR (400 MHz, DMSO) δ 7.69-7.61 (m, 2H), 7.58-7.48 (m, 3H), 6.91-6.80 (m, 2H), 4.38 (s, 2H), 3.55-3.43 (m, 3H), 3.14-2.99 (m, 2H), 2.37-2.27 (m, 1H), 1.79-1.66 (m, 2H), 1.43-1.30 (m, 2H), 1.18-1.03 (m, 4H). MS (ESI, m/z): 561 [M+H]⁺.

Example 30

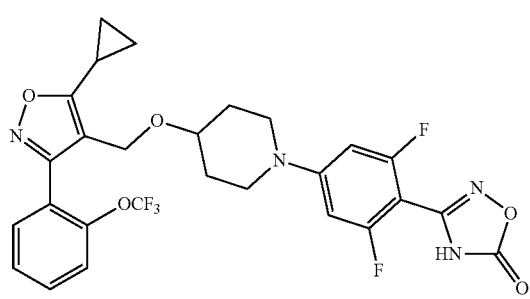

30

The synthetic route of example 30 was as follows.

V-9

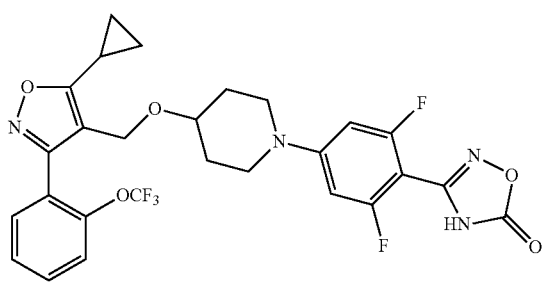

VII-30

Compound intermediate VII-30 was synthesized from V-9 and IX-17 as the raw materials according to the synthesis method of compound VII-10, white solid, yield 62%; ¹H NMR (400 MHz, CDCl₃) δ 7.57-7.49 (m, 2H), 7.42-7.35 (m, 2H), 6.31 (d, J=11.6 Hz, 2H), 4.41 (s, 2H), 3.59-3.51 (m, 1H), 3.42-3.34 (m, 2H), 3.19-3.08 (m, 2H), 2.17-2.09 (m, 1H), 1.82-1.73 (m, 2H), 1.61-1.51 (m, 2H), 1.24-1.20 (m, 2H), 1.14-1.08 (m, 2H).

Compound 30 was synthesized from VII-30 as the raw material according to the synthesis method of compound 1, white solid, yield 64%; ¹H NMR (400 MHz, DMSO) δ 7.69-7.62 (m, 2H), 7.57-7.49 (m, 2H), 6.79 (d, J=13.3 Hz, 2H), 4.38 (s, 2H), 3.57-3.45 (m, 3H), 3.17-3.06 (m, 2H), 2.40-2.25 (m, 1H), 1.82-1.66 (m, 2H), 1.44-1.28 (m, 2H), 1.19-1.02 (m, 4H). MS (ESI, m/z): 579 [M+H]⁺.

Example 31

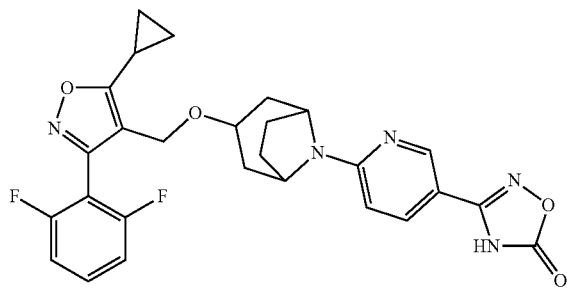

The synthetic route of example 31 was as follows.

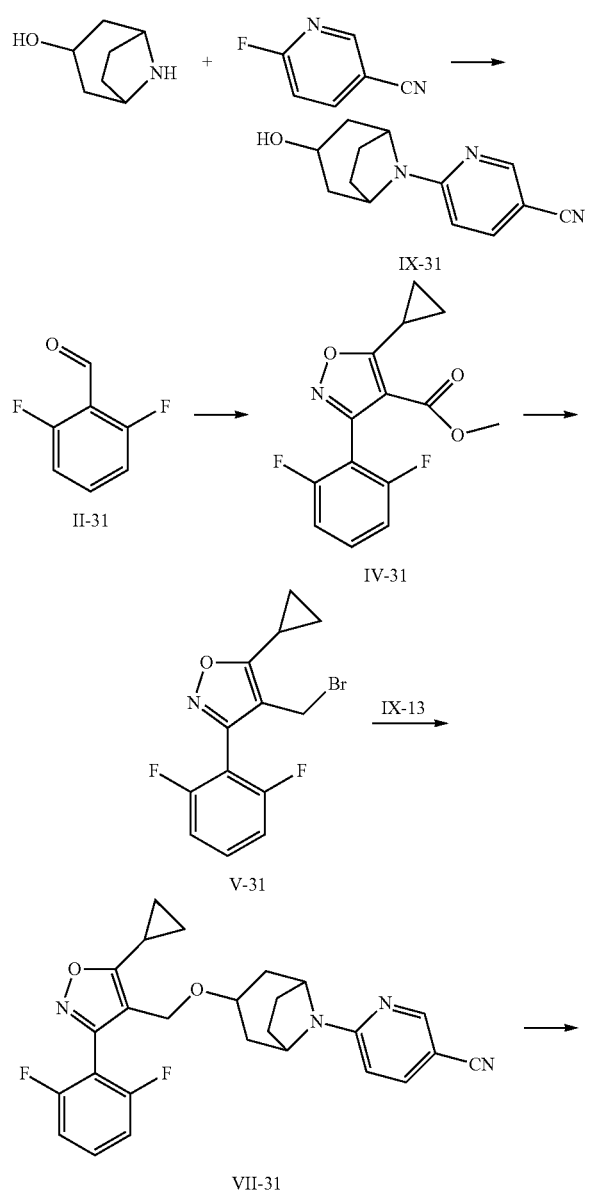

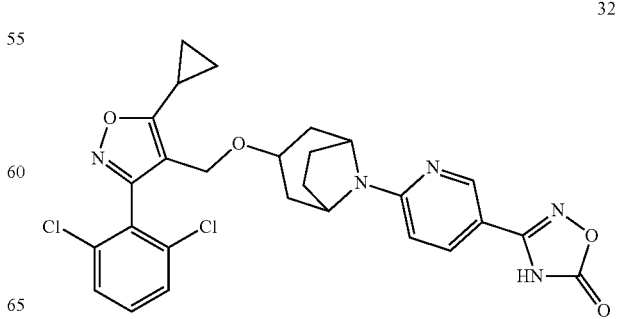

Compound intermediate IX-31 was synthesized from nortropine as the raw material according to the synthesis method of compound IX-10, white solid, yield 94%; $^1$H NMR (400 MHz, CDCl$_3$) δ 8.41 (d, J=1.8 Hz, 1H), 7.58 (dd, J=9.0, 2.3 Hz, 1H), 6.49 (d, J=8.9 Hz, 1H), 4.91-4.26 (m, 2H), 4.12 (t, J=4.7 Hz, 1H), 2.39 (d, J=7.3 Hz, 2H), 2.18-2.04 (m, 4H), 1.81 (d, J=14.3 Hz, 2H);

Compound V-31 was synthesized from 11-31 as the raw material according to the synthesis method of compound 10, wherein, IV-31, white solid, yield 64%. $^1$H NMR (400 MHz, CDCl$_3$) δ 7.43-7.34 (m, 1H), 7.00-6.91 (m, 2H), 3.69 (s, 3H), 2.92-2.83 (m, 1H), 1.36-1.31 (m, 2H), 1.25-1.20 (m, 2H).

V-31, colourless liquid, yield 82%. $^1$H NMR (400 MHz, CDCl$_3$) δ 7.54-7.44 (m, 1H), 7.11-7.04 (m, 2H), 4.33 (s, 2H), 2.20-2.08 (m, 1H), 1.34-1.17 (m, 4H).

Compound intermediate VII-31 was synthesized from V-31 and IX-13 as the raw materials according to the synthesis method of compound VII-10, white solid, yield 55%. $^1$H NMR (400 MHz, CDCl$_3$) δ 8.36 (d, J=2.1 Hz, 1H), 7.53 (dd, J=9.0, 2.1 Hz, 1H), 7.49-6.39 (m, 1H), 7.07-6.96 (m, 2H), 6.42 (d, J=9.0 Hz, 1H), 4.75-4.18 (m, 4H), 3.48 (t, J=4.5 Hz, 1H), 2.16-2.08 (m, 1H), 1.99-1.92 (m, 2H), 1.90-1.81 (m, 4H), 1.69 (d, J=14.5 Hz, 2H), 1.25-1.20 (m, 2H), 1.14-1.08 (m, 2H).

Compound 31 was synthesized from VII-31 as the raw material according to the synthesis method of compound 1, white solid, yield 76%. $^1$H NMR (400 MHz, DMSO) δ 8.46 (d, J=2.3 Hz, 1H), 7.78 (dd, J=9.0, 2.3 Hz, 1H), 7.70-7.59 (m, 1H), 7.29 (t, J=8.0 Hz, 2H), 6.76 (d, J=9.0 Hz, 1H), 4.41 (s, 2H), 4.31 (s, 2H), 3.45 (s, 1H), 2.39-2.26 (m, 1H), 1.86-1.68 (m, 6H), 1.59 (d, J=14.4 Hz, 2H), 1.19-1.03 (m, 4H). MS (ESI, m/z): 522 [M+H]$^+$.

Example 32

The synthetic route of example 32 was as follows.

Example 33

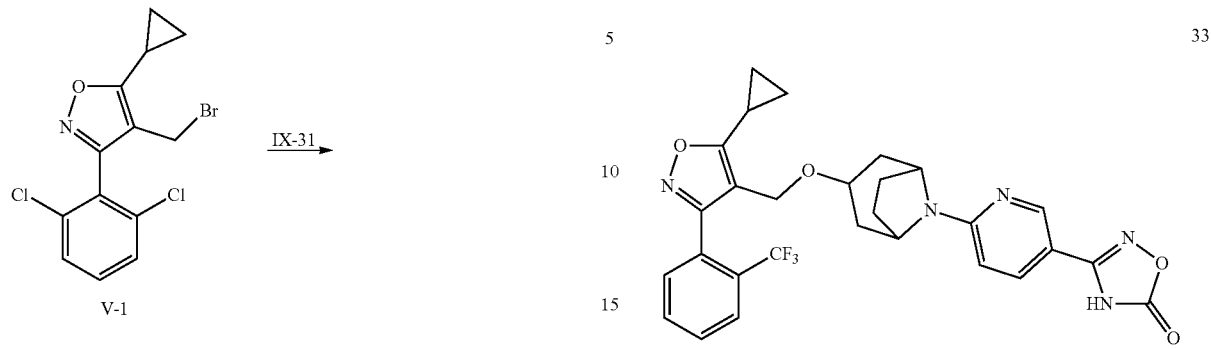

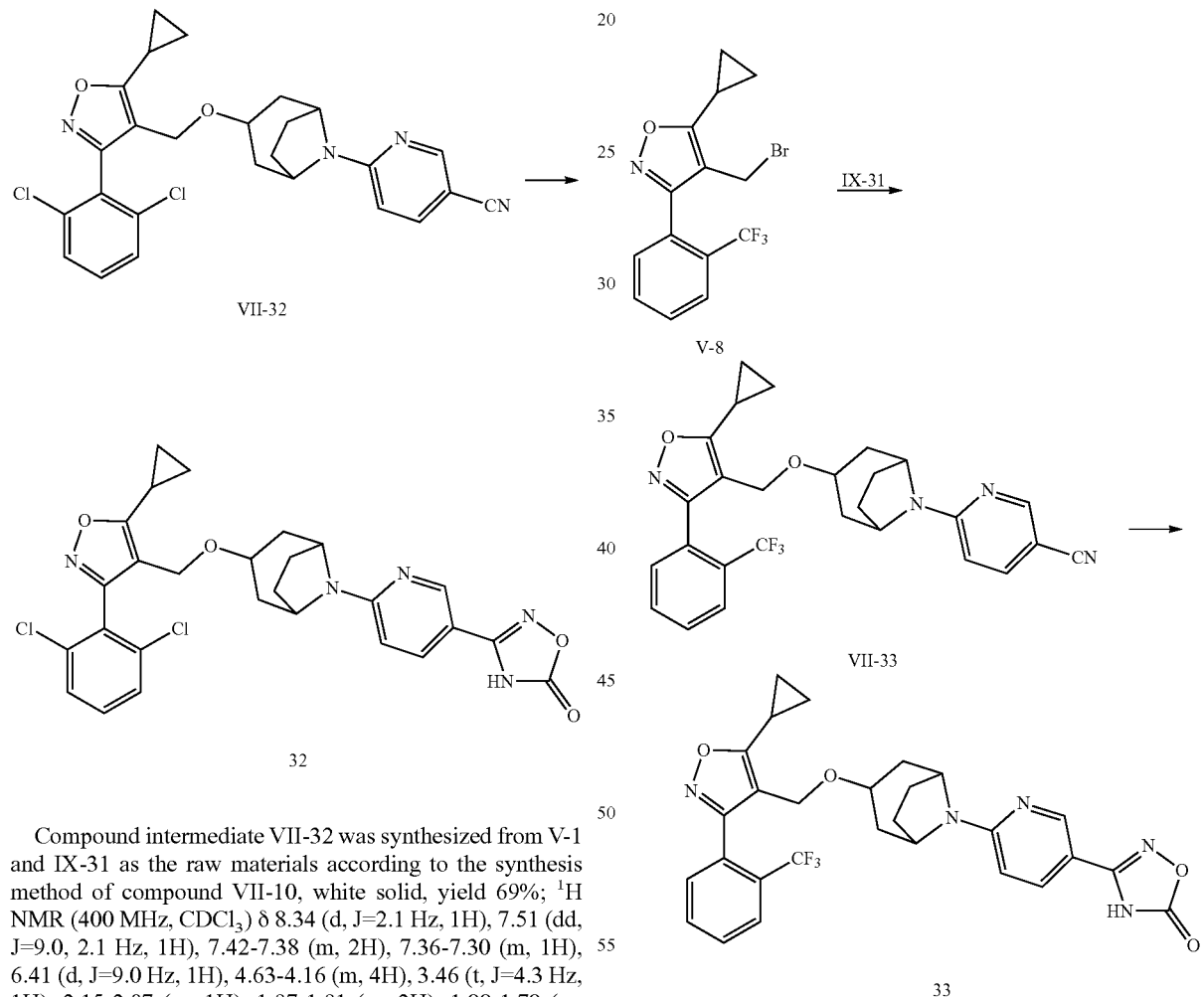

The synthetic route of example 33 was as follows.

Compound intermediate VII-32 was synthesized from V-1 and IX-31 as the raw materials according to the synthesis method of compound VII-10, white solid, yield 69%; $^1$H NMR (400 MHz, CDCl$_3$) δ 8.34 (d, J=2.1 Hz, 1H), 7.51 (dd, J=9.0, 2.1 Hz, 1H), 7.42-7.38 (m, 2H), 7.36-7.30 (m, 1H), 6.41 (d, J=9.0 Hz, 1H), 4.63-4.16 (m, 4H), 3.46 (t, J=4.3 Hz, 1H), 2.15-2.07 (m, 1H), 1.97-1.91 (m, 2H), 1.88-1.78 (m, 4H), 1.70 (d, J=14.5 Hz, 2H), 1.25-1.21 (m, 2H), 1.14-1.07 (m, 2H).

Compound 32 was synthesized from VII-32 as the raw material according to the synthesis method of compound 1, white solid, yield 68%; $^1$H NMR (400 MHz, DMSO) δ 8.45 (d, J=2.3 Hz, 1H), 7.78 (dd, J=9.0, 2.3 Hz, 1H), 7.68-7.60 (m, 2H), 7.59-7.53 (m, 1H), 6.77 (d, J=9.1 Hz, 1H), 4.41 (s, 2H), 4.26 (s, 2H), 3.43 (s, 1H), 2.38-2.28 (m, 1H), 1.86-1.54 (m, 8H), 1.18-1.05 (m, 4H). MS (ESI, m/z): 554 [M+H]$^+$.

Compound intermediate VII-33 was synthesized from V-8 and IX-31 as the raw materials according to the synthesis method of compound VII-10, white solid, yield 73%; $^1$H NMR (400 MHz, CDCl$_3$) δ 8.32 (d, J=2.1 Hz, 1H), 7.76 (d, J=7.3 Hz, 1H), 7.63-7.53 (m, 2H), 7.49 (dd, J=9.0, 2.1 Hz, 1H), 7.44-7.40 (m, 1H), 6.39 (d, J=9.0 Hz, 1H), 4.57-4.12 (m, 4H), 3.42 (t, J=4.3 Hz, 1H), 2.13-2.04 (m, 1H), 1.98-1.91 (m, 2H), 1.88-1.78 (m, 4H), 1.69 (d, J=14.6 Hz, 2H), 1.20-1.15 (m, 2H), 1.11-1.05 (m, 2H).

Compound 33 was synthesized from VII-33 as the raw material according to the synthesis method of compound 1, white solid, yield 51%; $^1$H NMR (400 MHz, DMSO) δ 8.45 (d, J=2.3 Hz, 1H), 7.92 (d, J=7.4 Hz, 1H), 7.84-7.72 (m, 3H), 7.60 (d, J=7.4 Hz, 1H), 6.79 (d, J=9.1 Hz, 1H), 4.19 (s, 2H), 4.23 (s, 2H), 3.43 (s, 1H), 2.37-2.28 (m, 1H), 1.82-1.69 (m, 6H), 1.62 (d, J=14.4 Hz, 2H), 1.17-1.05 (m, 4H). MS (ESI, m/z): 554 [M+H]$^+$.

Example 34

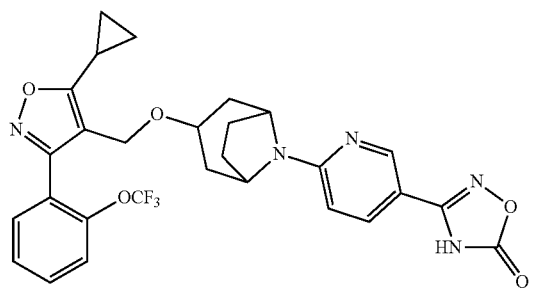

34

The synthetic route of example 34 was as follows,

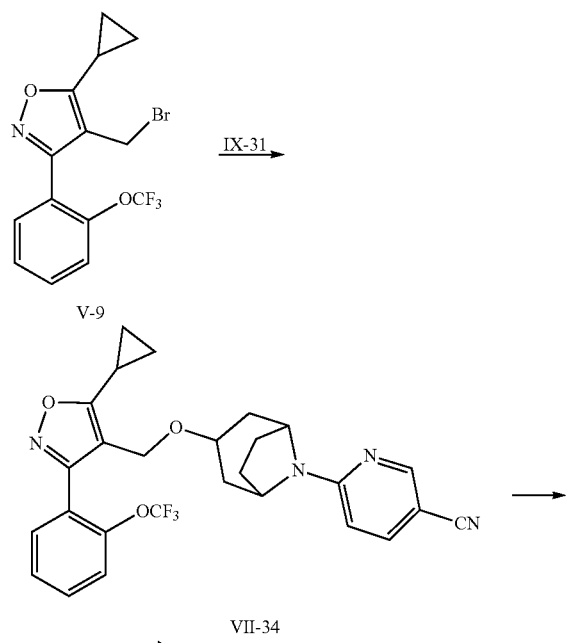

Compound intermediate VII-34 was synthesized from V-9 and IX-31 as the raw materials according to the synthesis method of compound VII-10, white solid, yield 76%: $^1$H NMR (400 MHz, CDCl$_3$) δ 8.35 (d, J=2.1 Hz, 1H), 7.58-7.47 (m, 3H), 7.40-7.35 (m, 2H), 6.44-6.38 (m, 1H), 4.57-4.23 (m, 4H), 3.48 (t, J=4.5 Hz, 1H), 7.16-2.06 (m, 1H), 1.98-1.92 (m, 2H), 1.90-1.82 (m, 4H), 1.70 (d, J=14.5 Hz, 2H), 1.22-1.18 (m, 2H), 1.13-1.07 (m, 2H).

Compound 34 was synthesized from VII-34 as the raw material according to the synthesis method of compound 1, white solid, yield 66%; $^1$H NMR (400 MHz, DMSO) δ 8.47 (d, J=2.3 Hz, 1H), 7.79 (dd, J=9.0, 2.3 Hz, 1H), 7.69-7.59 (m, 2H), 7.56-7.49 (m, 2H), 6.75 (d, J=9.1 Hz, 1H), 4.41 (s, 2H), 4.32 (s, 2H), 3.47 (s, 1H), 2.35-2.26 (m, 1H), 1.86-1.68 (m, 6H), 1.63 (d, J=14.4 Hz, 2H), 1.15-1.02 (m, 4H). MS (ESI, m/z): 570 [M+H]$^+$.

Example 35

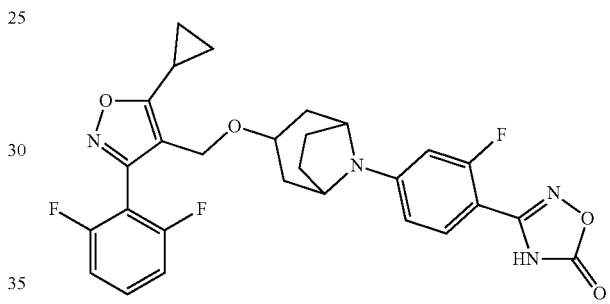

35

The synthetic route of example 35 was as follows.

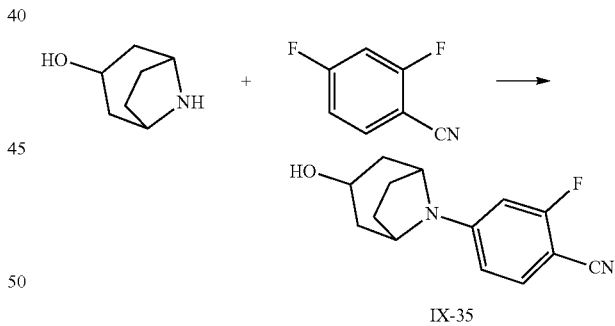

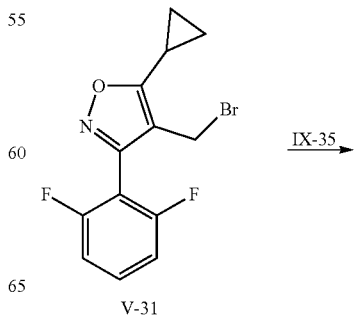

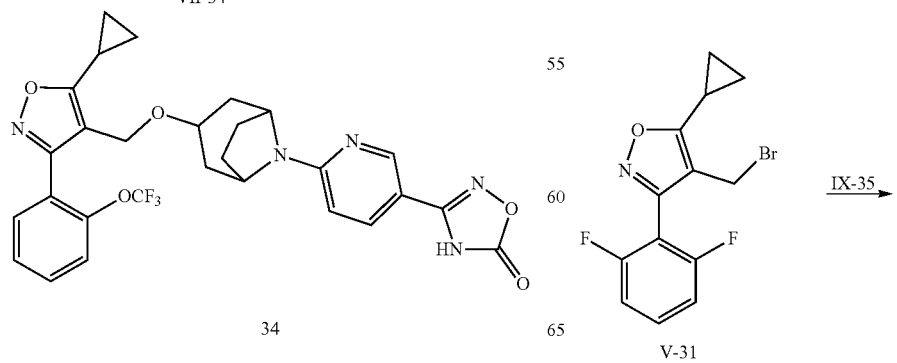

-continued

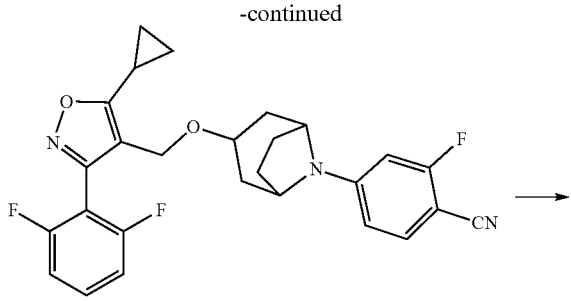

VII-35

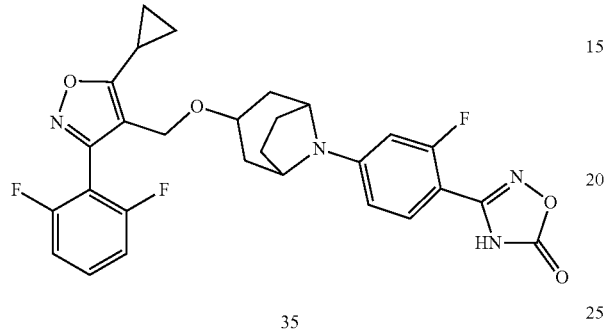

35

Compound intermediate IX-35 was synthesized from nortropine as the raw maternal according to the synthesis method of compound IX-10, white solid, yield 64%; ¹H NMR (400 MHz, CDCl₃) δ 7.42-7.34 (m, 1H), 6.48 (dd, J=8.8, 2.3 Hz, 1H), 6.41 (dd, J=12.8, 2.3 Hz, 1H), 4.21 (s, 2H), 4.09 (t, J=4.4 Hz, 1H), 2.44-2.36 (m, 2H), 2.18-2.05 (m, 4H), 1.74 (d, J=13.9 Hz, 2H), 1.66-1.59 (m, 1H);

Compound intermediate VII-35 was synthesized from V-31 and IX-35 as the raw materials according to the synthesis method of compound VII-10, white solid, yield 79%; ¹H NMR (400 MHz, CDCl₃) δ 7.49-7.41 (m, 1H), 7.37-7.30 (m, 1H), 7.07-7.00 (m, 2H), 6.44-7.31 (m, 2H), 4.31 (s, 2H), 4.06 (s, 2H), 3.46 (t, J=4.5 Hz, 1H), 2.16-2.08 (m, 1H), 1.99-1.92 (m, 2H), 1.91-1.82 (m, 4H), 1.63 (d, J=14.5 Hz, 2H), 1.25-1.20 (m, 2H), 1.15-1.09 (m, 2H).

Compound 35 was synthesized from VII-35 as the raw material according to the synthesis method of compound 1. White solid, yield 66%; ¹H NMR (400 MHz, DMSO) δ 7.70-7.59 (m, 1H), 7.50 (t, J=8.6 Hz, 1H), 7.29 (t, J=8.0 Hz, 2H), 6.76-6.64 (m, 2H), 4.31 (s, 2H), 4.17 (s, 2H), 3.43 (s, 1H), 2.37-2.26 (m, 1H), 1.83-1.67 (m, 6H), 1.52 (d, J=14.5 Hz, 2H), 1.16-1.04 (m, 4H). MS (ESI, m/z): 539 [M+H]⁺.

Example 36

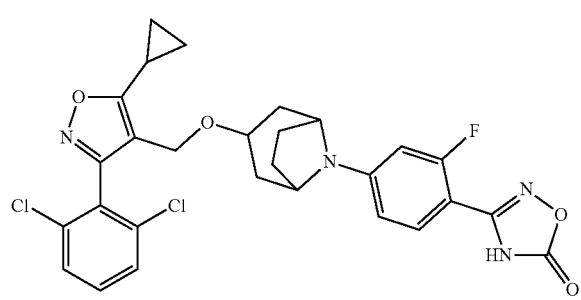

36

The synthetic route of example 36 was as follows.

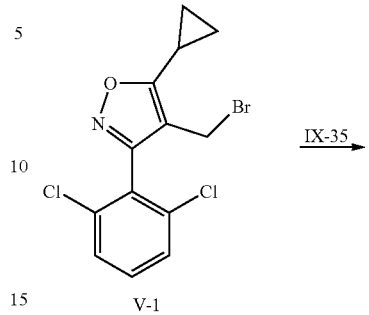

V-1

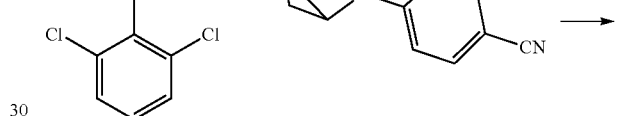

VII-36

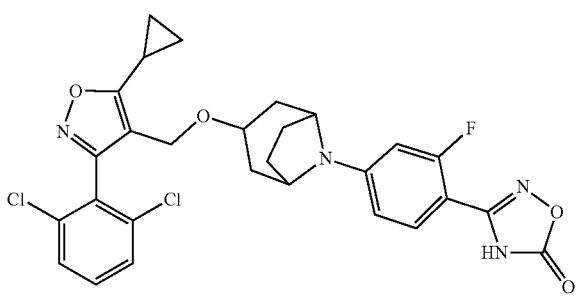

36

Compound intermediate VII-36 was synthesized from V-1 and IX-35 as the raw materials according to the synthesis method of compound VII-10, white solid, yield 73%: ¹H NMR (400 MHz, CDCl₃) δ 7.46-7.41 (m, 2H), 7.39-7.31 (m, 2H), 6.42 (dd, J=8.8, 2.1 Hz, 1H), 6.35 (d, J=12.8 Hz, 1H), 4.26 (s, 2H), 4.07 (s, 2H), 3.46 (t, J=4.4 Hz, 1H), 2.17-2.08 (m, 1H), 2.01-1.95 (m, 2H), 1.91-1.82 (m, 4H), 1.66 (d, J=14.7 Hz, 2H), 1.29-1.24 (m, 2H), 1.17-1.10 (m, 2H).

Compound 36 was synthesized from VII-36 as the raw material according to the synthesis method of compound 1, white solid, yield 65%; ¹H NMR (400 MHz, DMSO) δ 7.65-7.59 (m, 2H), 7.58-7.47 (m, 2H), 6.69 (t, J=12.8 Hz, 2H), 4.25 (s, 2H), 4.17 (s, 2H), 3.41 (s, 1H), 2.38-2.27 (m, 1H), 1.8.-1.68 (m, 6H), 1.54 (d, J=14.5 Hz, 2H), 1.17-1.05 (m, 4H). MS (ESI, m/z): 571 [M+H]⁺.

Example 37

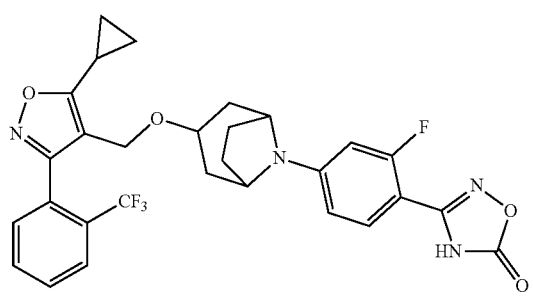

37

The synthetic route of example 37 was as follows.

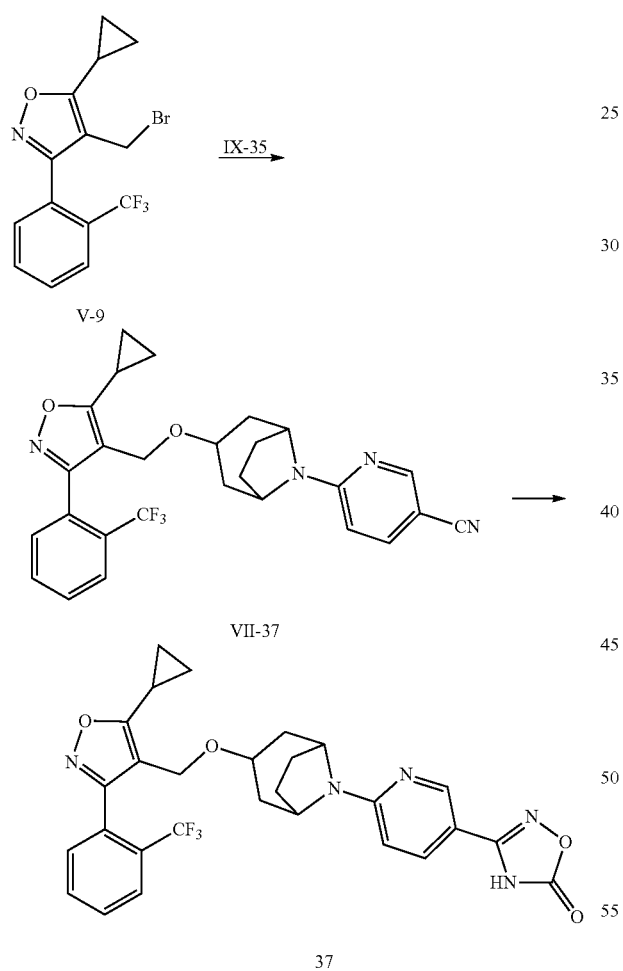

Compound intermediate VII-37 was synthesized from V-8 and IX-35 as the raw materials according to the synthesis method of compound VII-10, white solid, yield 74%; $^1$H NMR (400 MHz, CDCl$_3$) δ 7.84-7.79 (m, 1H), 7.67-7.58 (m, 2H), 7.48-7.42 (m, 1H), 7.39-7.32 (m, 1H), 6.45-6.31 (m, 2H), 4.20 (s, 2H), 4.08 (s, 2H), 3.43 (s, 1H), 2.14-2.07 (m, 1H), 2.02-1.95 (m, 2H), 1.94-1.83 (m, 4H), 1.66 (d, J=14.7 Hz, 2H), 1.29-1.23 (m, 2H), 1.16-1.09 (m, 2H).

Compound 37 was synthesized from VII-37 as the raw material according to the synthesis method of compound 1, white solid, yield 61%; $^1$H NMR (400 MHz, DMSO) δ 7.91 (d, J=7.6 Hz, 1H), 7.83-7.70 (m, 2H), 7.60 (d, J=7.4 Hz, 1H), 7.50 (t, J=8.6 Hz, 1H), 6.75-6.64 (m, 2H), 4.26-4.13 (m, 4H), 3.40 (s, 1H), 2.38-2.24 (m, 1H), 1.83-1.69 (m, 6H), 1.55 (d, J=14.5 Hz, 2H), 1.18-1.03 (m, 4H). MS (ESI, m/z): 571 [M+H]$^+$.

Example 38

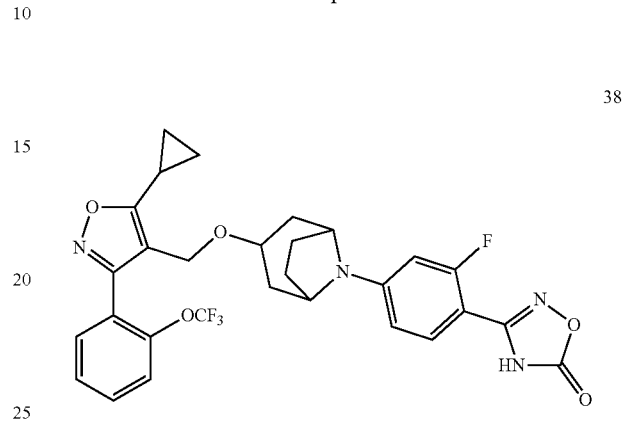

38

The synthetic route of example 38 was as follows.

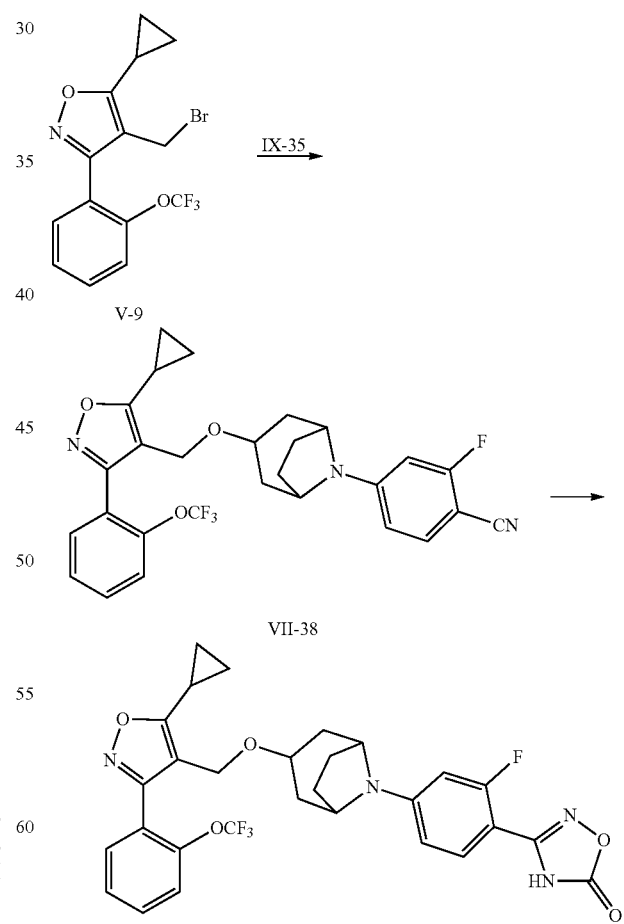

38

Compound intermediate VII-38 was synthesized from V-9 and IX-35 as the raw materials according to the synthesis method of compound VII-10, white solid, yield 74%; $^1$H NMR (400 MHz, CDCl$_3$) δ 7.58-7.50 (m, 2H), 7.43-7.37 (m, 2H), 7.34 (t, J=8.2 Hz, 1H), 6.42 (dd, J=8.8, 2.2 Hz, 1H), 6.35 (dd, J=12.8, 2.2 Hz, 1H), 4.34 (s, 2H), 4.06 (s, 2H), 3.47 (t, J=4.5 Hz, 1H), 2.16-2.07 (m, 1H), 2.00-1.94 (m, 2H), 1.92-1.84 (m, 4H), 1.64 (d, J=14.5 Hz, 2H), 1.26-1.20 (m, 2H), 1.15-1.09 (m, 2H).

Compound 38 was synthesized from VII-38 as the raw material according to the synthesis method of compound 1, white solid, yield 67%; $^1$H NMR (400 MHz, DMSO) δ 7.71-7.60 (m, 2H), 7.58-7.46 (m, 3H), 6.77-6.64 (m, 2H), 4.32 (s, 2H), 4.19 (s, 2H), 3.45 (s, 1H), 2.37-2.27 (m, 1H), 1.86-1.69 (m, 6H), 1.56 (d, J=14.5 Hz, 2H), 1.17-1.04 (m, 4H). MS (ESI, m/z): 587 [M+H]$^+$.

Example 39

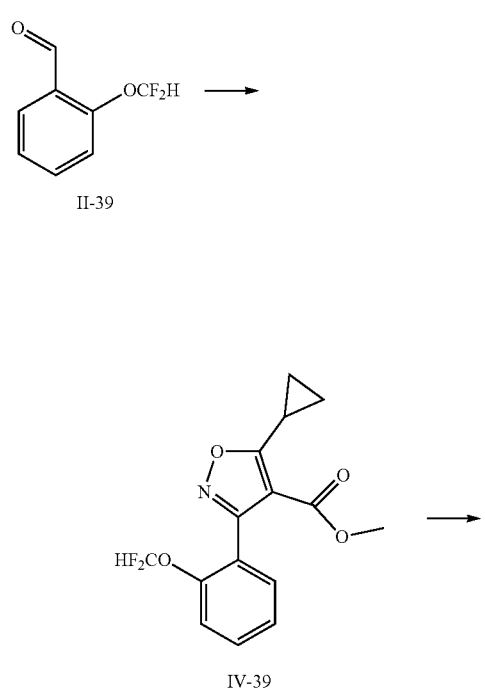

The synthetic route of example 39 was as follows.

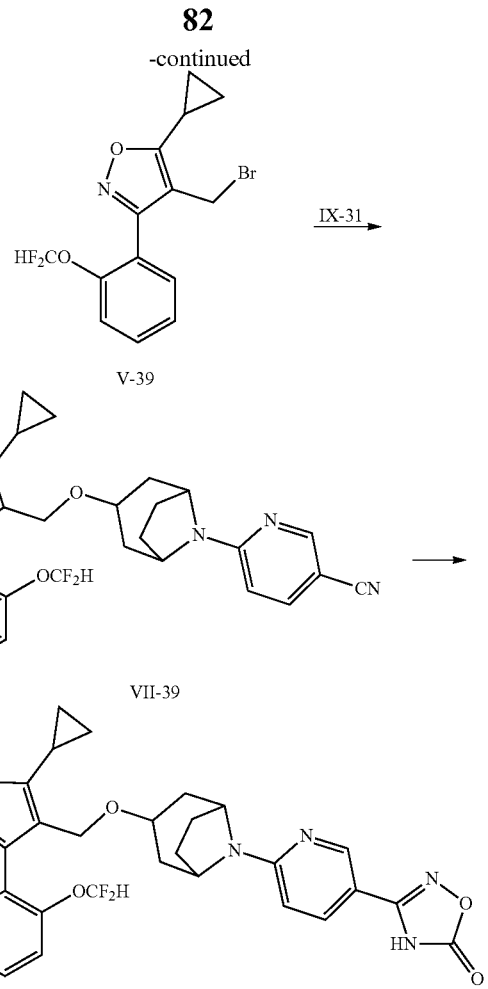

Compound V-39 was synthesized from 11-39 as the raw material according to the synthesis method of compound 10, wherein, IV-39, white solid, yield 54%. $^1$H NMR (400 MHz, CDCl$_3$) δ 7.52-7.44 (m, 2H), 7.32-7.26 (m, 1H), 7.21 (d, J=8.5 Hz, 1H), 6.46 (t, J=73.7 Hz, 1H), 3.72 (s, 3H), 2.88-2.80 (m, 1H), 1.37-1.32 (m, 2H), 1.26-1.22 (m, 2H).

V-39, colourless liquid, yield 72%. $^1$H NMR (400 MHz, CDCl$_3$) δ 7.60-7.51 (m, 2H), 7.41-7.32 (m, 2H), 6.51 (t, J=73.7 Hz, 1H), 4.38 (s, 2H), 2.18-2.10 (m, 1H), 1.32-1.17 (m, 4H).

Compound intermediate VII-39 was synthesized from V-39 and IX-31 as the raw materials according to the synthesis method of compound VII-10, white solid, yield 61%. $^1$H NMR (400 MHz, CDCl$_3$) δ 8.37 (d, J=2.2 Hz, 1H), 7.57-7.45 (m, 3H), 7.35-7.24 (m, 2H), 6.47 (t, J=74.1 Hz, 1H), 6.42 (d, J=8.9 Hz, 1H), 4.34 (s, 4H), 3.49 (t, J=4.5 Hz, 1H), 2.16-2.08 (m, 1H), 2.00-1.94 (m, 2H), 1.90-1.82 (m, 4H), 1.72 (d, J=14.4 Hz, 2H), 1.23-1.20 (m, 2H), 1.14-1.07 (m, 2H).

Compound 39 was synthesized from VII-39 as the raw material according to the synthesis method of compound 1, white solid, yield 78%. $^1$H NMR (400 MHz, DMSO) δ 8.46 (d, J=2.3 Hz, 1H), 7.79 (dd, J=9.0, 2.3 Hz, 1H), 7.64-7.55 (m, 1H), 7.54-7.49 (m, 1H), 7.40-7.33 (m, 2H), 7.23 (d, J=73.6 Hz, 1H), 6.77 (d, J=9.0 Hz, 1H), 4.55-4.23 (m, 4H), 3.46 (s, 1H), 2.36-2.27 (m, 1H), 1.86-1.69 (m, 6H), 1.62 (d, J=14.4 Hz, 2H), 1.15-1.05 (m, 4H). MS (ESI, m/z): 552 [M+H]⁺.

Example 40

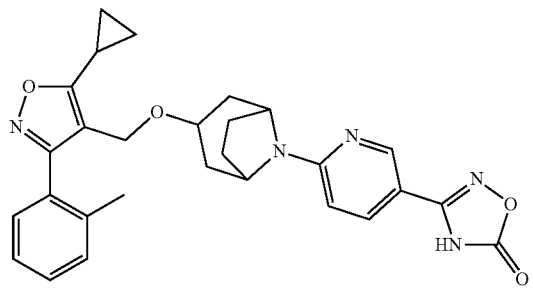

The synthetic route of example 40 was as follows.

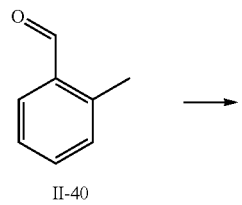

II-40

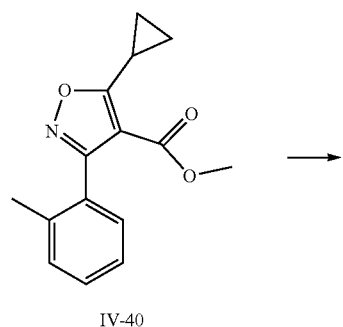

IV-40

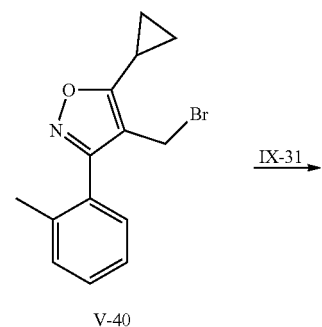

V-40

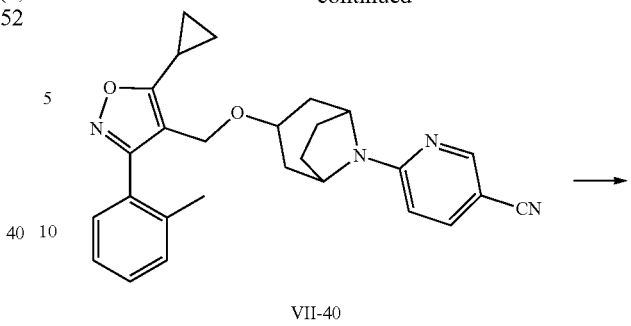

VII-40

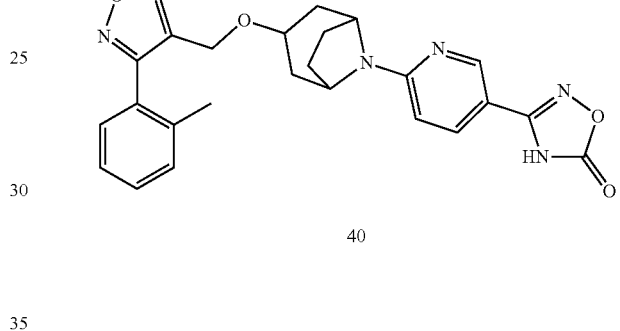

40

Compound V-40 was synthesized from II-40 as the raw material according to the synthesis method of compound 10, wherein, IV-40, white solid, yield 54%. ¹H NMR (400 MHz, CDCl₃) δ 7.42-7.31 (m, 2H), 7.30-7.24 (m, 2H), 3.69 (s, 3H), 2.95-2.87 (m, 1H), 2.23 (s, 3H), 1.42-1.36 (m, 2H), 1.30-1.23 (m, 2H).

V-40, colourless liquid, yield 72%. ¹H NMR (400 MHz, CDCl₃) δ 7.42-7.29 (m, 4H), 4.27 (s, 2H), 2.33 (s, 3H), 2.19-2.10 (m, 1H), 1.32-1.27 (m, 2H), 1.23-1.16 (m, 2H).

Compound intermediate VII-40 was synthesized from V-40 and IX-31 as the raw materials according to the synthesis method of compound VII-10, white solid, yield 61%. ¹H NMR (400 MHz, CDCl₃) δ 8.37 (d, J=1.8 Hz, 1H), 7.54 (dd, J=8.8, 2.3 Hz, 1H), 7.37-7.22 (m, 4H), 6.43 (d, J=8.8 Hz, 1H), 4.76-4.30 (m, 2H), 4.20 (s, 2H), 3.49 (t, J=4.4 Hz, 1H), 2.30 (s, 3H), 2.16-2.10 (m, 1H), 2.07-2.02 (m, 2H), 1.93-1.83 (m, 4H), 1.77 (d, J=14.3 Hz, 2H), 1.26-1.21 (m, 2H), 1.15-1.08 (m, 2H).

Compound 40 was synthesized from VII-40 as the raw material according to the synthesis method of compound 1, white solid, yield 78%. ¹H NMR (400 MHz, DMSO) δ 8.47 (d, J=2.3 Hz, 1H), 7.79 (dd, J=9.0, 2.3 Hz, 1H), 7.39-7.24 (m, 4H), 6.75 (d, J=9.0 Hz, 1H), 4.43 (s, 2H), 4.19 (s, 2H), 3.45 (s, 1H), 2.33-2.24 (m, 1H), 2.21 (s, 3H), 1.92-1.64 (m, 8H), 1.13-1.04 (m, 4H). MS (ESI, m/z): 500 [M+H]⁺.

Example 41

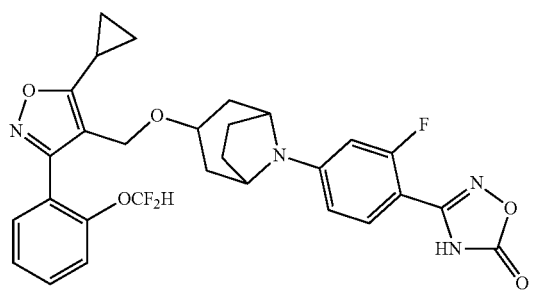

The synthetic route of example 41 was as follows.

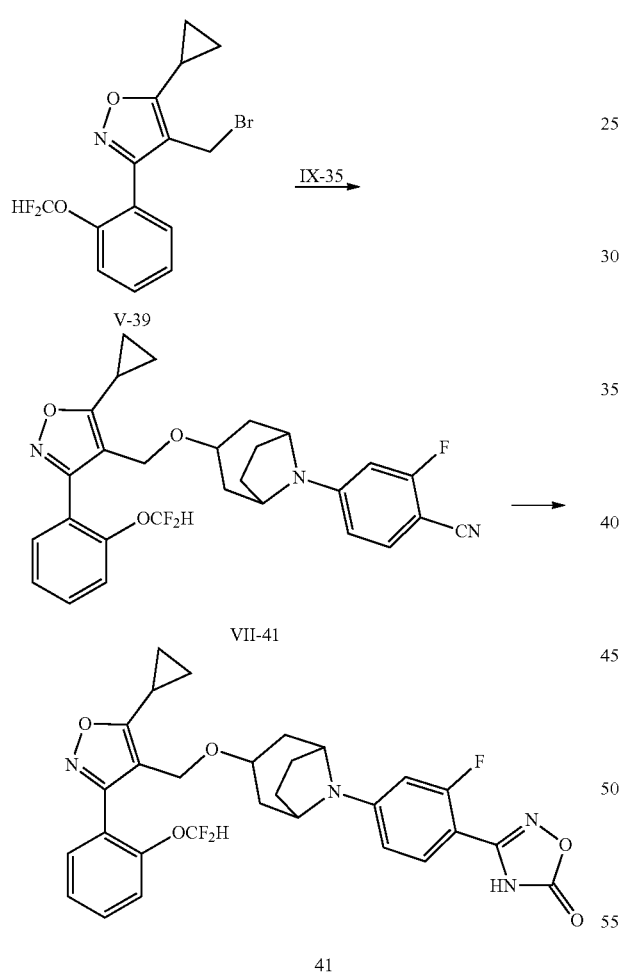

Compound intermediate VII-41 was synthesized from V-41 and IX-35 as the raw materials according to the synthesis method of compound VII-10, white solid, yield 64%. $^1$H NMR (400 MHz, CDCl$_3$) δ 7.55-7.48 (m, 2H), 7.38-7.29 (m, 3H), 6.47 (t, J=74.1 Hz, 1H), 6.45-6.40 (m, 1H), 6.38-6.32 (m, 1H), 4.34 (s, 2H), 4.10-4.03 (m, 2H), 3.52-3.44 (m, 1H), 2.16-2.09 (m, 1H), 2.00-1.95 (m, 2H), 1.92-1.85 (m, 4H), 1.65 (d, J=15.2 Hz, 2H), 1.25-1.22 (m, 2H), 1.15-1.09 (m, 2H).

Compound 39 was synthesized from VII-39 as the raw material according to the synthesis method of compound 1, white solid, yield 71%. $^1$H NMR (400 MHz, DMSO) δ 7.60 (td, J=8.3, 1.7 Hz, 1H), 7.54-7.46 (m, 2H), 7.40-7.34 (m, 2H), 7.23 (t, J=73.6 Hz, 1H), 6.78-6.62 (m, 2H), 4.32 (s, 2H), 4.18 (s, 2H), 3.43 (s, 1H), 2.37-2.27 (m, 1H), 1.86-1.69 (m, 6H), 1.55 (d, J=14.5 Hz, 2H), 1.17-1.02 (m, 4H). MS (ESI, m/z): 569 [M+H]$^+$.

Example 42

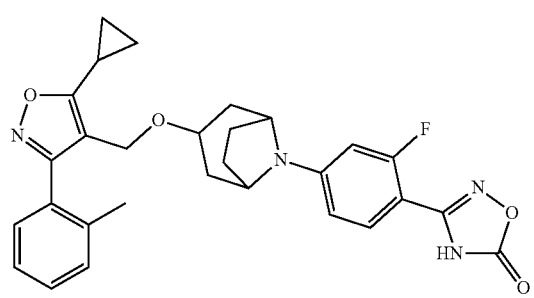

The synthetic route of example 42 was as follows.

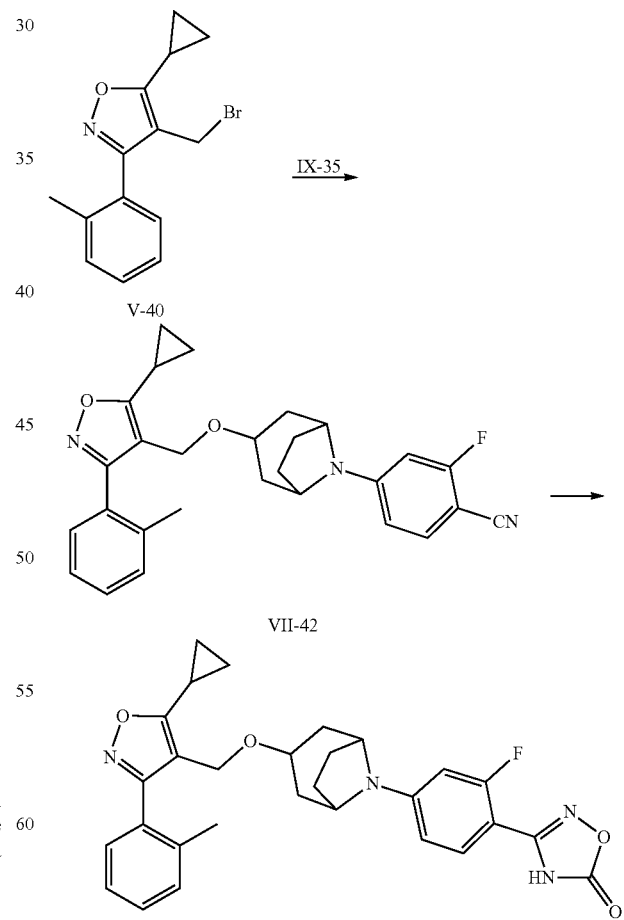

Compound intermediate VII-42 was synthesized from V-40 and IX-35 as the raw materials according to the synthesis method of compound VII-10, white solid, yield 49%. ¹H NMR (400 MHz, CDCl₃) δ 7.28-7.23 (m, 2H), 7.33-7.29 (m, 2H), 7.28-7.23 (m, 1H), 6.46-6.41 (m, 1H), 6.39-6.34 (m, 1H), 4.21 (s, 2H), 4.13-4.06 (m, 2H), 3.50-3.43 (m, 1H), 2.31 (s, 3H), 2.07 (s, 3H), 1.97-1.86 (m, 4H), 1.75-1.67 (m, 2H), 1.29-1.23 (m, 2H), 1.16-1.09 (m, 2H).

Compound 40 was synthesized from VII-40 as the raw material according to the synthesis method of compound 1, white solid, yield 61%. ¹H NMR (400 MHz, CDCl₃) δ 7.66 (t, J=8.7 Hz, 1H), 7.37-7.22 (m, 4H), 6.52 (dd, J=9.0, 1.9 Hz, 1H), 6.39 (dd, J=14.9, 1.9 Hz, 1H), 4.20 (s, 2H), 4.09 (s, 2H), 3.49-3.43 (m, 1H), 2.30 (s, 3H), 2.17-2.01 (m, 3H), 1.92 (dd, J=9.6, 3.4 Hz, 4H), 1.69 (d, J=14.5 Hz, 2H), 1.28-1.20 (m, 2H), 1.17-1.08 (m, 2H). MS (ESI, m/z): 517 [M+H]⁺.

Examples of Pharmacological Experiments

Test Method for FXR Activity at the Molecular Level

FXR activity was determined using recombinant GST-FXR fusion protein by Perkin Elmer's AlphaScreen detection reagent. The reaction in this method was carried out in a 384-well plate, and the total reaction volume was 15 µL. The mixture of protein, agonist, co-regulatory factor, AlphaScreen® acceptor beads and AlphaScreen® donor beads was reacted in a buffer containing Tris-HCl 50 mM (pH7.4), 50 mM NaCl, BSA 0.1%, and 1 mM DTT. The FXR activity was reflected by the fluorescence signal intensity at 570 nm wavelength detected by the Envision fluorescence detector. The value of EC50 was calculated by the software Graphpad Prism 5.

Test Method for FXR Activity at the Cell Level

The FXR expression plasmid and FXRE luciferase reporter plasmid at a ratio of 1:9 was co-transfected into 293T cells, and then the transfected cells were seeded on a 96-well flat-bottom microplate (ViewPlate-96, White 96-well Microplate with Clear Bottom, PerkinElmer) at 5×10⁵/well. The cells were cultured for 24 hours to ensure plasmid expression. Then the FXR receptor agonist to be tested was added and acted for 18 hours. The fluorescence intensity was detected using luciferase kit (steady-Glo Luciferase Assay system) to reflect the compound's activation efficiency on the FXR receptor.

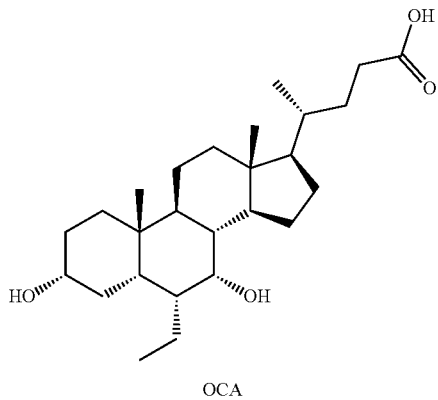

OCA

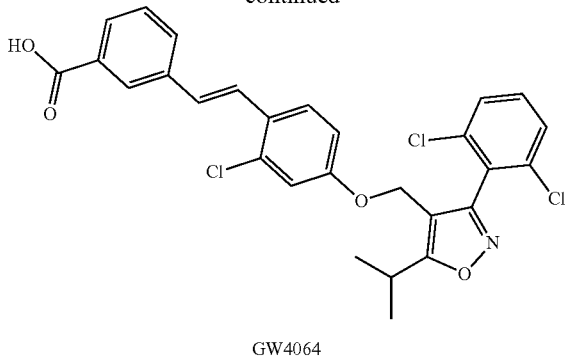

GW4064

In the preliminary screening, the test compound and the two positive compounds OCA, GW4064 acted on the cells at 10 µM, and the relative activities of the test compound to the two positive compounds were determined respectively (relative activity=(signal intensity of test compound-blank)/(signal intensity of positive compound-blank)×100%). The compound whose relative activity is higher than 50% of the positive compound enters the re-screening. The appropriate concentration interval was selected, and the dose-dependent relationship, that is, the EC50 value, was calculated.

TABLE 1

Activity test results

| Test sample | FXR activity at the molecular level EC₅₀ (µM) | Activity relative to OCA (%) 10 µM | FXR activity at the molecular level EC₅₀ (µM) |
|---|---|---|---|
| OCA | 0.374 | 100 | 1.16 |
| GW4064 | 0.98 | 106 | 0.024 |
| Example 1(LXF-32) | 0.446 | 109 | 0.11 |
| Example 2(LXF-73) | 0.072 | 174 | 0.001 |
| Example 3(LXF-114) | 1.81 | 87 | 0.014 |
| Example 4(LXF-111) | 0.015 | 97 | 0.0006 |
| Example 5(LXF-115) | 4.70 | 83 | 0.844 |
| Example 6(LXF-112) | 3.92 | 99 | 0.032 |
| Example 7(LXF-113) | 0.0067 | 88 | 0.006 |
| Example 8(Compound 8) | 0.104 | 88 | 0.005 |
| Example 9(LXF-117) | 0.055 | 90 | 0.004 |
| Example 10(LXF-128) | 1.04 | 202 | 0.0002 |
| Example 11(LXF-129) | 0.439 | 164 | 0.0007 |
| Example 12(LXF-130) | 2.882 | 63 | 0.035 |
| Example 13(LXF-131) | 0.178 | 111 | 0.0007 |
| Example 14(LXF-132) | 0.598 | 74 | 0.005 |
| Example 15(LXF-133) | 2.653 | 159 | 0.003 |
| Example 16(LXF-134) | 0.195 | 168 | 0.0002 |
| Example 17(LXF-135) | 0.257 | 161 | 0.0003 |
| Example 18(LXF-143) | 0.614 | 150 | 0.002 |
| Example 19(LXF-136) | 3.138 | 132 | 0.285 |
| Example 20(LXF-138) | 5.471 | 146 | 0.005 |
| Example 21 | 0.0967 | 117 | 0.00132 |
| Example 22 | 0.386 | 108 | 0.00199 |
| Example 23 | 0.392 | 109 | 0.00222 |
| Example 24 | 0.0590 | 105 | 0.000196 |
| Example 25 | 0.0847 | 103 | 0.00012 |
| Example 26 | 0.0700 | 103 | 0.000254 |
| Example 27 | 0.0209 | 106 | 0.000357 |
| Example 28 | 0.380 | 107 | 0.000617 |
| Example 29 | 0.108 | 120 | 0.000938 |
| Example 30 | 0.0890 | 120 | 0.000255 |
| Example 31 | 0.0113 | 116 | 0.000608 |
| Example 32 | 0.00433 | 103 | 0.0000783 |
| Example 33 | 0.0188 | 141 | 0.000387 |
| Example 34 | 0.0197 | 122 | 0.000388 |

TABLE 1-continued

Activity test results

| Test sample | FXR activity at the molecular level EC$_{50}$ (µM) | FXR activity at the molecular level Activity relative to OCA (%) 10 µM | EC$_{50}$ (µM) |
|---|---|---|---|
| Example 35 | 0.0185 | 117 | 0.000318 |
| Example 36 | 0.00422 | 102 | 0.0000317 |
| Example 37 | 0.0506 | 102 | 0.000284 |
| Example 38 | 0.0513 | 102 | 0.000304 |
| Example 39 | 0.0250 | 108 | 0.00149 |
| Example 40 | 0.0944 | 105 | 0.00211 |
| Example 41 | 0.0285 | 108 | 0.000718 |
| Example 42 | 0.0804 | 106 | 0.000960 |

Conclusion: The test results show that the compounds of the present invention have good agonistic ability to FXR at the molecular level and the cell level, and the activities of several compounds are significantly better than those of the two positive controls.

In Vivo Pharmacological Activity Test of Liver Fibrosis

1) Pharmacodynamic Evaluation of Compound 1 (LXF-32) on TAA-Induced Hepatic Fibrosis Model Rats In this experiment, TAA induced hepatic fibrosis model rats were used to investigate the effect of long-term oral administration of compound 1 on hepatic fibrosis in the model rats.

Experimental method: Male SD rats were intraperitoneally injected with thioacetamide (TAA, dissolved in normal saline) at a dose of 150 mg/kg three times a week to induce a liver fibrosis model. Four weeks after the model was made, the blood was taken from the retro-ocular venous plexus of the rats to detect serum ALP indicators. According to indicators such as ALP and body weight, the rats were randomly divided into 3 groups, each with 8 rats, which were respectively the model control group (Vehicle), Compound 1 group (20 mg/kg), positive compound OCA group (20 mg/kg), etc., orally administered by gavage, once a day. During the administration period, the animal's food intake and body weight were monitored. After 2 weeks of administration, the blood was taken from the retro-ocular venous plexus of the rats to detect serum ALP indicators. After 4 weeks of administration, the blood was taken from the retro-ocular venous plexus and the rats were dislocated and sacrificed. The livers were taken out and weighed. Part of the liver was fixed with 4% paraformaldehyde, and part of the liver was frozen at −80° C. During the whole experiment, another 8 rats in the same cage were injected intraperitoneally with the same volume of normal saline as the system normal control group (WT). This experiment detected indicators such as the level of liver function index ALP in serum, the expression of α-SMA and Col1α1 (fibrosis-related genes) gene level in the liver, the content of hydroxyproline (a characteristic amino acid of collagen) in the liver, and the pathological changes of the liver (Sirius scarlet stain), etc., thereby reflecting whether the compound has the effect of relieving liver fibrosis.

Figure 2:
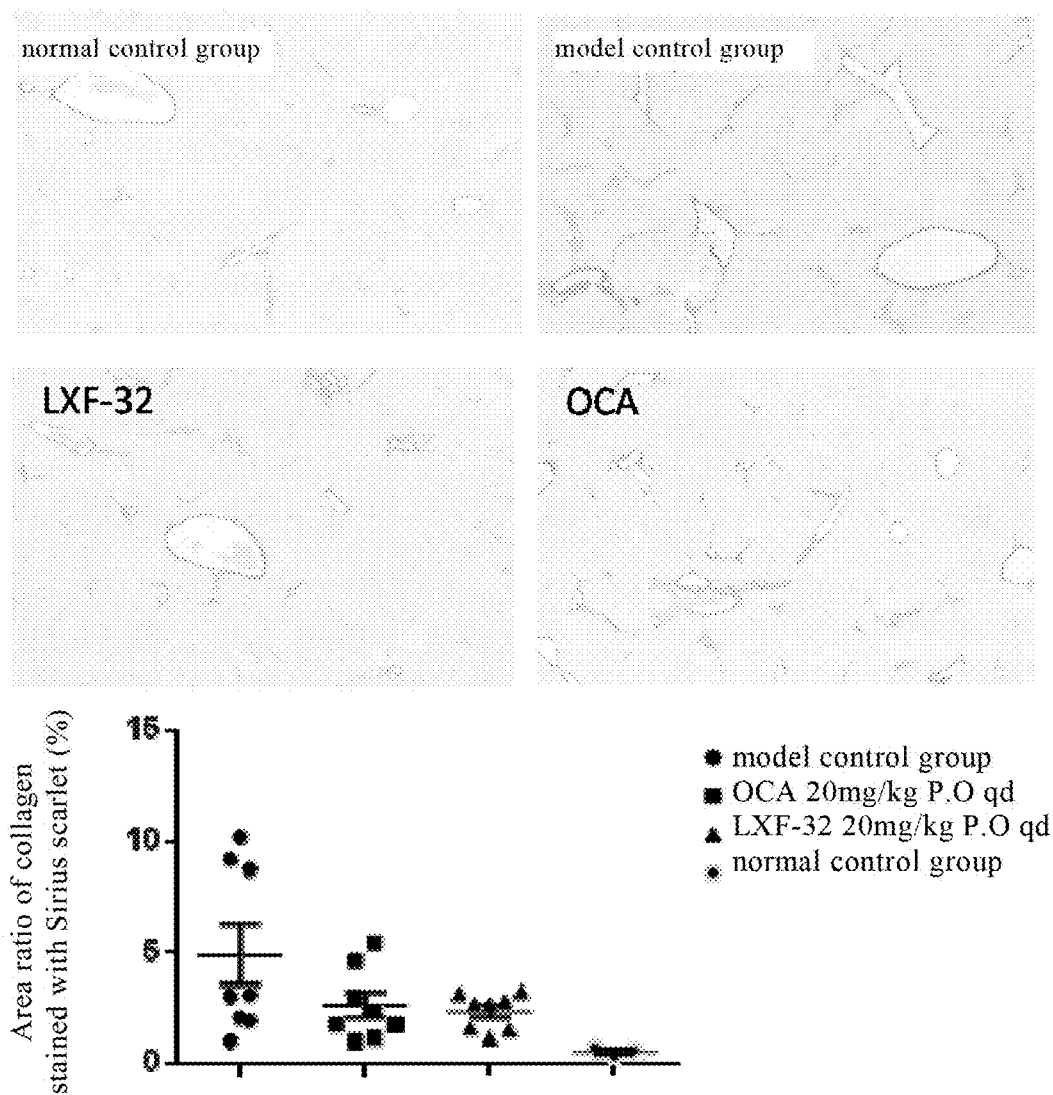
FIG. 2 shows the effect of compound 1 administered for 4 weeks on the content of collagen in liver pathological section.

The research results showed that the compound 1 of the present invention significantly reduced the level of ALP in serum, reduced the content of hydroxyproline in liver tissue, and significantly down-regulated the expression of α-SMA and Col1α1 mRNA in liver tissue after 4 weeks of administration (FIG. 1). In the quantitative analysis of liver pathological sections stained with Sirius Scarlet, compound 1 reduced the collagen content in the liver, because there were large differences within the model group, and there was no statistical difference (FIG. 2).

In summary, long-term administration of compound 1 (LXF-32) of the present invention could significantly improve the liver function of TAA-induced hepatic fibrosis rats, down-regulate the expression of α-SMA and Col1α1 mRNA, reduce the deposition of collagen in the liver, and have a certain alleviating effect on liver fibrosis.

2) Pharmacodynamic Evaluation of Compound 8 (LXF-116) on CCL4-Induced Hepatic Fibrosis Model Mice In this experiment, CCL4 induced hepatic fibrosis model mice were used to investigate the effect of long-term oral administration of compound 8 on hepatic fibrosis in the model mice.

Experimental method: Male C57BL/6j mice were injected intraperitoneally with 2 mL/kg, 10% CCl4 (dissolved in olive oil) three times a week to induce liver fibrosis model. Two weeks after the model was made, the blood was taken from the retro-ocular venous plexus of the mice to detect serum ALT, AST, TBA and LDH indicators. According to ALT, AST, TBA, LDH, body weight and other indicators, the mice were randomly divided into 5 groups. There are 10 animals in each group, namely the model control group (Vehicle), low-dose compound 8 group (6 mg/kg), high-dose compound 8 group (20 mg/kg), low-dose positive compound OCA group (6 mg/kg), high-dose OCA group (20 mg/kg), etc., orally administered by gavage, once a day. During the administration period, the animals' food intake and body weight were monitored. After 3 weeks of administration, the blood was taken from the retro-ocular venous plexus of the mice to detect serum ALT, AST, TBA and LDH indicators. After 6 weeks of administration, the blood was taken from the retro-ocular venous plexus and the mice were dislocated and sacrificed. The livers were taken out and weighed. Part of the liver was fixed with 4% paraformaldehyde, and part of the liver was frozen at −80° C. During the whole experiment, another 10 mice in the same cage were intraperitoneally injected with the same volume of olive oil as the system normal control group (WT).

This experiment detected indicators such as the levels of liver function indicators ALT, AST, TBA, LDH in serum, the expression of α-SMA and Col1α1 gene levels in the liver, and the pathological changes of the liver (Sirius scarlet stain), etc., thereby reflecting whether the compound has the effect of relieving liver fibrosis.

Figure 3:
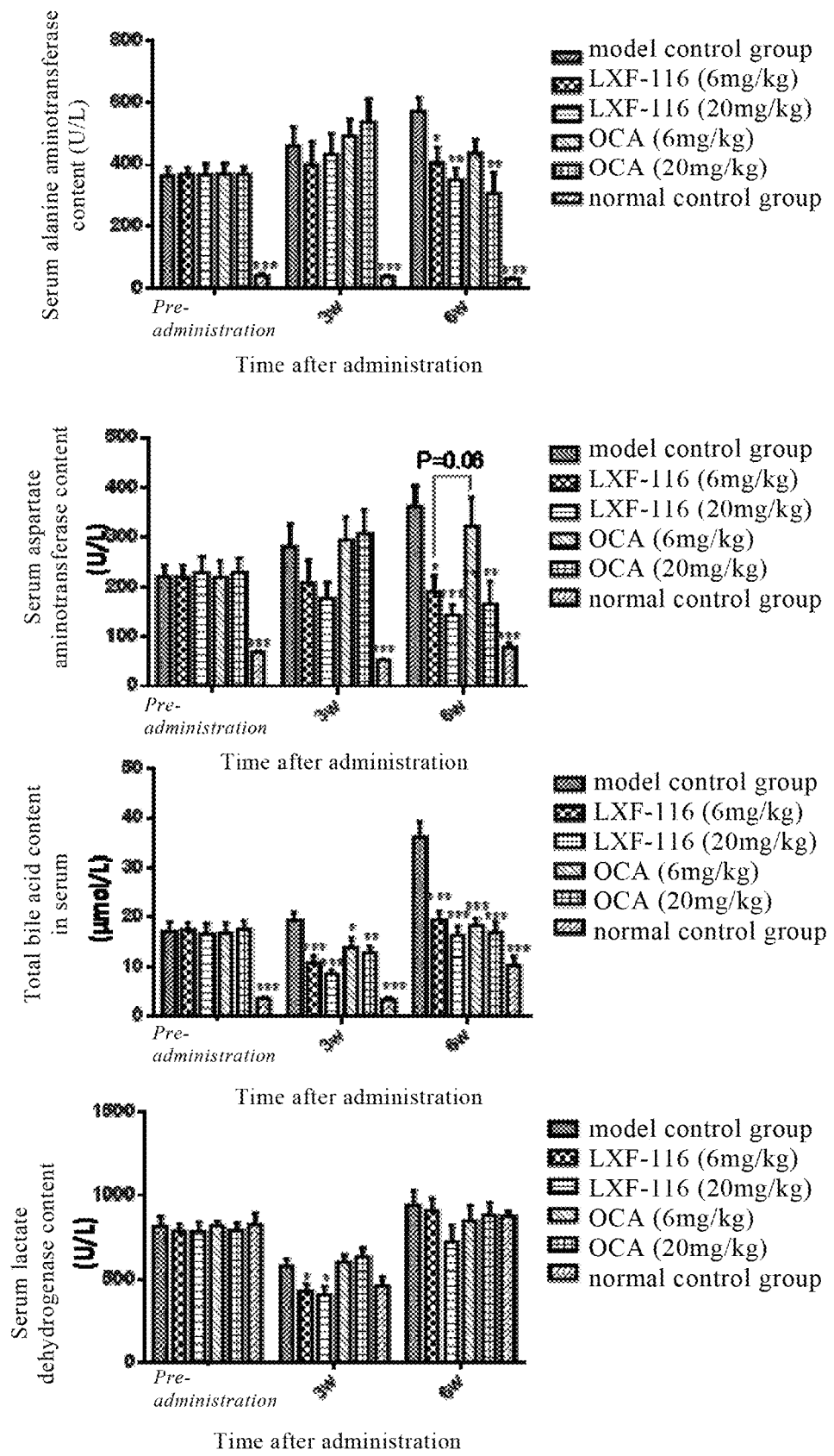
FIG. 3 shows the effect of compound 8 administered for 3 and 6 weeks on ALT, AST, TBA, and LDH levels in serum, *P<0.05, P<0.01, *P<0.001, compared with the model control group (vehicle group).
Figure 4:
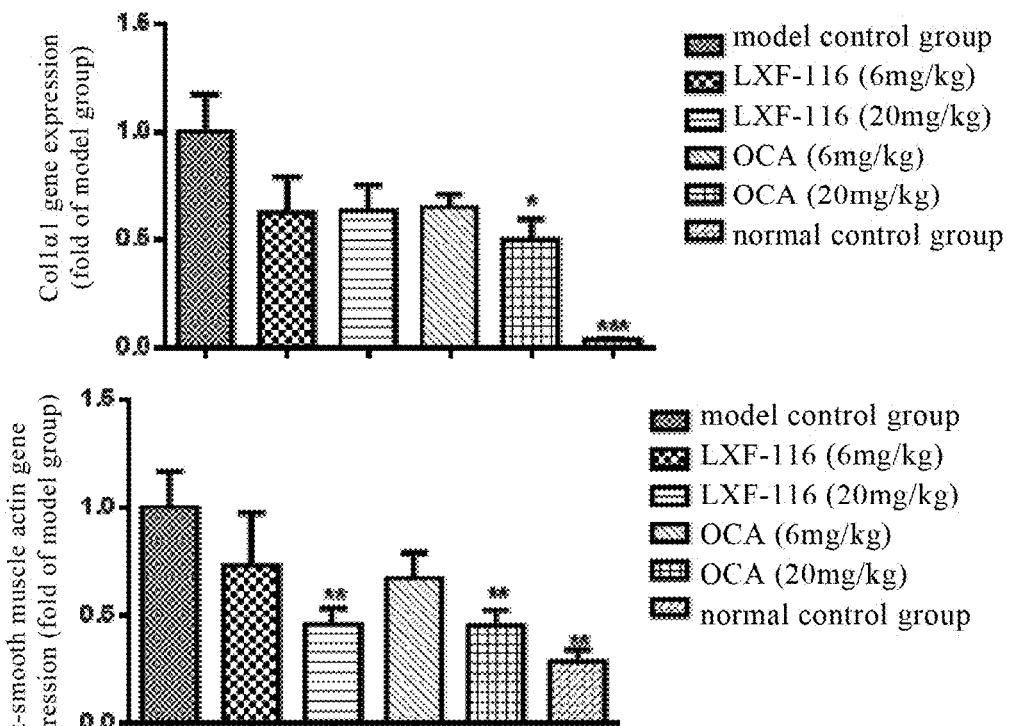
FIG. 4 shows the effect of compound 8 administered for 6 weeks on the expression of α-SMA and Col1α1 mRNA in the liver, *P<0.05. P<0.01, *P<0.001, compared with the model control group (vehicle group).
Figure 4:
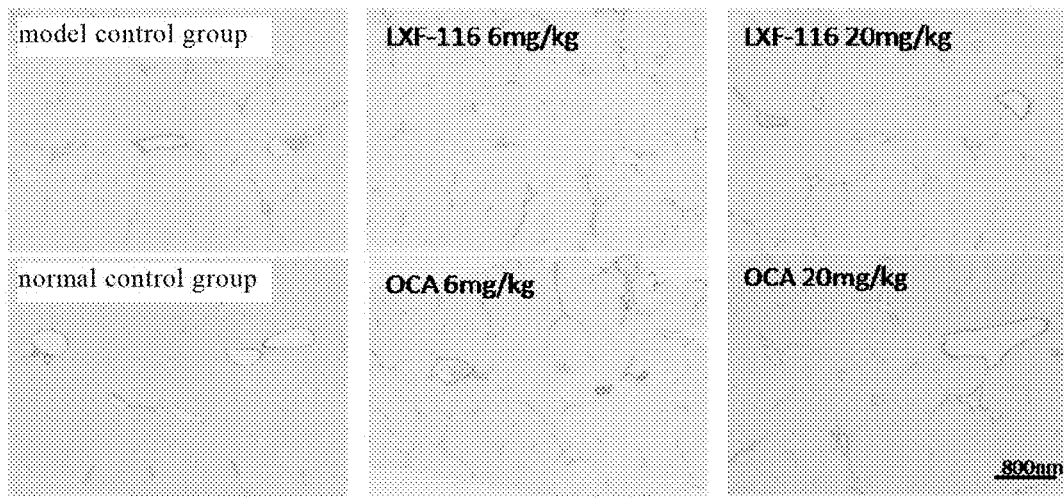
Figure 5:
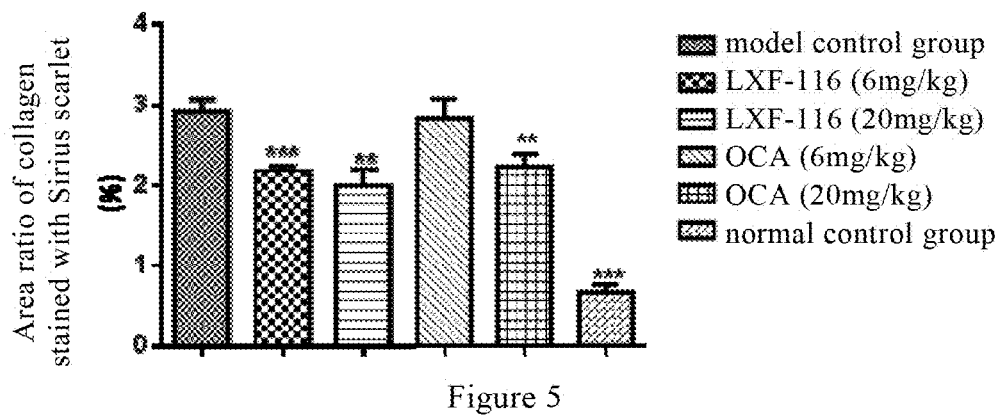
FIG. 5 shows the effect of compound 8 administered for 4 weeks on the content of collagen in liver pathological section, *P<0.05, P<0.01, *P<0.001, compared with the model control group (vehicle group).

The research results showed that the high-dose compound 8 group and low-dose compound 8 group of the present invention significantly reduced the levels of ALT, AST and TBA in serum after 6 weeks of administration, and had little effect on LDH; the high dose positive compound OCA group significantly reduced the levels of ALT, AST and TBA in serum and the low-dose group only had a lowering effect on TBA; the low-dose compound 8 group had a slightly better effect than the low-dose OCA group (FIG. 3). The high-dose compound 8 group significantly down-regulated the expression of α-SMA in the liver, and down-regulated the expression of col1α1 in the liver (FIG. 4); in the quantitative analysis of liver pathological sections stained with Sirius scarlet, both the high-dose compound 8 group and low-dose compound 8 group significantly reduced the collagen content in the liver, and the effect of low-dose compound 8 group was slightly better than that of the low-dose OCA group (FIG. 5).

In summary, long-term administration of compound 8 (LXF-116) of the present invention could significantly improve the liver function of CCl4-induced hepatic fibrosis mice, down-regulate the expression of α-SMA and Col1α1 mRNA, reduce the deposition of collagen in the liver, and have a certain alleviating effect on liver fibrosis All documents mentioned in the present invention are cited as references in this application, just as each document is individually cited as a reference. In addition, it should be understood that after reading the above teaching content of the present invention, those skilled in the art can make various changes or modifications to the present invention, and these equivalent forms also fall within the scope defined by the appended claims of the present application.

The invention claimed is:

1. A compound represented by general formula I, or enantiomer, diastereomer, tautomer, racemate, solvate, prodrug or pharmaceutically acceptable salt thereof,

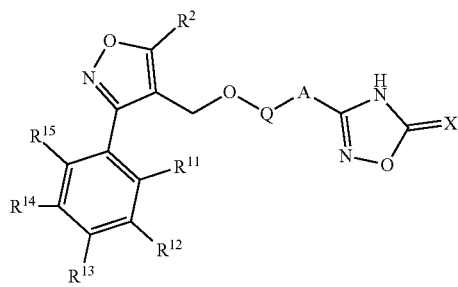

wherein, $R^{11}$, $R^{12}$, $R^{13}$, $R^{14}$ and $R^{15}$ are each independently hydrogen, halogen, halogenated $C_{1-6}$ alkyl, halogenated $C_{1-6}$ alkoxy, $C_{1-6}$ alkyl, $C_{1-6}$ alkoxy, $C_{3}$-$C_{6}$ cycloalkyl, $C_{3}$-$C_{6}$ cycloalkoxy, cyano or nitro;
$R^2$ is $C_6$-$C_{12}$ aryl, $C_1$-$C_6$ alkyl or $C_3$-$C_6$ cycloalkyl;
Q is

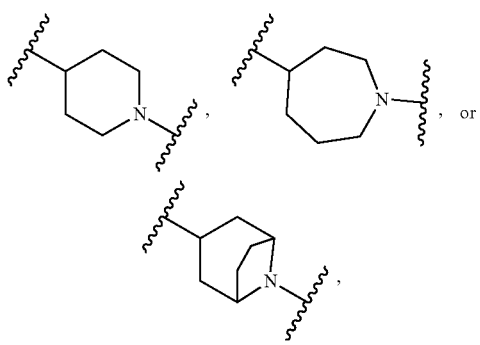

wherein N is attached to A;
A is the following substituted or unsubstituted group: phenyl, pyridyl, thienyl, furyl, indazolyl, indolyl, benzothienyl, benzofuranyl, and the "substituted" means that there is one, two or three substituents selected from the group consisting of halogen, $C_1$-$C_6$ alkyl, halogenated $C_{1-6}$ alkyl, halogenated $C_1$-$C_6$ alkoxy, $C_3$-$C_6$ cycloalkyl, $C_1$-$C_6$ alkoxy, and $C_3$-$C_6$ cycloalkoxy;
X is O or S.

2. The compound of claim 1, wherein $R^{11}$, $R^{12}$, $R^{13}$, $R^{14}$ and $R^{15}$ are each independently hydrogen, fluorine, chlorine, bromine, methyl, ethyl, n-propyl, isopropyl, n-butyl, isobutyl, trifluoromethyl, or trifluoromethoxy.

3. The compound of claim 1, wherein $R^2$ is phenyl, methyl, ethyl, n-propyl, isopropyl, n-butyl, isobutyl, cyclopropyl, cyclobutyl or cyclopentyl.

4. The compound of claim 1, wherein Q is

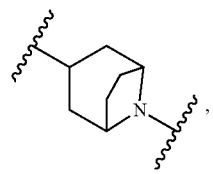

wherein N is attached to A.

5. The compound of claim 1, wherein A is the following substituted or unsubstituted group: phenyl, pyridyl, thienyl, furyl, indazolyl, indolyl, benzothienyl, benzofuranyl; and the "substituted" means that there is one or two substituents selected from the group consisting of fluorine, chlorine, bromine, $C_1$-$C_4$ alkyl, $C_3$-$C_6$ cycloalkyl, $C_1$-$C_4$ alkoxy, and $C_3$-$C_6$ cycloalkoxy.

6. The compound of claim 1, wherein the compound is:

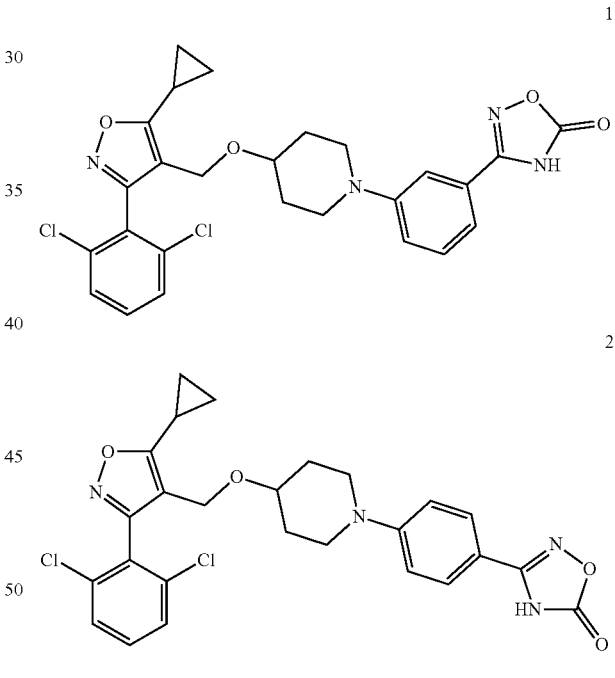

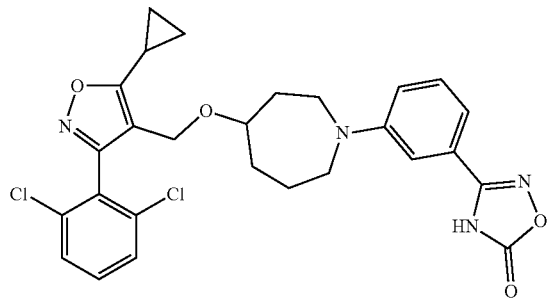

| 93 | 94 |
|---|---|
| 4 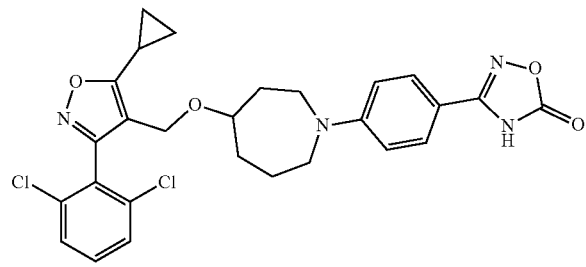 | 11 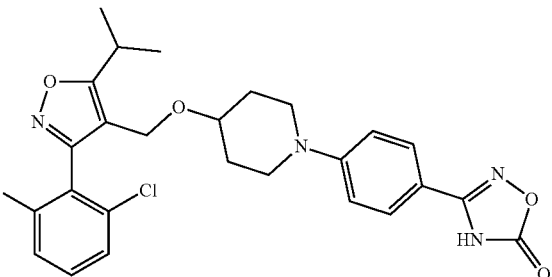 |
| 7 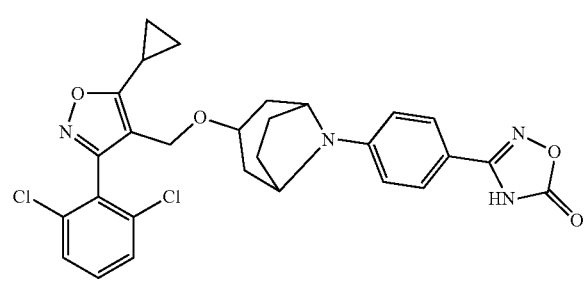 | 12 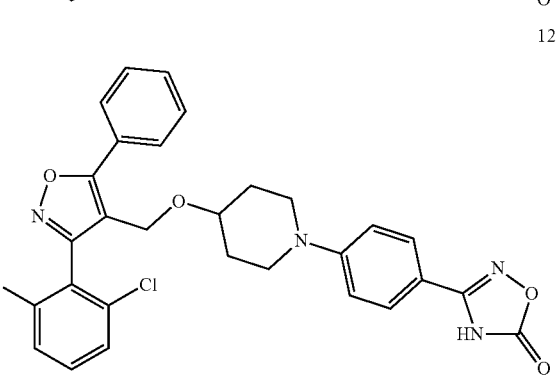 |
| 8 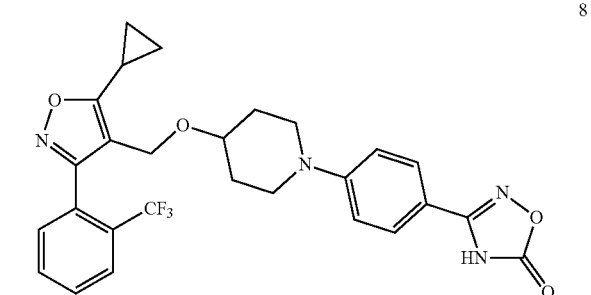 [SMILES: O=c1[nH]c(-c2ccc(N3CCC(OCc4c(-c5ccccc5OC(F)(F)F)noc4C4CC4)CC3)cc2)no1] | 13 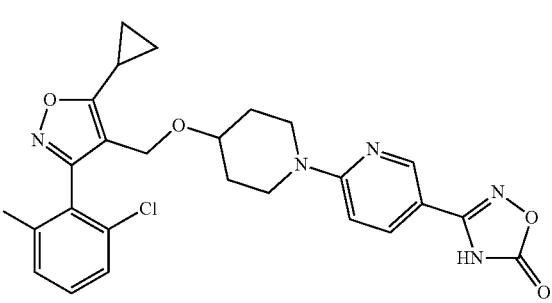 |
| 9 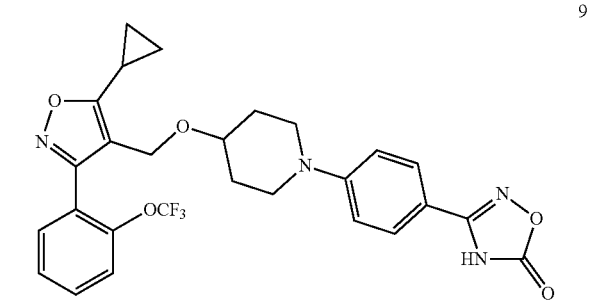 | 14 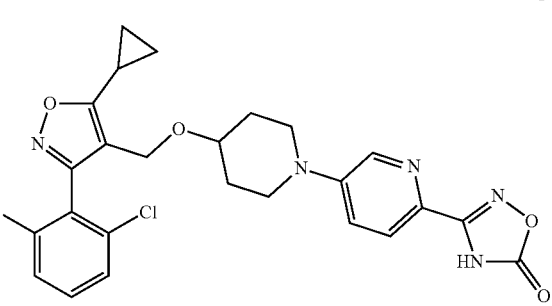 |
| 10 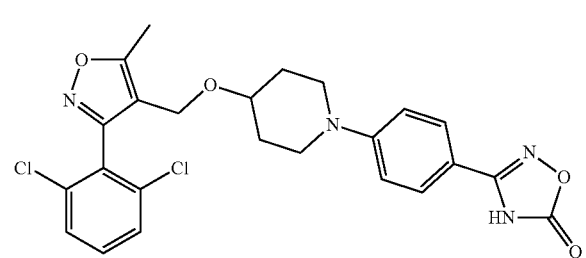 | 15 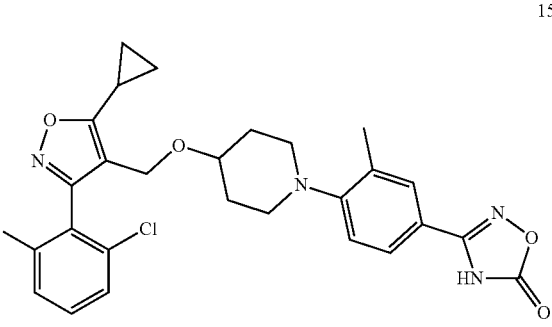 |

16
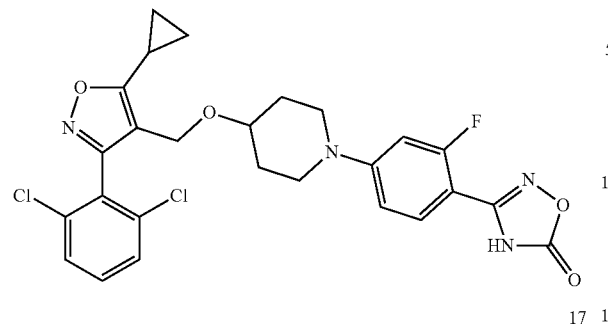
17
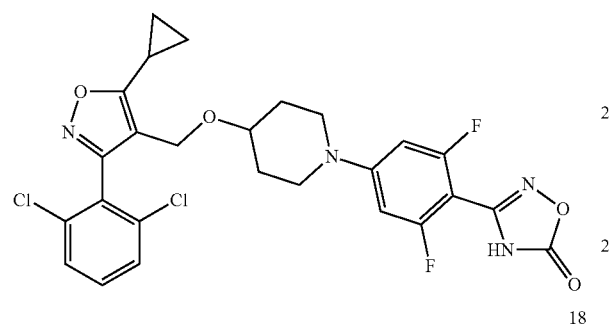
18
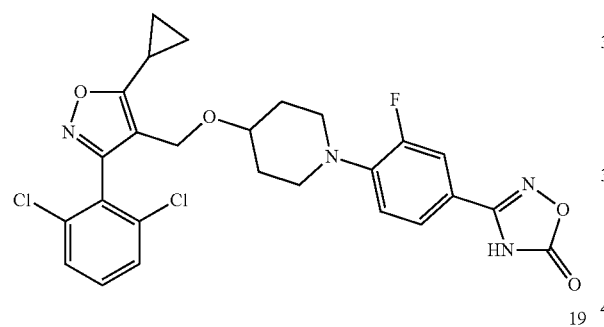
19
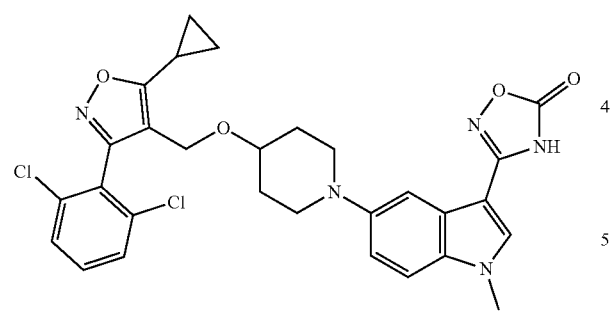
20
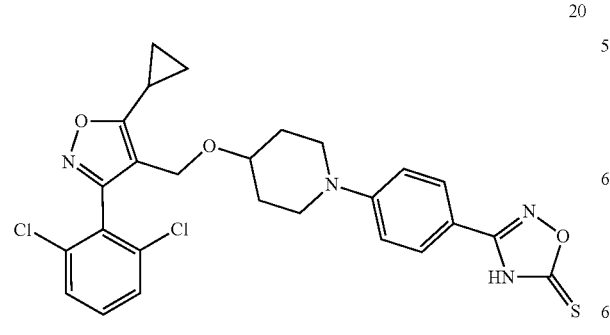
21
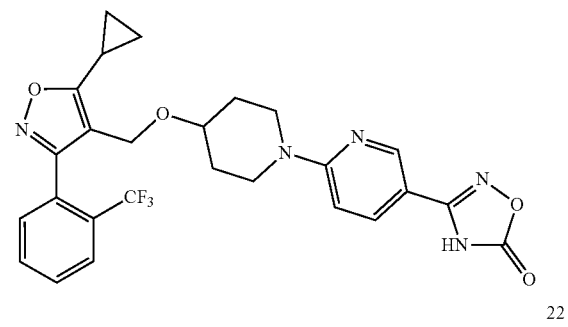
22
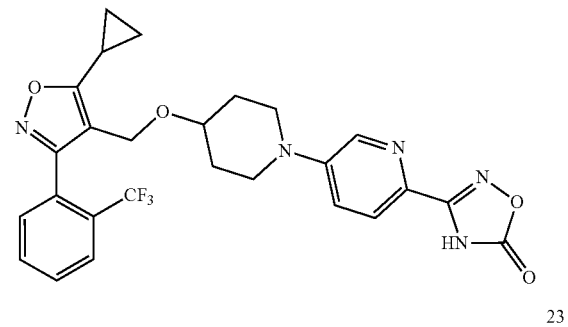
23
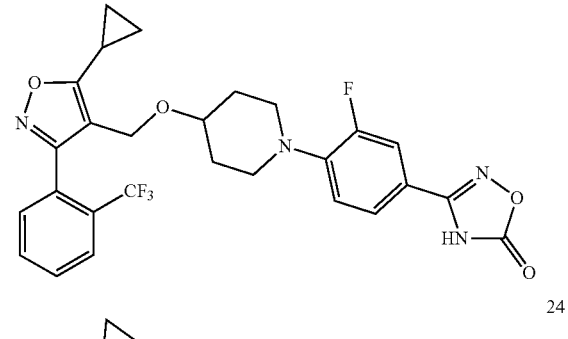
24
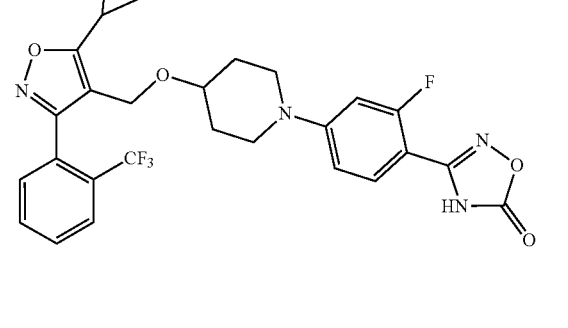
25
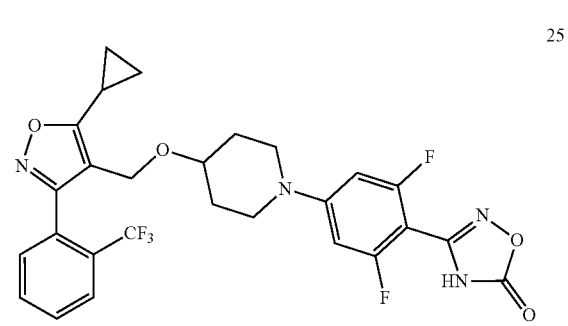

26
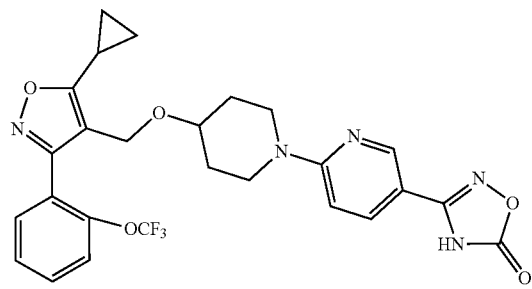
27
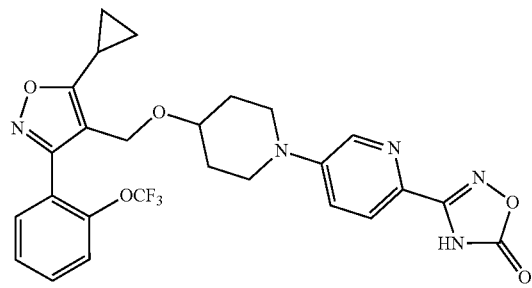
28
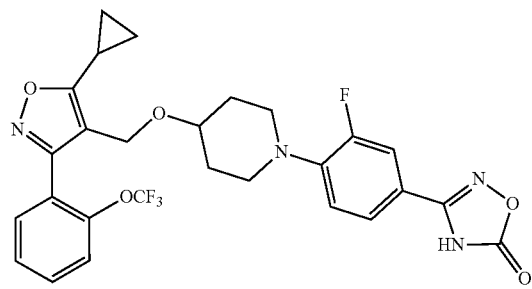
29
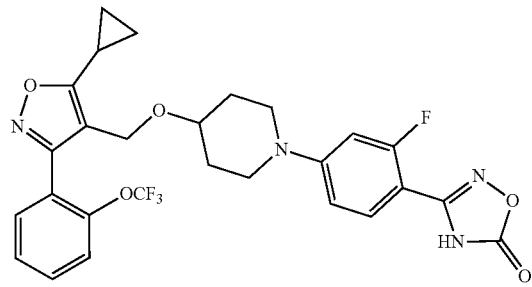
30
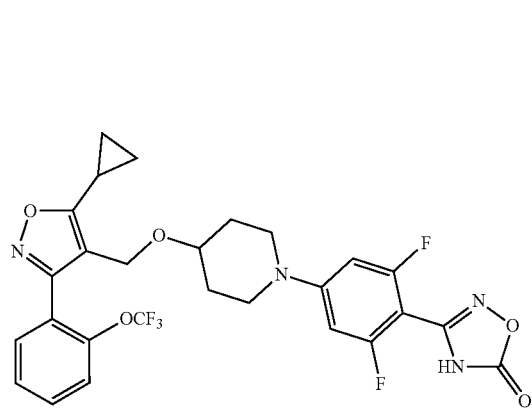
31
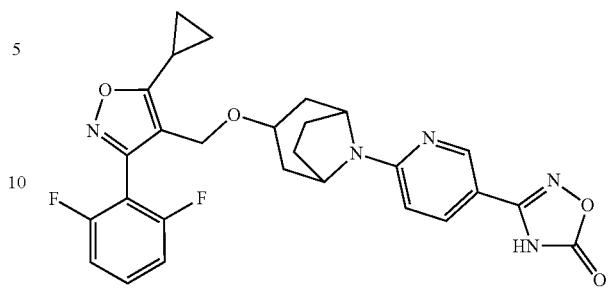
32
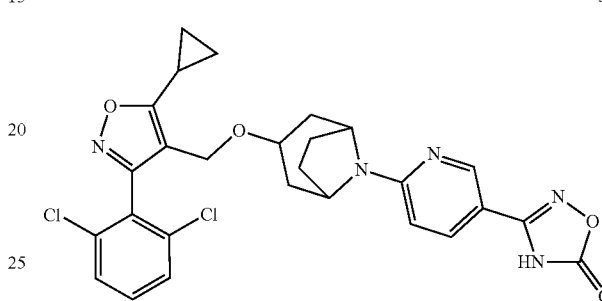
33
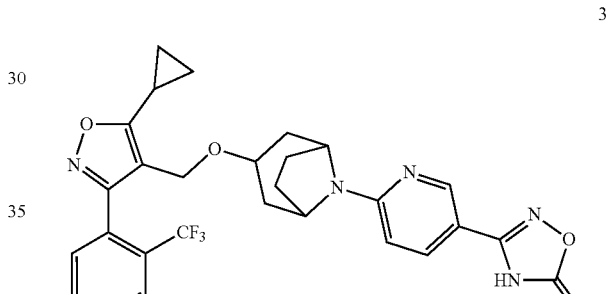
34
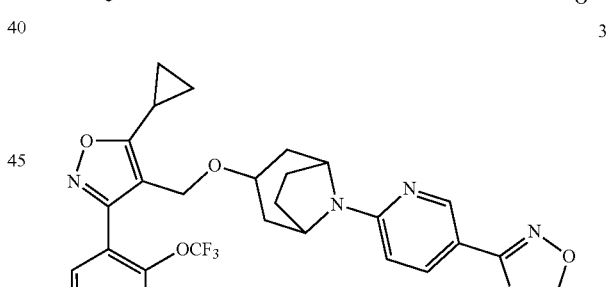
35
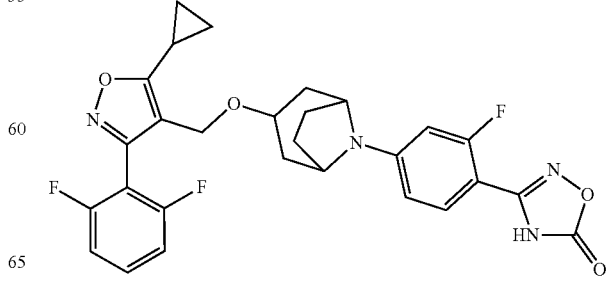

36
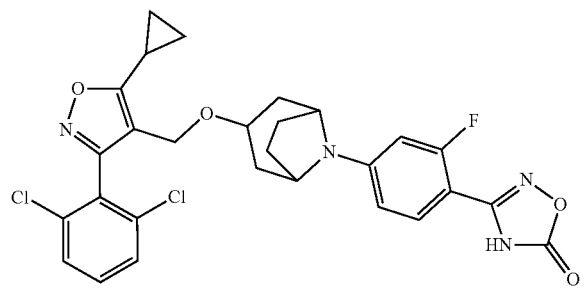
37
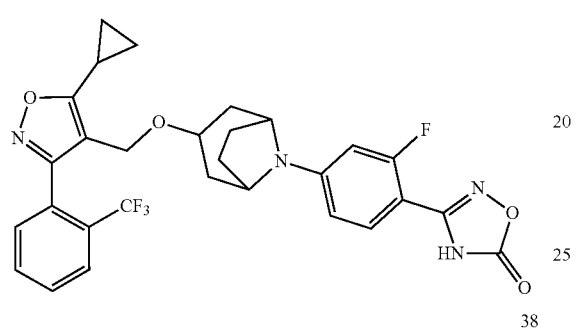
38
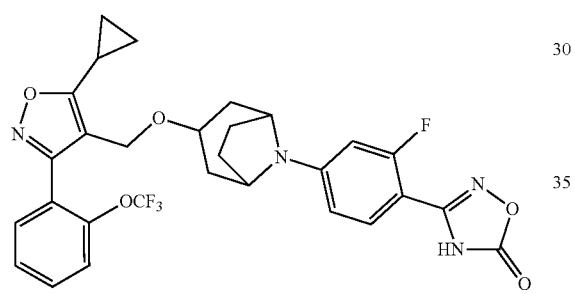
39
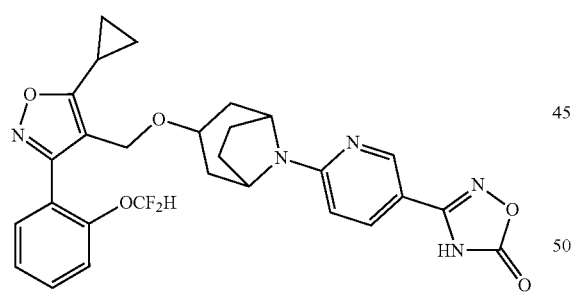
40
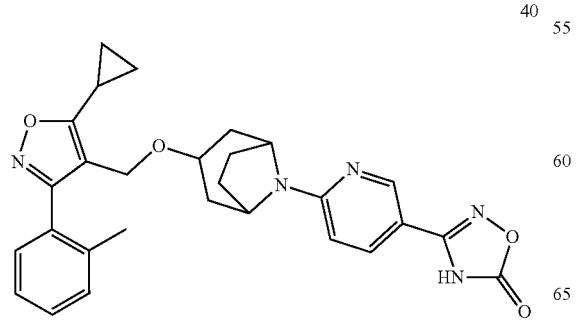
41
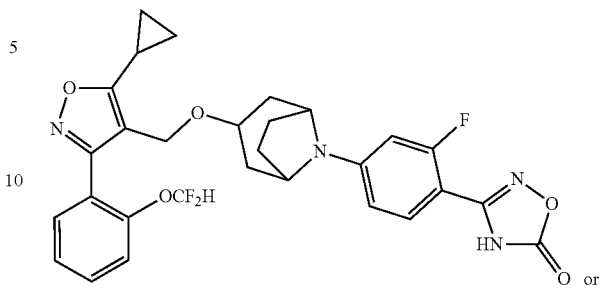
or
42
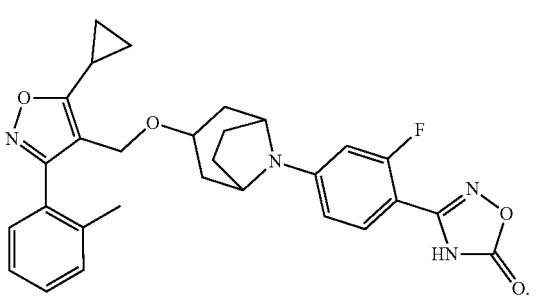
.
7. A method for preparing the compound according to claim 1, wherein the method comprises the following steps:
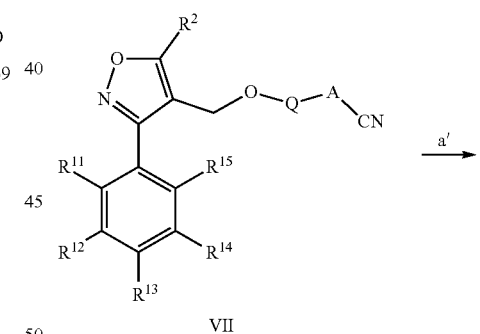
VII
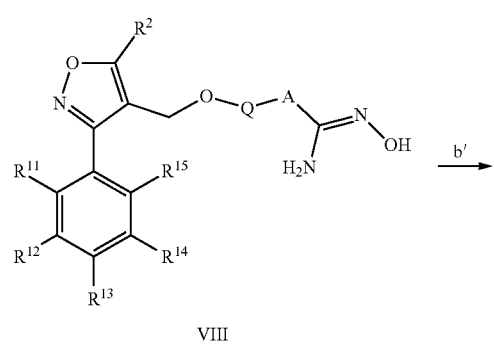
VIII

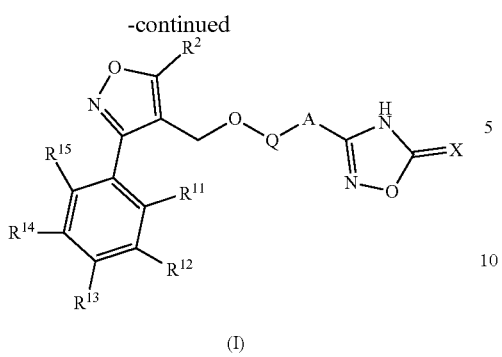

(I)

(a') reacting a compound represented by general formula VII with hydroxylamine hydrochloride to produce a compound represented by general formula VIII;

(b') reacting the compound represented by the general formula VIII under the action of phosgene, triphosgene, carbonyldiimidazole or thiocarbonyldiimidazole to produce the compound represented by the general formula I, wherein, X, $R^2$, Q, A, $R^{11}$, $R^{12}$, $R^{13}$, $R^{14}$ and $R^{15}$ are defined as in claim 1.

8. The method of claim 7, wherein the compound represented by the general formula VII is prepared by the following steps:

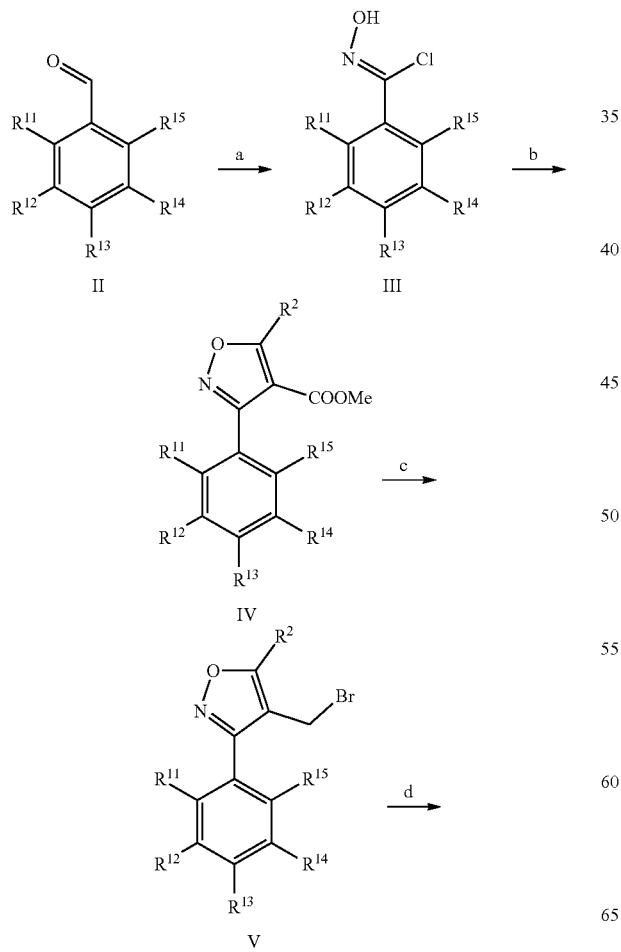

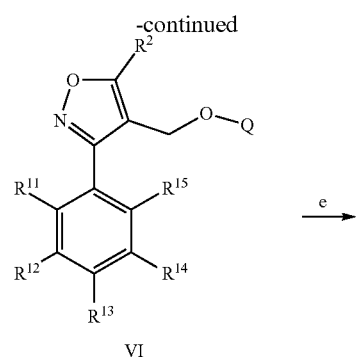

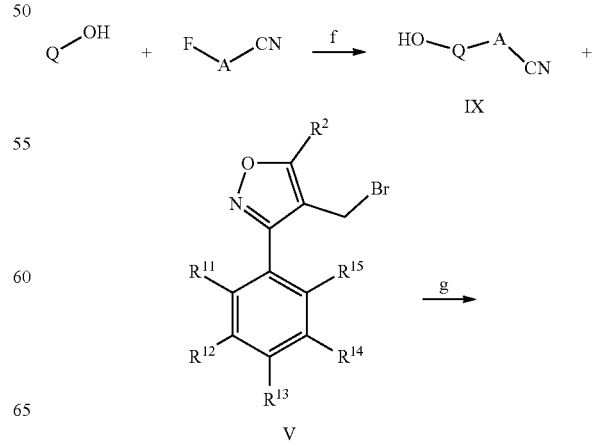

a) reacting substituted benzaldehyde compound represented by general formula II as starting materials with hydroxylamine hydrochloride to obtain an intermediate and then chlorinating the intermediate with N-chlorosuccinimide (NCS) to produce a compound represented by general formula III;

b) reacting the compound represented by the general formula III with 3-oxopropionate to obtain a compound represented by the general formula IV;

c) reducing the ester in the compound represented by formula IV to produce alcohol, and then brominating to produce a compound represented by V;

d) reacting the compound represented by general formula V with Q-OH to produce a compound represented by general formula VI;

e) coupling the compound represented by general formula VI with Br-A-CN under the catalysis of copper or palladium to obtain the compound represented by general formula VII, or prepared by the following steps:

-continued

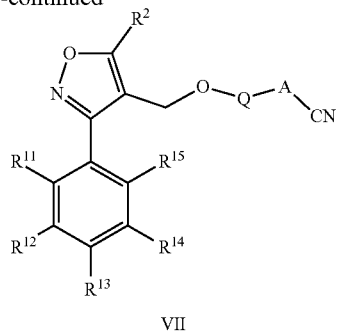

VII f) reacting Q-OH with F-A-CN to generate a compound represented by general formula IX;

g) reacting a compound represented by the general formula V with the compound represented by the general formula IX to produce the compound represented by the general formula VII, in each formula, $R^2$, Q, A, $R^{11}$, $R^{12}$, $R^{13}$, $R^{14}$ and $R^{15}$ are defined as in claim 1.

9. A pharmaceutical composition comprising the compound of claim 1, or the enantiomer, diastereomer, tautomer, racemate, solvate, prodrug, or pharmaceutically acceptable salt thereof; and
a pharmaceutically acceptable carrier.

10. An Farnesoid X receptor (FXR) agonist comprising the compound of claim 1 or the enantiomer, diastereomer, tautomer, racemate, solvate, prodrug, or pharmaceutically acceptable salt thereof.

11. A medicament for the treatment of a Farnesoid X receptor (FXR)-related disease comprising a compound of claim 1 or the enantiomer, diastereomer, tautomer, racemate, solvate, prodrug, or pharmaceutically acceptable salt thereof, wherein the FXR-related disease is a metabolic syndrome.

12. A method for reducing the levels of ALP, ALT, AST and TBA in serum in a subject in need thereof, the method comprising administering a compound of claim 1 or the enantiomer, diastereomer, tautomer, racemate, solvate, prodrug, or pharmaceutically acceptable salt thereof.

13. A method for reducing the amount of hydroxyproline in liver tissue in a subject in need thereof, the method comprising administering a compound of claim 1 or the enantiomer, diastereomer, tautomer, racemate, solvate, prodrug, or pharmaceutically acceptable salt thereof.

14. A method for down-regulating the expression of α-SMA and Colla1 mRNA in liver tissue in a subject in need thereof, the method comprising administering a compound of claim 1 or the enantiomer, diastereomer, tautomer, racemate, solvate, prodrug, or pharmaceutically acceptable salt thereof.

15. A method for reducing the content of collagen in the liver in a subject in need thereof, the method comprising administering a compound of claim 1 or the enantiomer, diastereomer, tautomer, racemate, solvate, prodrug, or pharmaceutically acceptable salt thereof.

* * * * *